US010985330B2

(12) United States Patent
Parham et al.

(10) Patent No.: US 10,985,330 B2
(45) Date of Patent: Apr. 20, 2021

(54) MATERIALS FOR ELECTRONIC DEVICES

(71) Applicant: Merck Patent GmbH, Darmstadt (DE)

(72) Inventors: Amir Hossain Parham, Frankfurt Am Main (DE); Tobias Grossmann, Darmstadt (DE); Anja Jatsch, Frankfurt am Main (DE); Thomas Eberle, Landau (DE); Jonas Kroeber, Frankfurt am Main (DE); Christof Pflumm, Darmstadt (DE); Lars Dobelmann-Mara, Darmstadt (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 16/434,397

(22) Filed: Jun. 7, 2019

(65) Prior Publication Data

US 2019/0372020 A1    Dec. 5, 2019

Related U.S. Application Data

(62) Division of application No. 15/307,617, filed as application No. PCT/EP2015/000680 on Mar. 30, 2015, now Pat. No. 10,355,223.

(30) Foreign Application Priority Data

Apr. 30, 2014  (EP) .................................... 14001525

(51) Int. Cl.
| | | |
|---|---|---|
| *H01L 51/00* | (2006.01) | |
| *C07D 405/14* | (2006.01) | |
| *C07D 409/14* | (2006.01) | |
| *C07D 471/04* | (2006.01) | |
| *C07D 487/04* | (2006.01) | |
| *C07D 491/048* | (2006.01) | |
| *C09B 57/00* | (2006.01) | |
| *A61B 18/20* | (2006.01) | |
| *C09K 11/02* | (2006.01) | |
| *A61N 5/06* | (2006.01) | |
| *H01L 51/50* | (2006.01) | |

(52) U.S. Cl.
CPC ........ *H01L 51/0072* (2013.01); *A61B 18/203* (2013.01); *A61N 5/0616* (2013.01); *C07D 405/14* (2013.01); *C07D 409/14* (2013.01); *C07D 471/04* (2013.01); *C07D 487/04* (2013.01); *C07D 491/048* (2013.01); *C09B 57/00* (2013.01); *C09K 11/025* (2013.01); *H01L 51/0067* (2013.01); *H01L 51/0071* (2013.01); *H01L 51/0073* (2013.01); *H01L 51/0074* (2013.01); *H01L 51/0003* (2013.01); *H01L 51/0085* (2013.01); *H01L 51/0087* (2013.01); *H01L 51/5016* (2013.01); *H01L 51/5072* (2013.01); *Y02E 10/549* (2013.01); *Y02P 70/50* (2015.11)

(58) Field of Classification Search
CPC ............. H01L 51/0072; H01L 51/5072; H01L 51/5016; H01L 51/0087; H01L 51/0085; H01L 51/0003; H01L 51/5012; H01L 51/0069; H01L 51/0068; H01L 51/0065; H01L 51/0073; H01L 51/0071; H01L 51/0074; H01L 51/0067; A61N 5/0616; A61B 18/203; C09B 57/00; Y02P 70/521; Y02E 10/549; C09K 2211/1088; C09K 2211/1092; C09K 2211/1029; C09K 2211/1037; C09K 2211/1044; C09K 2211/1033; C09K 2211/1059; C09K 11/06; C09K 11/025; C07D 491/048; C07D 487/04; C07D 471/04; C07D 513/04; C07D 498/04; C07D 495/04; C07D 491/056; C07D 491/052; C07D 487/14; C07D 471/22; C07D 471/14; C07D 409/14; C07D 405/14; C07K 2211/1088

See application file for complete search history.

(56) References Cited

U.S. PATENT DOCUMENTS

| | | | |
|---|---|---|---|
| 6,866,678 B2 * | 3/2005 | Shenderova ......... | A61N 5/0616 128/898 |
| 7,294,849 B2 | 11/2007 | Thompson et al. | |
| 9,334,260 B2 | 5/2016 | Parham et al. | |
| 2011/0006670 A1 | 1/2011 | Katakura et al. | |
| 2012/0223276 A1 | 9/2012 | Parham et al. | |
| 2015/0207082 A1 | 7/2015 | Dyatkin et al. | |
| 2015/0214489 A1 | 7/2015 | Parham et al. | |
| 2018/0037546 A1* | 2/2018 | Sugino ................... | H01L 51/50 |

FOREIGN PATENT DOCUMENTS

| | | |
|---|---|---|
| CN | 102770427 A | 11/2012 |
| CN | 103517906 A | 1/2014 |
| JP | 2013510803 A | 3/2013 |
| JP | 2013526014 A | 6/2013 |
| JP | 2013131518 A | 7/2013 |
| JP | 2013538440 A | 10/2013 |

(Continued)

OTHER PUBLICATIONS

WO 2015/083430 A1; (2015) Proquest English machine translation p. 1-65.*

(Continued)

*Primary Examiner* — John M Mauro
(74) *Attorney, Agent, or Firm* — Faegre Drinker Biddle & Reath LLP

(57) ABSTRACT

The application relates to compounds having functional substituents in a specific spatial arrangement, to devices comprising same, and to the preparation and use thereof.

18 Claims, No Drawings

(56) References Cited

FOREIGN PATENT DOCUMENTS

| WO | WO-2011057706 A2 | 5/2011 |
| WO | WO-2011126224 A1 | 10/2011 |
| WO | WO-2012004765 A2 | 1/2012 |
| WO | WO-2012036482 A1 | 3/2012 |
| WO | WO-2012130709 A1 | 10/2012 |
| WO | WO-2014009317 A1 | 1/2014 |
| WO | WO-2014015931 A1 | 1/2014 |
| WO | WO-2015083430 A1 | 6/2015 |

OTHER PUBLICATIONS

International Search Report for PCT/EP2015/000680 dated Jun. 18, 2015.
Japanese Office Action for Application No. 2016-565420 dated Dec. 4, 2018.
JP 2013-131518A WIPO English Machine Translation; pp. 1-90.
WO-2015083430-A1 English Machine Translation ProQuest Dialog; pp. 1-62; 2017.

* cited by examiner

MATERIALS FOR ELECTRONIC DEVICES

CROSS-REFERENCE TO RELATED APPLICATIONS

This application is a divisional application of U.S. application Ser. No. 15/307,617 filed Oct. 28, 2018. U.S. application Ser. No. 15/307,617 is the national stage application (under 35 U.S.C. § 371) of PCT/EP2015/000,680, filed Mar. 30, 2015, which claims benefit of European Application No. 14001525.6, filed Apr. 30, 2014, all of which are incorporated herein by reference in their entirety.

The present invention relates to cyclic compounds having a specific arrangement of electron-conducting and hole-conducting groups, to the use thereof in electronic devices, to the preparation thereof, and to electronic devices.

The structure of organic electroluminescent devices (for example OLEDs—organic light-emitting diodes, or OLECs—organic light-emitting electrochemical cells) in which organic semiconductors are employed as functional materials is described, for example, in U.S. Pat. Nos. 4,539,507, 5,151,629, EP 0676461 and WO 98/27136. The emitting materials employed here, besides fluorescent emitters, are increasingly organometallic complexes which exhibit phosphorescence (M. A. Baldo et al., Appl. Phys. Lett. 1999, 75, 4-6). For quantum-mechanical reasons, an up to fourfold increase in energy and power efficiency is possible using organometallic compounds as phosphorescence emitters. In general, there is still a need for improvement, in particular with respect to efficiency, operating voltage and lifetime, both in the case of OLEDs which exhibit singlet emission and also in the case of OLEDs which exhibit triplet emission. This applies, in particular, to OLEDs which emit in the relatively short-wave region, i.e. green and in particular blue.

The properties of organic electroluminescent devices are not determined only by the emitters employed. In particular, the other materials used, such as host and matrix materials, hole-blocking materials, electron-transport materials, hole-transport materials and electron- or exciton-blocking materials, are also of particular importance here. Improvements in these materials can result in significant improvements in electroluminescent devices.

In accordance with the prior art, use is made, inter alia, of ketones (for example in accordance with WO 2004/093207 or WO 2010/006680) or phosphine oxides (for example in accordance with WO 2005/003253) as matrix materials for phosphorescent emitters. Further matrix materials in accordance with the prior art are triazines (for example WO 2008/056746, EP 0906947, EP 0908787, EP 0906948).

For fluorescent OLEDs, use is made in accordance with the prior art of, in particular, condensed aromatic compounds, in particular anthracene derivatives, as host materials, in particular for blue-emitting electroluminescent devices, for example 9,10-bis(2-naphthyl)-anthracene (U.S. Pat. No. 5,935,721). WO 03/095445 and CN 1362464 disclose 9,10-bis(1-naphthyl)-anthracene derivatives for use in OLEDs. Further anthracene derivatives are disclosed in WO 01/076323, WO 01/021729, WO 2004/013073, WO 2004/018588, WO 2003/087023 or WO 2004/018587. Host materials based on aryl-substituted pyrenes and chrysenes are disclosed in WO 2004/016575. Host materials based on benzanthracene derivatives are disclosed in WO 2008/145239. For high-quality applications, it is desirable to have improved host materials available.

The prior art discloses the use of compounds containing one or more carbazole groups in electronic devices, for example in WO 2005/039246, US 2005/0069729, JP 2004/288381, EP 1205527 or WO 2008/086851.

The prior art furthermore discloses the use of compounds containing one or more indenocarbazole groups in electronic devices, for example in WO 2010/136109 and WO 2011/000455.

The prior art furthermore discloses the use of compounds containing one or more electron-deficient heteroaromatic six-membered rings in electronic devices, for example in WO 2010/015306, WO 2007/063754 and WO 2008/056746.

WO 2009/069442 discloses tricyclic compounds, such as carbazole, dibenzofuran or dibenzothiophene, which are highly substituted by electron-deficient heteroaromatic groups (for example pyridine, pyrimidine or triazine). The tricyclic compounds are not substituted by hole-conducting groups, i.e. electron-rich groups.

JP 2009-21336 discloses substituted dibenzofurans which are substituted by carbazole in the 2 position and by a triazine in the 8 position.

WO 2011/057706 discloses dibenzothiophenes and dibenzofurans, some of which are substituted, as matrix materials, where the compounds are substituted in a specific manner by an electron-conducting group and by a hole-conducting group.

However, there is still a need for improvement on use of these materials as in the case of other materials, in particular with respect to the efficiency and the lifetime of the device.

The object of the present invention is therefore the provision of compounds which are suitable for use in a fluorescent or phosphorescent OLED, for example as host material and/or matrix material or as hole-transport/electron-blocking material or exciton-blocking material or as electron-transport or hole-blocking material, and which result in good device properties when used in an OLED, and the provision of the corresponding electronic device.

Surprisingly, it has been found that certain compounds described in greater detail below achieve these objects and result in good properties of the organic electroluminescent device, in particular with respect to the lifetime, the efficiency and the operating voltage. The present invention therefore relates to electronic devices, in particular organic electroluminescent devices, which comprise compounds of this type, and to the corresponding preferred compounds. The surprising effects are achieved by a specific arrangement of electron-conducting and hole-conducting groups in compounds of the formulae shown below.

The compounds according to the invention are furthermore distinguished by high temperature stability, enabling them to be evaporated in a high vacuum without decomposition. This property is a basic prerequisite for the reproducible production of organic electronic devices, such as organic electroluminescent devices, and has, in particular, a positive effect on the operating lifetime.

The compounds according to the invention also have a high glass transition temperature (To), which is advantageous with respect to the processing of the compounds in the production of electronic devices. The high glass-transition temperature of the compounds also allows the use of the compounds in thin amorphous organic layers.

Furthermore, the compounds according to the invention allow stabilisation of the charge carriers in the excited state and have a sufficiently high triplet energy, which represents an important prerequisite for phosphorescent devices. Furthermore, the compounds according to the invention exhibit improved performance data in OLEDs compared with the compounds from the prior art.

The compounds according to the invention are also distinguished by improved redox stability in solution compared with compounds known from the prior art. This simplifies purification of the compounds, simplifies their handling and improves their storage stability in solutions which are prepared for the production of organic electronic devices from solution with the aid of printing processes.

Finally, the compounds according to the invention are distinguished by very good solubility, enabling the compounds also to be processed from solution. Inexpensive production of organic electronic devices is thus accomplished. The compounds according to the invention are therefore also suitable for the mass production of organic electronic devices.

The present invention relates to a compound of the general formula (1)

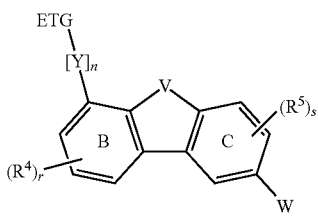

formula (1)

where the following applies to the symbols and indices used:

ETG is an organic electron-transporting group from the group of the electron-deficient heteroaromatic groups, where the ETG preferably a heteroaryl group having 5 to 60 aromatic ring atoms, where very preferred heteroatoms are N-atoms and very particularly preferred ETGs are selected from the group of the triazines, pyrimidines, pyrazines, pyridines, quinazolines, benzimidazoles, quinolines, isoquinolines and naphthyridines and especially preferred ETGs are selected from the group of the triazines, pyrimidines, pyrazines and pyridines; the ETG may be substituted by one or more radicals $R^1$, which may be identical or different on each occurrence;

W is an electron-rich organic group which conducts holes, where W is preferably selected from the group of the arylamines, triarylamines, bridged amines, where preferred bridged amines here are dihydroacridines, dihydrophenazines, phenoxazines and phenothiazines, carbazoles, bridged carbazoles, biscarbazoles, benzocarbazoles, indenocarbazoles and indolocarbazoles; W may be substituted by one or more radicals $R^1$, which may be identical or different on each occurrence;

V is O or S, preferably O;

Y is a divalent bridge; Y preferably represents an aromatic or heteroaromatic ring system having 5 to 60 ring atoms; the divalent bridge Y very preferably has 5 to 30 ring atoms, particularly preferably 5 to 18 ring atoms, very preferably 5 to 12 ring atoms, especially 5 to 10 aromatic ring atoms, more preferably the bridge has precisely 6 ring atoms and most preferably the bridge is a phenylene bridge;

n is either 0 or 1, preferably 0, where n equals 0 means that the ETG and the ring B are linked directly to one another by a single bond;

r is an integer from 0, 1, 2 or 3, preferably 0 or 1 and very preferably 0;

s is an integer from 0, 1, 2 or 3, preferably 0 or 1 and very preferably 0;

$R^1$ is, identically or differently on each occurrence, H, D, F, Cl, Br, I, $N(R^2)_2$, CN, $NO_2$, $Si(R^2)_3$, $B(OR^2)_2$, $C(=O)R^2$, $P(=O)(R^2)_2$, $S(=O)R^2$, $S(=O)_2R^2$, $OSO_2R^2$, a straight-chain alkyl, alkoxy or thioalkoxy group having 1 to 40 C atoms or a straight-chain alkenyl or alkynyl group having 2 to 40 C atoms or a branched or cyclic alkyl, alkenyl, alkynyl, alkoxy, alkylalkoxy or thioalkoxy group having 3 to 40 C atoms, each of which may be substituted by one or more radicals $R^2$, where one or more non-adjacent $CH_2$ groups may be replaced by $R^2C=CR^2$, C≡C, $Si(R^2)_2$, $Ge(R^2)_2$, $Sn(R^2)_2$, C=O, C=S, C=Se, $C=NR^2$, $P(=O)(R^2)$, SO, $SO_2$, $NR^2$, O, S or $CONR^2$ and where one or more H atoms may be replaced by D, F, Cl, Br, I, CN or $NO_2$, or an aromatic or heteroaromatic ring system having 5 to 60 aromatic ring atoms, which may in each case be substituted by one or more radicals $R^2$, or an aryloxy, arylalkoxy or heteroaryloxy group having 5 to 60 aromatic ring atoms, which may be substituted by one or more radicals $R^2$, or a diarylamino group, diheteroarylamino group or arylheteroarylamino group having 10 to 40 aromatic ring atoms, which may be substituted by one or more radicals $R^2$, or a combination of two or more of these groups or a crosslinkable group Q; two or more adjacent radicals $R^1$ here may form a mono- or polycyclic, aliphatic or aromatic ring system with one another;

$R^2$ is, identically or differently on each occurrence, H, D, F, Cl, Br, I, $N(R^3)_2$, CN, $NO_2$, $Si(R^3)_3$, $B(OR^3)_2$, $C(=O)R^3$, $P(=O)(R^3)_2$, $S(=O)R^3$, $S(=O)_2R^3$, $OSO_2R^3$, a straight-chain alkyl, alkoxy or thioalkoxy group having 1 to 40 C atoms or a straight-chain alkenyl or alkynyl group having 2 to 40 C atoms or a branched or cyclic alkyl, alkenyl, alkynyl, alkoxy, alkylalkoxy or thioalkoxy group having 3 to 40 C atoms, each of which may be substituted by one or more radicals $R^3$, where one or more non-adjacent $CH_2$ groups may be replaced by $R^3C=CR^3$, C≡C, $Si(R^3)_2$, $Ge(R^3)_2$, $Sn(R^3)_2$, C=O, C=S, C=Se, $C=NR^3$, $P(=O)(R^3)$, SO, $SO_2$, $NR^3$, O, S or $CONR^3$ and where one or more H atoms may be replaced by D, F, Cl, Br, I, CN or $NO_2$, or an aromatic or heteroaromatic ring system having 5 to 60 aromatic ring atoms, which may in each case be substituted by one or more radicals $R^3$, or an aryloxy, arylalkoxy or heteroaryloxy group having 5 to 60 aromatic ring atoms, which may be substituted by one or more radicals $R^3$, or a diarylamino group, diheteroarylamino group or arytheteroarylamino group having 10 to 40 aromatic ring atoms, which may be substituted by one or more radicals $R^3$, or a combination of two or more of these groups; two or more adjacent radicals $R^2$ here may form a mono- or polycyclic, aliphatic or aromatic ring system with one another;

$R^3$ is, identically or differently on each occurrence, H, D, F or an aliphatic, aromatic and/or heteroaromatic hydrocarbon radical having 1 to 20 C atoms, in which, in addition, one or more H atoms may be replaced by F; two or more substituents $R^3$ here may also form a mono- or polycyclic, aliphatic or aromatic ring system with one another;

$R^4$, $R^5$ are, identically or differently on each occurrence, H, D, F, Cl, Br, I, $N(R^2)_2$, CN, $NO_2$, $Si(R^2)_3$, $B(OR^2)_2$, $C(=O)R^2$, $P(=O)(R^2)_2$, $S(=O)R^2$, $S(=O)_2R^2$, $OSO_2R^2$, a straight-chain alkyl, alkoxy or thioalkoxy group having 1 to 40 C atoms or a straight-chain alkenyl or alkynyl group having 2 to 40 C atoms or a branched or cyclic alkyl, alkenyl, alkynyl, alkoxy, alkylalkoxy or thioalkoxy group having 3 to 40 C atoms.

In a further preferred embodiment of the present invention, V in the compound of the formula (1) is equal to S.

Preferred electron-deficient heteroaromatic groups as ETG here are selected from the following groups:

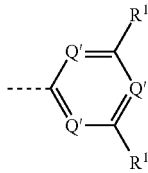
formula (E-1)

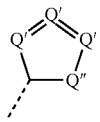
formula (E-2)

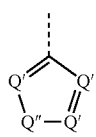
formula (E-3)

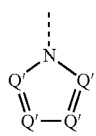
formula (E-4)

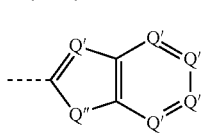
formula (E-5)

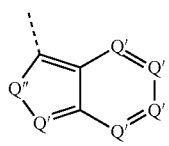
formula (E-6)

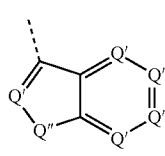
formula (E-7)

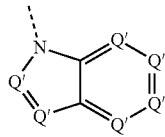
formula (E-8)

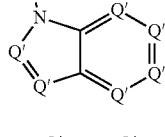
formula (E-9)

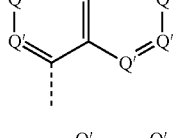
formula (E-10)

where the dashed bond marks the bonding position, $R^1$ is as defined above and
Q' represents on each occurrence, identically or differently, $CR^1$ or N, and
Q'' represents $NR^1$, O or S;
where at least one Q' is equal to N and/or at least one Q'' is equal to $NR^1$.

Preferred electron-deficient heteroaromatic groups as ETG are: pyridines, pyrazines, pyrimidines, pyridazines, 1,2,4-triazines, 1,3,5-triazines, quinolines, isoquinolines, quinoxalines, pyrazoles, imidazoles, benzimidazoles, thiazoles, benzothiazoles, oxazoles or benzoxazoles, each of which may be substituted by $R^1$. The electron-transporting group is even more preferably a pyridine, pyrazine, pyrimidine, pyridazine or 1,3,5-triazine which is substituted by one or more radicals $R^1$.

The compound of the formula (1) containing the electron-transport group preferably has an LUMO (lowest unoccupied molecular orbital) energy which is lower than −1.3 eV, very preferably lower than −2.5 eV and very particularly preferably lower than −2.7 eV.

HOMO (highest occupied molecular orbital) and LUMO (lowest unoccupied molecular orbital) energy levels and the energy of the lowest triplet state $T_1$ or that of the lowest excited singlet state $S_1$ of the materials are determined via quantum-chemical calculations. To this end, the "Gaussian09 W" (Gaussian Inc.) software package is used here. For the calculation of organic substances, firstly a geometry optimisation is carried out using the "Ground State/Semi-empirical/Default Spin/AM1/Charge 0/Spin Singlet" method. An energy calculation is subsequently carried out on the basis of the optimised geometry. The "TD-SCF/DFT/Default Spin/B3PW91" method with the "6-31G(d)" base set (charge 0, spin singlet) is used here. The energy calculation gives the HOMO energy level HEh or LUMO energy level LEh in hartree units. The HOMO and LUMO energy levels calibrated with reference to cyclic voltammetry measurements in electron volts are determined therefrom as follows:

$$HOMO(eV)=((HEh*27.212)-0.9899)/1.1206$$

$$LUMO(eV)=((LEh*27.212)-2.0041)/1.385$$

For the purposes of this application, these values are to be regarded as HOMO or LUMO energy levels of the materials.

The lowest triplet state $T_1$ is defined as the energy of the triplet state having the lowest energy which arises from the quantum-chemical calculation described.

The lowest excited singlet state $S_1$ is defined as the energy of the excited singlet state having the lowest energy which arises from the quantum-chemical calculation described.

The compound of the formula (1) furthermore preferably has an electron mobility $\mu_-$ of $10^{-6}$ cm$^2$/(Vs) or more, very preferably $10^{-5}$ cm$^2$/(Vs) or more and very particularly preferably $10^{-4}$ cm$^2$/(Vs) or more.

In the compounds of the formula (1), the LUMO is preferably localised on the electron-transport group, where a residence probability of 0.9 is assumed for the orbitals. The LUMO is very preferably more than 80% localised on the electron-transport group, more preferably the LUMO is not localised at all on the group W (for example a carbazole group). It is especially preferred if the HOMO and the LUMO of the compound according to the invention do not overlap at all. The person skilled in the art will have no difficulties at all in determining the overlap of the orbitals.

The overlap of the molecular orbitals which are involved in certain electronic transitions (charge-transfer states) is described with the aid of the parameter Λ. The meaning of the parameter Λ is well known to the person skilled in the art here. Determination of the parameter by means of methods described in the prior art presents the person skilled in the art with absolutely no difficulties. For the purposes of the present invention, the parameter Λ is determined using the PBHT method as described by D. J. Tozer et al. (J. Chem. Phys. 128, 044118 (2008)), which is implemented, for example, in the Q-Chem 4.1 software package from Q-Chem, Inc. The molecular orbitals are calculated here by the method described above. The spatial overlaps for all possible pairs of occupied molecular orbitals, $\varphi_i$, and unoccupied (virtual) molecular orbitals, $\varphi_a$, are subsequently determined from the following equation:

$$O_{ia} = \langle |\varphi_i| \| |\varphi_a| \rangle$$

where the moduli of the orbitals are used for the calculation.

The parameter Λ then arises from the weighted sum over all pairs is of occupied and unoccupied molecular orbitals in accordance with $$\Lambda = \frac{\sum_{ia} \kappa_{ia}^2 O_{ia}}{\sum_{ia} \kappa_{ia}^2}$$

where the value of $\kappa_{ia}$ is determined by the method of Tozer et al. from the orbital coefficients in the excitation vectors of the resolved TD (time-dependent) eigenvalue equation and where $0 \leq \Lambda \leq 1$.

In a preferred embodiment, the present invention relates to a compound of the general formula (1) having a small spatial overlap of the molecular orbitals Λ which are involved in certain electronic transitions (charge-transfer states).

In the present application, a small overlap of the molecular orbitals means that the value of the parameter Λ is 0.3 or less, preferably 0.2 or less, very preferably 0.15 or less, very particularly preferably 0.1 or less and especially preferably 0.05 or less.

The compound of the formula (1) containing the hole-transport group W preferably has an HOMO energy (HOMO$_w$) which is in the region of the electron work function of the anode used ($\phi_{anode}$) plus+1.5 eV or less, i.e.:

$$HOMO_w \leq (\phi_{anode} + 1.5\ eV)$$

If the anode used has an electron work function of −5 eV, the HOMO energy of the compound of the formula (1) is −3.5 eV or lower (i.e. more negative than −3.5 eV). The compound of the formula (1) very preferably has an HOMO energy which is equal to the electron work function of the anode or lower, very particularly preferably lower.

The compound of the formula (1) is furthermore preferably characterised in that the hole mobility $\mu_+$ is $10^{-6}$ cm$^2$/(Vs) or more, very preferably $10^{-5}$ cm$^2$/(Vs) or more and very particularly preferably $10^{-4}$ cm$^2$/(Vs) or more.

The measurement of electron and hole mobilities is routinely carried out by the person skilled in the art by means of standard methods.

In the compounds of the formula (1), the HOMO will be substantially localised on the hole-transport group W. Substantially here means that the HOMO is 80% or more localised on the hole-conducting group or is not localised on the electron-deficient electron-transport group, where a residence probability of 0.9 is assumed for the orbitals.

For the purposes of the present invention, preference is given to a compound of the general formula (2),

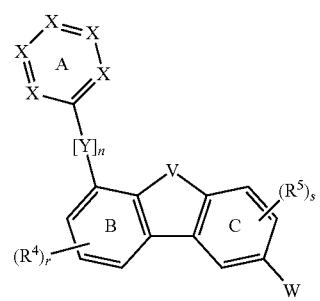

formula (2)

where the above definitions apply to the symbols and indices used and furthermore:

X is N or CR$^1$, where at least one of the five groups X in ring A represents an N atom, preferably two of the five groups X in ring A are equal to N and very preferably three of the five groups X in ring A are equal to N, and the ring A is very particularly preferably a triazine, especially preferably a 1,3,5-triazine;

W is a group of the formula (W-1)

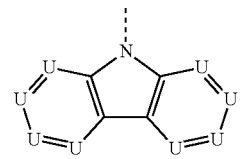

formula (W-1)

U is N or CR$^1$, preferably CR$^1$, where the dotted line denotes the bond from the group W to the ring C in formula (2).

In a preferred embodiment, two or more adjacent radicals R$^1$ of the groups U=CR$^1$ may form a mono- or polycyclic, aliphatic or aromatic ring system with one another.

In a further preferred embodiment, two or more adjacent radicals R$^1$ of the groups U=CR$^1$ cannot form a mono- or polycyclic, aliphatic or aromatic ring system with one another.

It is furthermore preferred if at least one of the radicals R$^1$ from the groups U=CR$^1$ is not equal to H.

It is very preferred for the purposes of the present invention if R$^1$ as a group U=CR$^1$ represents H or an aromatic or heteroaromatic ring system having 5 to 60 aromatic ring atoms, which may in each case be substituted by one or more radicals R$^2$, where it is particularly preferred if at least one of the radicals R$^1$ from U=CR$^1$ is not equal to H.

It is particularly preferred if R$^1$ in each case represents H or an aromatic or heteroaromatic ring system having 5 to 60 aromatic ring atoms, which may in each case be substituted by one or more radicals R$^2$, where it is particularly preferred if at least one of the radicals R$^1$ is not equal to H.

It is preferred if the compound has the general formula (1) and r is either 0 or 1 and s is either 0 or 1. Preferably, either only r or only s is equal to 1 and the respective other parameter is equal to 0, very preferably both r and s are equal to 0.

In a further preferred embodiment of the present invention, n is always equal to 1, so that a divalent bridge is always present between ring A and ring B.

It is furthermore preferred if the compound has the general formula (4), where the above definitions apply to the indices and symbols used and the preferred embodiments thereof mentioned elsewhere in the present invention also represent preferred embodiments of compounds of the formula (4),

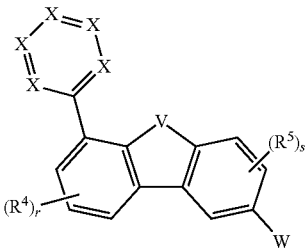

formula (4)

where the above definitions apply to the symbols and indices used and where r is either 0 or 1 and where s is either 0 or 1.

It is furthermore preferred if r+s=1.

It is also preferred if the compound has the general formula (6), where the above definitions apply to the indices and symbols used and the preferred embodiments thereof mentioned elsewhere in the present invention also represent preferred embodiments of compounds of the formula (6),

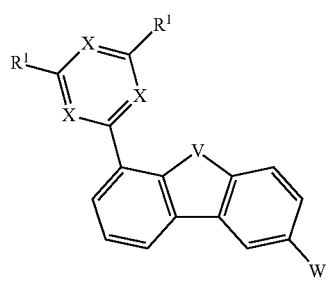

formula (6)

It is more preferred if the compound has the general formula (7), where the above definitions apply to the indices and symbols used and the preferred embodiments thereof mentioned elsewhere in the present invention also represent preferred embodiments of compounds of the formula (7),

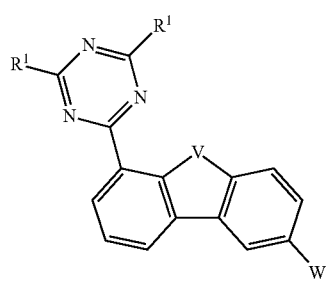

formula (7)

It is preferred if the group W is a carbazole, an indenocarbazole or an indolocarbazole, where the groups may be substituted as disclosed herein.

In a preferred embodiment of the present invention, the group W is a carbazole, which may be substituted by one or more radicals $R^1$, which may be identical or different on each occurrence, where adjacent radicals $R^1$ cannot form a ring closure with one another.

It is very preferred if the group W is an indenocarbazole which is substituted by one or more radicals $R^1$ or $R^2$, which may be identical or different on each occurrence.

It is furthermore very preferred if the group W is an indolocarbazole which is substituted by one or more radicals $R^1$ or $R^2$, which may be identical or different on each occurrence.

A group W of the following formula (W-2) is particularly preferred:

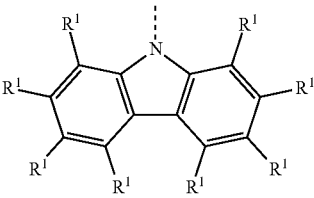

formula (W-2)

Very particular preference is given to a group W of the formula (W-3),

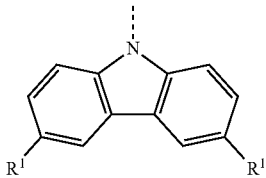

formula (W-3)

Especial preference is given to a group W of the formula (W-4),

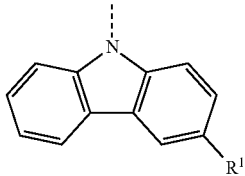

formula (W-4)

It is more preferred if the group W has the formula (W-4) and the radical $R^1$ occurring therein is not equal to hydrogen, where it is more preferred if $R^1$ in formula (W-4) is an aromatic or heteroaromatic ring system having 5 to 60 aromatic ring atoms, which may in each case be substituted by one or more radicals $R^2$.

In another very preferred embodiment of the present invention, the group W has the formula (W-4), where $R^1$ is also equal to H.

It is particularly preferred if the group W is a group of the formula (W-5),

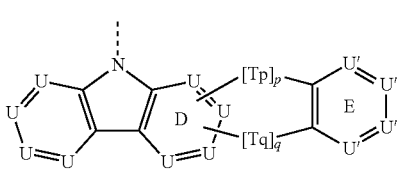

formula (W-5)

where the above definitions apply to the indices and symbols used and where furthermore:

Tp, Tq are, identically or differently, a divalent bridge; Tp and Tq are preferably selected from $N(R^2)$, $B(R^2)$, O, $C(R^2)_2$, $Si(R^2)_2$, C=O, C=NR$^2$, C=C(R$^2$)$_2$, S, S=O, SO$_2$, P(R$^2$) and P(=O)R$^2$; N(R$^2$), O, C(R$^2$)$_2$ and S are very preferred here and N(R$^2$) and C(R$^2$)$_2$ are especially preferred;

U' is, identically or differently on each occurrence, CR$^2$ or N, preferably CR$^2$;

p is 0 or 1; where p equals 0 means that the ring E and the ring D are linked by a single bond;

q is 0 or 1; where q equals 0 means that the ring E and the ring D are linked by a single bond;

and where p+q=1 or 2 and is preferably equal to 1;

and where Tp and Tq are each bonded to adjacent groups U of the ring D in any possible orientation; and where furthermore each group U which is bonded to Tp or Tq represents a carbon atom.

Very particularly preferred groups W are selected from the following groups of the formulae (W-6) to (W-8), where that of the formula (W-7) is especially preferred:

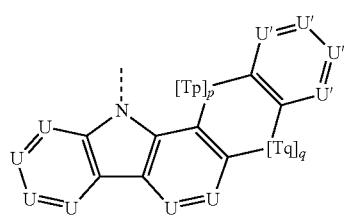

formula (W-6)

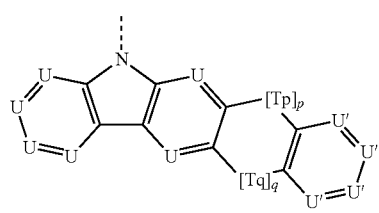

formula (W-7)

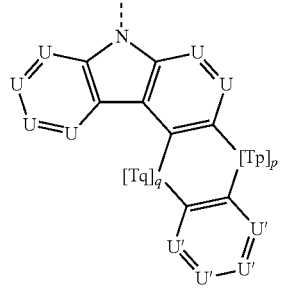

formula (W-8)

Especially preferred groups W are those of the formulae (W-9) to (W-14),

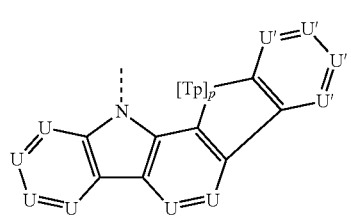

formula (W-9)

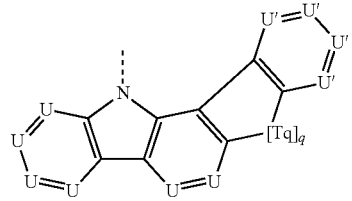

formula (W-10)

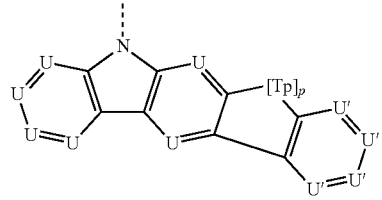

formula (W-11)

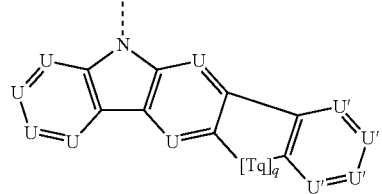

formula (W-12)

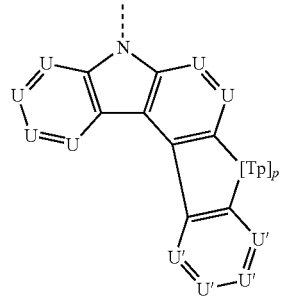

formula (W-13)

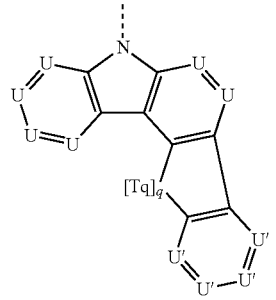

formula (W-14)

In a preferred embodiment of the present invention, the group W is an indenocarbazole, which very preferably has one of the following formulae (W-15) to (W-20):

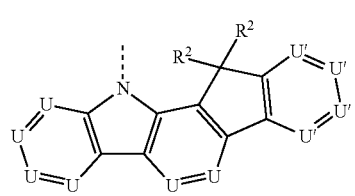

formula (W-15)

formula (W-16)

formula (W-17)

formula (W-18)

formula (W-19)

formula (W-20)

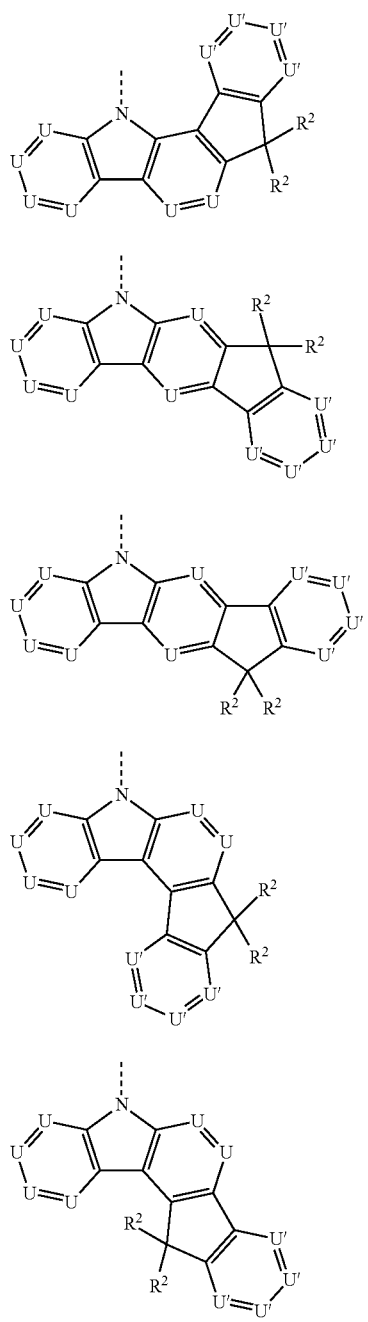

formula (W-21)

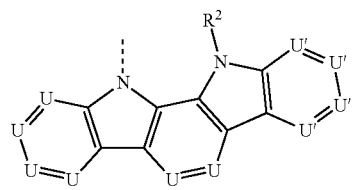

formula (W-22)

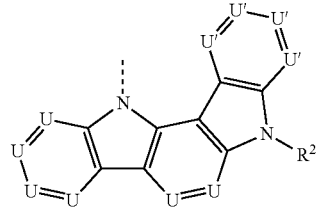

formula (W-23)

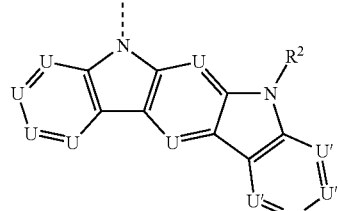

formula (W-24)

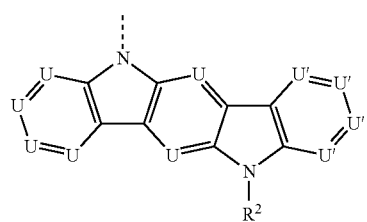

formula (W-25)

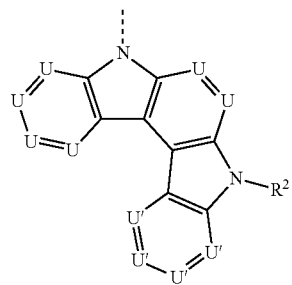

formula (W-26)

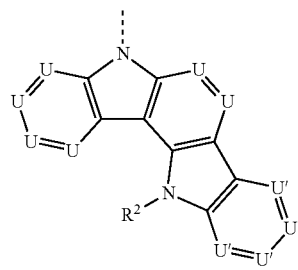

where the indenocarbazoles of the formulae (W-17), (W-18), (W-19), (W-15) and (W-16) are very particularly preferred. Especial preference is given to the indenocarbazoles of the formulae (W-17), (W-18) and (W-19), more preferably those of the formulae (W-17) and (W-18) and most preferably those of the formula (W-17).

In a further preferred embodiment of the present invention, the group W is an indolocarbazole, which very preferably has one of the following formulae (W-21) to (W-25):

where the indolocarbazoles of the formulae (W-21), (W-23) and (W-24) are very particularly preferred. Especially preferred indolocarbazoles are those of the formulae (W-21) and (W-23), where those of the formula (W-21) are most preferred.

It is very preferred for the purposes of the present invention if U in the groups of the formulae (W-1) and (W-5) to (W-26) is always equal to CR¹, it is particularly preferred if the radicals R¹ belonging to the groups U=CR¹ are always H here.

It is also very preferred for the purposes of the present invention if U' in the groups of the formulae (W-5) to (W-26) is always equal to CR², it is particularly preferred if the radicals R² belonging to the groups U'=CR² are always H here.

It is particularly preferred if, in the groups of the formulae (W-5) to (W-26), U is equal to CR¹ and U' is equal to CR², and the radicals R¹ belonging to the groups U=CR¹ and the radicals R² belonging to the groups U'=CR² are very particularly preferably equal to H.

In a further preferred embodiment, the present invention relates to a compound of the formula (1), where W is defined as indicated in formula (W-27), formula (W-27)

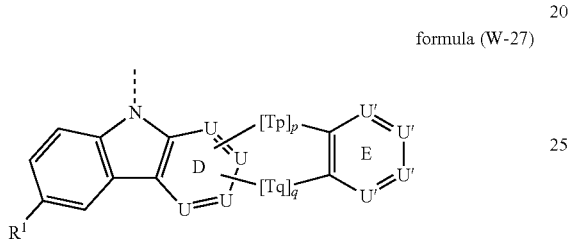

where the above definitions apply to the indices and symbols used and the preferred embodiments thereof mentioned elsewhere in the present invention also represent preferred embodiments of the group of the formula (W-27).

As already explained, the groups X of the ring A of the compound of the formula (2) can be N or CR¹, where at least one of the five groups X in ring A represents an N atom, preferably two of the five groups X in ring A are equal to N and very preferably three of the five groups X in ring A are equal to N.

Preferred groups for the ring A in formula (2) of the formula (A-1), formula (A-1)

are those of the following formulae (A-2) to (A-13), where the dotted line denotes the bond between the ring A and Y in formula (2) or, if n is equal to 0, between the ring A and the ring B in formula (2):

formula (A-2)

formula (A-3)

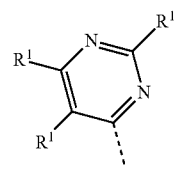

formula (A-4)

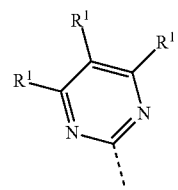

formula (A-5)

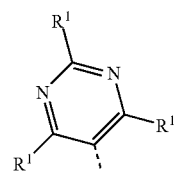

formula (A-6)

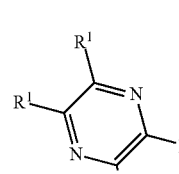

formula (A-7)

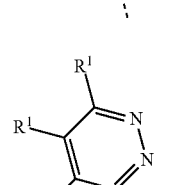

formula (A-8)

formula (A-9)

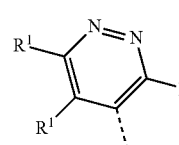

formula (A-10)

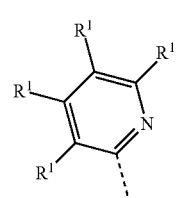

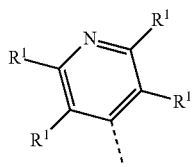

formula (A-11)

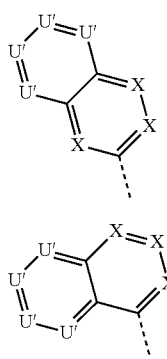

formula (A-12)

formula (A-13)

where the above definitions and preferred embodiments apply to the symbols and indices used.

Particular preference is given here to the group of the formula (A-2).

A further preferred group for the ring A in formula (2) is the following group of the formula (A-14):

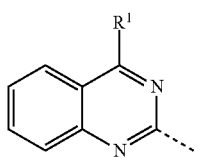

formula (A-14)

Very preferred groups for the ring A in formula (2) of the formula (A-1) are those of the formulae (A-2) to (A-11) where $R^1$ is equal to $Ar^1$, where $Ar^1$ is on each occurrence, identically or differently, an aromatic or heteroaromatic ring system having 5 to 60 aromatic ring atoms, which may in each case be substituted by one or more radicals $R^2$; $Ar^1$ is preferably on each occurrence, identically or differently, a phenyl, biphenyl, terphenyl, quaterphenyl, dibenzofuranyl, dibenzothiophenyl, fluorenyl, spirobifluorenyl, pyridyl or pyrimidyl group, each of which may be substituted by one or more radicals $R^2$; $Ar^1$ is very preferably on each occurrence, identically or differently, a phenyl, biphenyl, terphenyl or quater-phenyl group, each of which may be substituted by one or more radicals $R^2$; particular preference is given to a phenyl group, which may in each case be substituted by one or more radicals $R^2$, where it is especially preferred if the phenyl group is in unsubstituted form.

Very particular preference is given here to the group of the formula (A-2) where $R^1$ is equal to $Ar^1$.

A further very preferred group for the ring A in formula (2) is the group of the formula (A-14) where $R^1$ is equal to $Ar^1$.

Particularly preferred groups $Ar^1$ are also the following groups having the formulae (Ar-1) to (Ar-24), where the groups may be substituted by one or more radicals $R^2$, which may be identical or different on each occurrence. Very particularly preferred groups $Ar^1$ are those of the formulae (Ar-1) to (Ar-9),

formula (Ar-1)

formula (Ar-2)

formula (Ar-3)

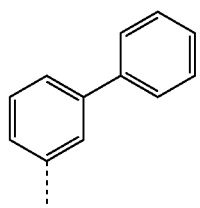

formula (Ar-4)

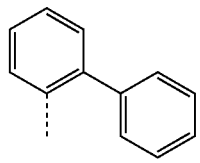

formula (Ar-6)

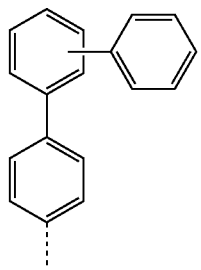

formula (Ar-7)

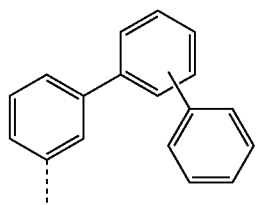

formula (Ar-8)

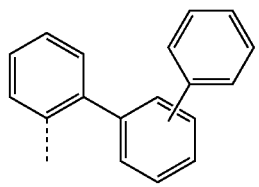

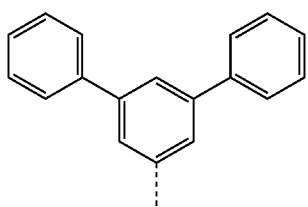
formula (Ar-9)

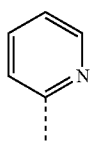
formula (Ar-10)

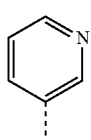
formula (Ar-11)

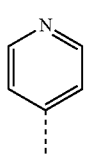
formula (Ar-12)

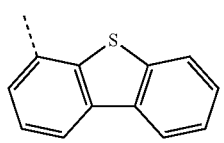
formula (Ar-13)

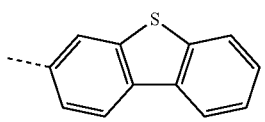
formula (Ar-14)

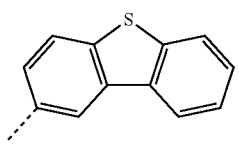
formula (Ar-15)

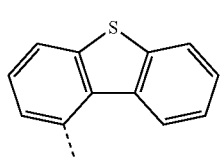
formula (Ar-16)

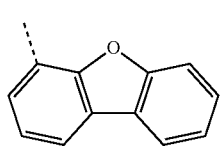
formula (Ar-17)

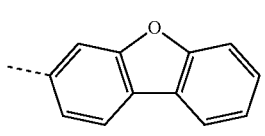
formula (Ar-18)

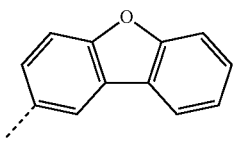
formula (Ar-19)

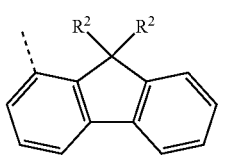
formula (Ar-20)

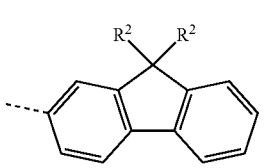
formula (Ar-21)

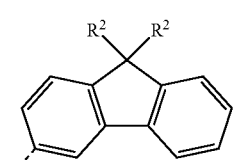
formula (Ar-22)

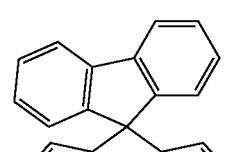
formula (Ar-23)

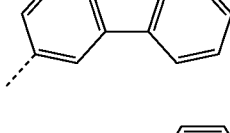
formula (Ar-24)

The formulation that two or more radicals may form a ring with one another is, for the purposes of the present application, intended to be taken to mean, inter alia, that the two radicals are linked to one another by a chemical bond. This is illustrated by the following scheme:

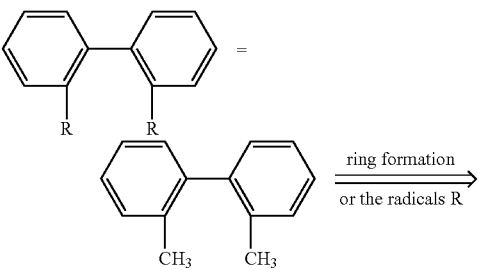

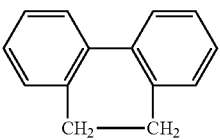

Furthermore, however, the above-mentioned formulation is also intended to be taken to mean that, in the case where one of the two radicals represents hydrogen, the second radical is bonded at the position to which the hydrogen atom was bonded, with formation of a ring. This is intended to be illustrated by the following scheme:

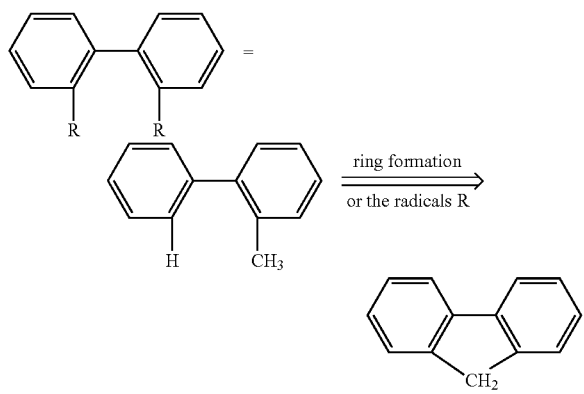

The following are general definitions of chemical groups in the sense of the present application:

An aryl group in the sense of this invention contains 6 to 60 aromatic ring atoms; a heteroaryl group in the sense of this invention contains 5 to 60 aromatic ring atoms, at least one of which is a heteroatom. The heteroatoms are preferably selected from N, O and S. This represents the basic definition. If other preferences are indicated in the description of the present invention, for example with respect to the number of aromatic ring atoms or the heteroatoms present, these apply.

An aryl group or heteroaryl group here is taken to mean either a simple aromatic ring, i.e. benzene, or a simple heteroaromatic ring, for example pyridine, pyrimidine or thiophene, or a condensed (annellated) aromatic or heteroaromatic polycycle, for example naphthalene, phenanthrene, quinoline or carbazole. A condensed (annellated) aromatic or heteroaromatic polycycle in the sense of the present application consists of two or more simple aromatic or heteroaromatic rings condensed with one another.

An electron-deficient heteroaryl group in the sense of the present invention is defined as a 5-membered heteroaryl ring group having at least two heteroatoms, for example imidazole, oxazole, oxadiazole, etc., or as a 6-membered heteroaryl ring group having at least one heteroatom, for example pyridine, pyrimidine, pyrazine, triazine, etc. Further 6-membered aryl or 6-membered heteroaryl ring groups may also be condensed onto these groups, as is the case, for example, in benzimidazole, quinoline or phenanthroline.

An aryl or heteroaryl group, which may in each case be substituted by the above-mentioned radicals and which may be linked to the aromatic or heteroaromatic ring system via any desired positions, is taken to mean, in particular, groups derived from benzene, naphthalene, anthracene, phenanthrene, pyrene, dihydropyrene, chrysene, perylene, fluoranthene, benzanthracene, benzophenanthrene, tetracene, pentacene, benzopyrene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, pyrazine, phenazine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

An aryloxy group in accordance with the definition of the present invention is taken to mean an aryl group, as defined above, which is bonded via an oxygen atom. An analogous definition applies to heteroaryloxy groups.

An aromatic ring system in the sense of this invention contains 6 to 60 C atoms in the ring system. A heteroaromatic ring system in the sense of this invention contains 5 to 60 aromatic ring atoms, at least one of which is a heteroatom. The heteroatoms are preferably selected from N, O and/or S. An aromatic or heteroaromatic ring system in the sense of this invention is intended to be taken to mean a system which does not necessarily contain only aryl or heteroaryl groups, but instead in which, in addition, a plurality of aryl or heteroaryl groups may be connected by a non-aromatic unit (preferably less than 10% of the atoms other than H), such as, for example, an $sp^3$-hybridised C, Si, N or O atom, an $sp^2$-hybridised C or N atom or an sp-hybridised C atom. Thus, for example, systems such as 9,9'-spirobifluorene, 9,9'-diarylfluorene, triarylamine, diaryl ether, stilbene, etc., are also intended to be taken to be aromatic ring systems in the sense of this invention, as are systems in which two or more aryl groups are connected, for example, by a linear or cyclic alkyl, alkenyl or alkynyl group or by a silyl group. Furthermore, systems in which two or more aryl or heteroaryl groups are linked to one another via single bonds are also taken to be aromatic or heteroaromatic ring systems in the sense of this invention, such as, for example, systems such as biphenyl, terphenyl or diphenyltriazine.

An aromatic or heteroaromatic ring system having 5-60 aromatic ring atoms, which may in each case also be substituted by radicals as defined above and which may be linked to the aromatic or heteroaromatic group via any desired positions, is taken to mean, in particular, groups derived from benzene, naphthalene, anthracene, benzanthracene, phenanthrene, benzophenanthrene, pyrene, chrysene, perylene, fluoranthene, naphthacene, pentacene, benzopyrene, biphenyl, biphenylene, terphenyl, terphenylene, quaterphenyl, fluorene, spirobifluorene, dihydrophenanthrene, dihydropyrene, tetrahydropyrene, cis- or trans-indenofluorene, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, indolocarbazole, indenocarbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubin, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole, or combinations of these groups.

For the purposes of the present invention, a straight-chain alkyl group having 1 to 40 C atoms or a branched or cyclic alkyl group having 3 to 40 C atoms or an alkenyl or alkynyl group having 2 to 40 C atoms, in which, in addition, individual H atoms or $CH_2$ groups may be substituted by the groups mentioned above under the definition of the radicals, is preferably taken to mean the radicals methyl, ethyl, n-propyl, i-propyl, n-butyl, i-butyl, s-butyl, t-butyl, 2-methylbutyl, n-pentyl, s-pentyl, cyclopentyl, neopentyl, n-hexyl, cyclohexyl, neohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, hepteny, cycloheptenyl, octenyl, cyclooctenyl, ethynyl, propynyl, butynyl, pentynyl, hexynyl or octynyl. An alkoxy or thioalkyl group having 1 to 40 C atoms is preferably taken to mean methoxy, trifluoromethoxy, ethoxy, n-propoxy, i-propoxy, n-butoxy, i-butoxy, s-butoxy, t-butoxy, n-pentoxy, s-pentoxy, 2-methylbutoxy, n-hexoxy, cyclohexyloxy, n-heptoxy, cyclo-heptyloxy, n-octyloxy, cyclooctyloxy, 2-ethylhexyloxy, pentafluoroethoxy, 2,2,2-tri-fluoroethoxy, methylthio, ethylthio, n-propylthio, i-propylthio, n-butylthio, i-butylthio, s-butylthio, t-butylthio, n-pentylthio, s-pentylthio, n-hexylthio, cyclohexylthio, n-heptylthio, cycloheptylthio, n-octylthio, cyclooctylthio, 2-ethylhexylthio, trifluoromethylthio, pentafluoro-ethylthio, 2,2,2-trifluoroethylthio, ethenylthio, propenylthio, butenylthio, pentenylthio, cyclo-pentenylthio, hexenylthio, cyclohexenylthio, heptenylthio, cycloheptenylthio, octenylthio, cyclooctenylthio, ethynylthio, propynylthio, butynylthio, pentynylthio, hexynylthio, heptynylthio or octynylthio.

The compounds according to the invention can be prepared in accordance with Scheme 1. The corresponding monoboronic acids are commercially available and can be converted into the corresponding target molecules by Suzuki coupling and subsequent bromination and further reaction by Buchwald coupling.

Scheme 1

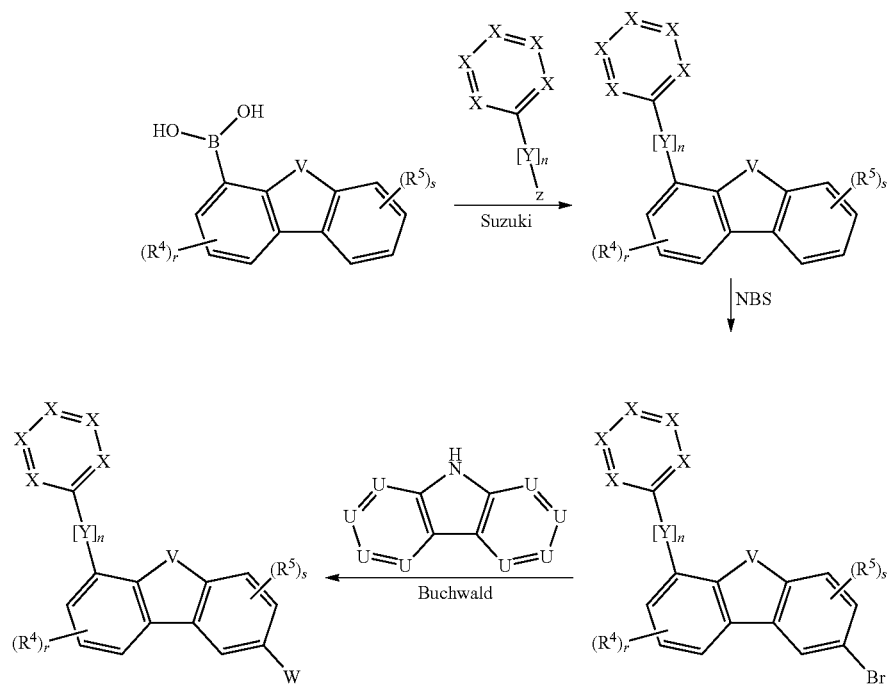

where Z is equal to Cl, Br or I and the other symbols and indices have the meanings indicated above. The reaction scheme can also be used entirely analogously for the preparation of the compounds of the formula (1).

The general process shown for the synthesis of the compounds according to the invention is illustrative. The person skilled in the art will be able to develop alternative synthetic routes within the scope of his general expert knowledge.

The following overview contains an illustrative depiction of compounds according to the invention which can be prepared by one of the processes described herein.

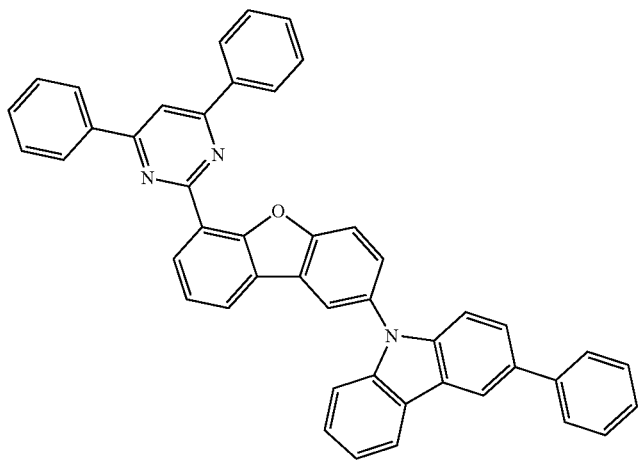
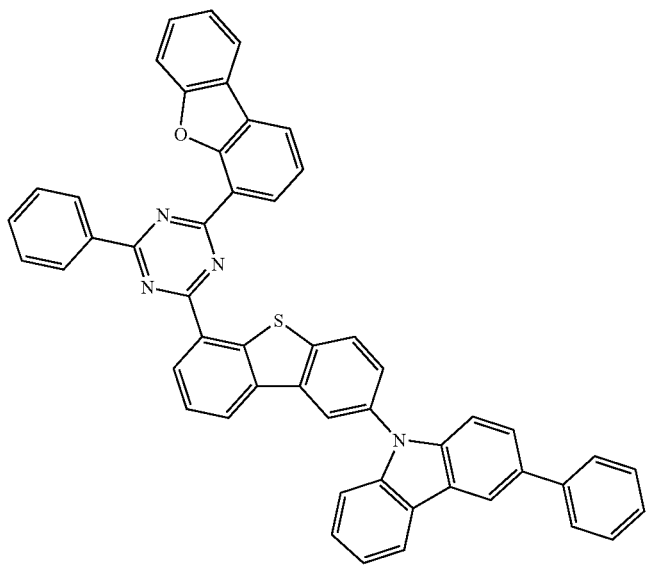
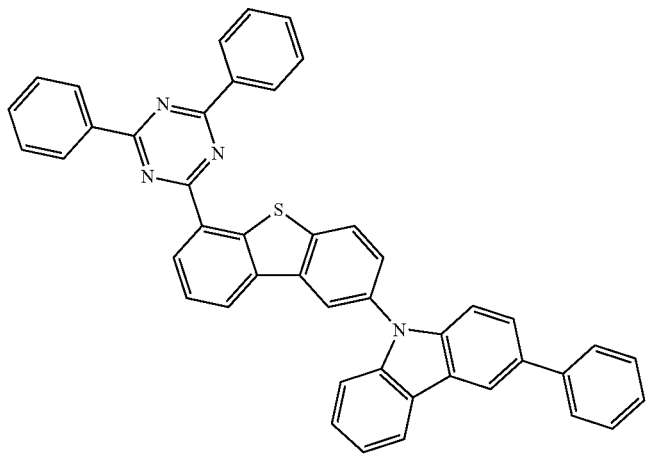

-continued
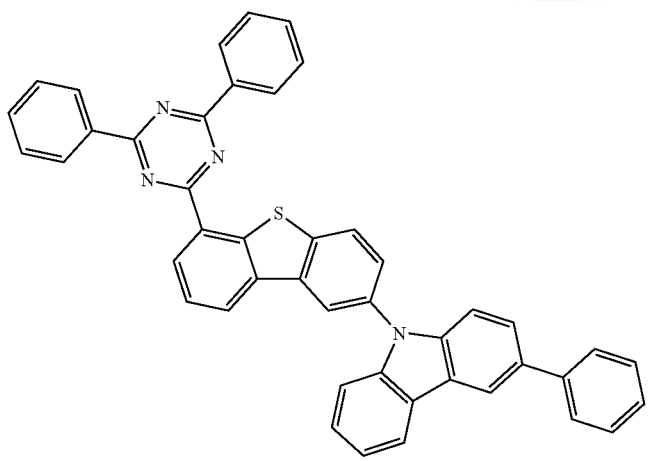
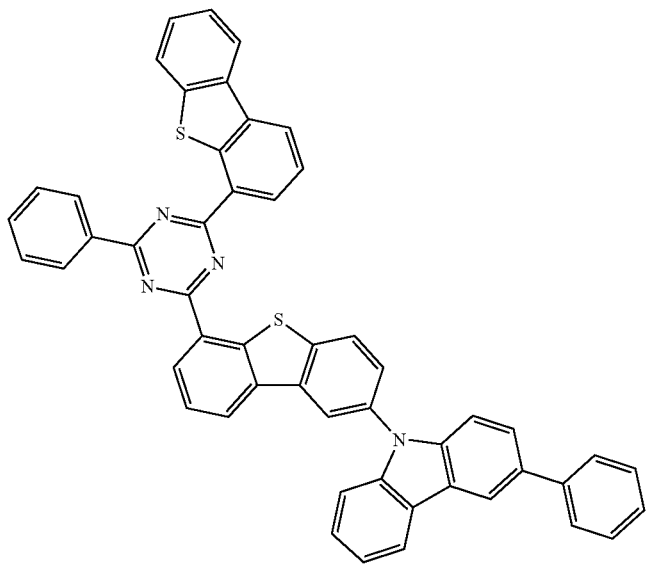
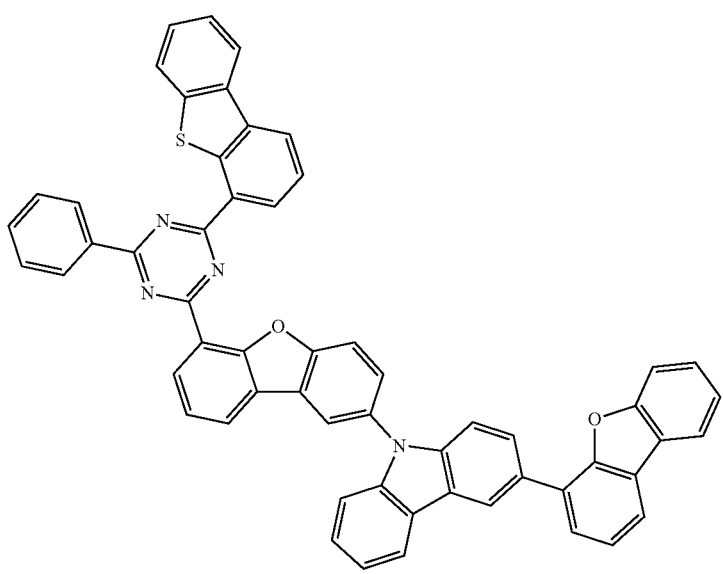

-continued
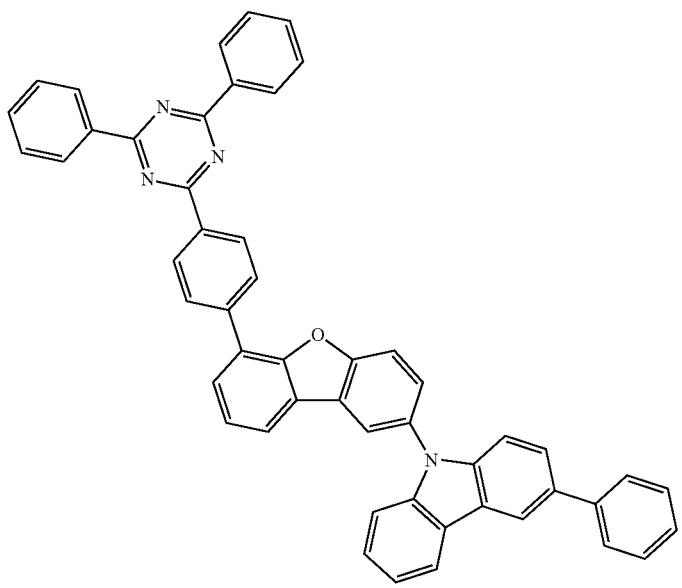
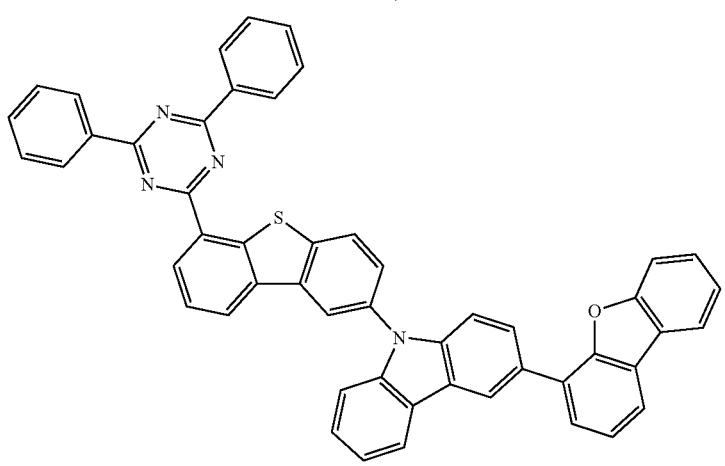
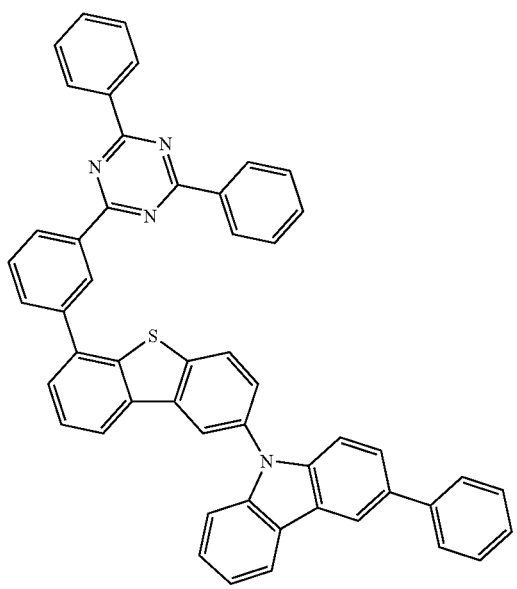

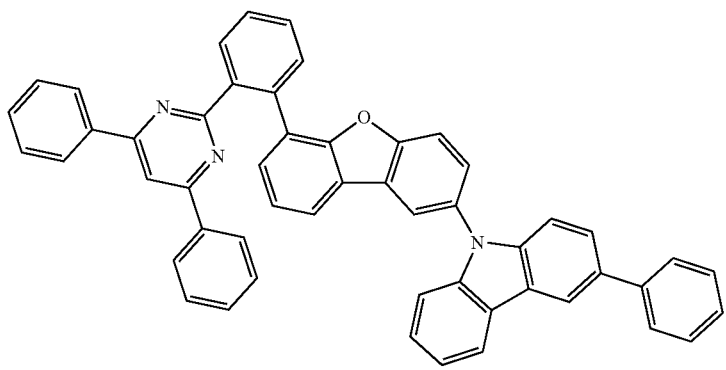
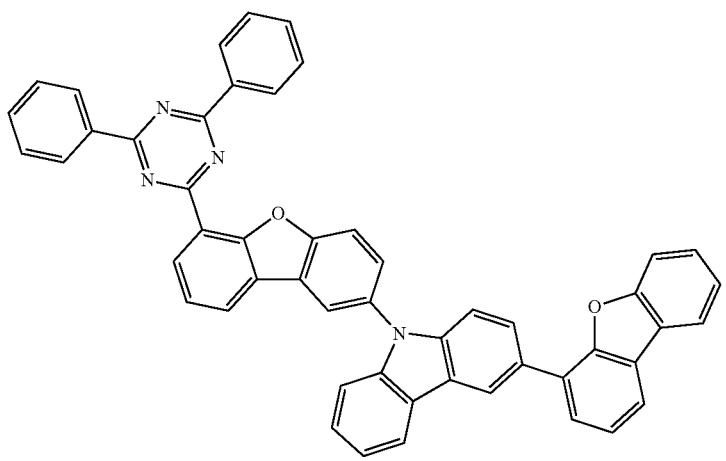
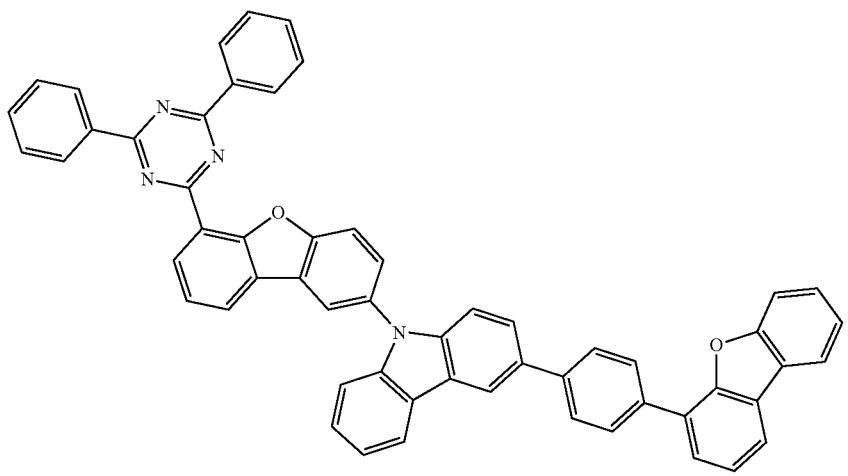

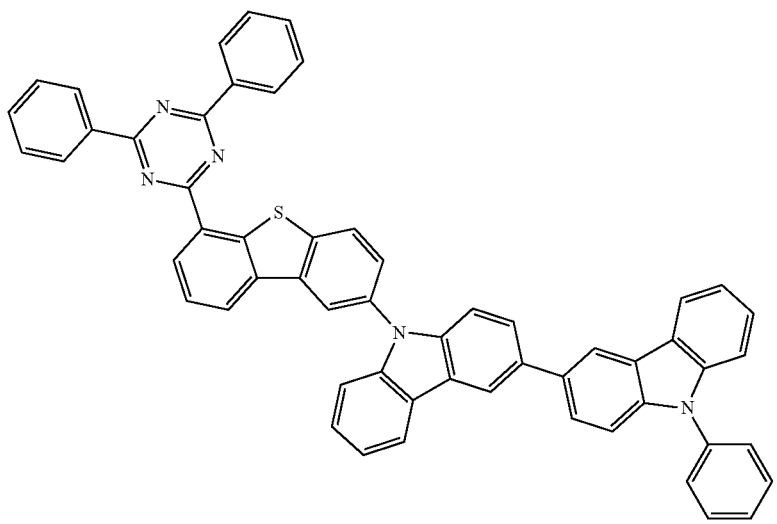
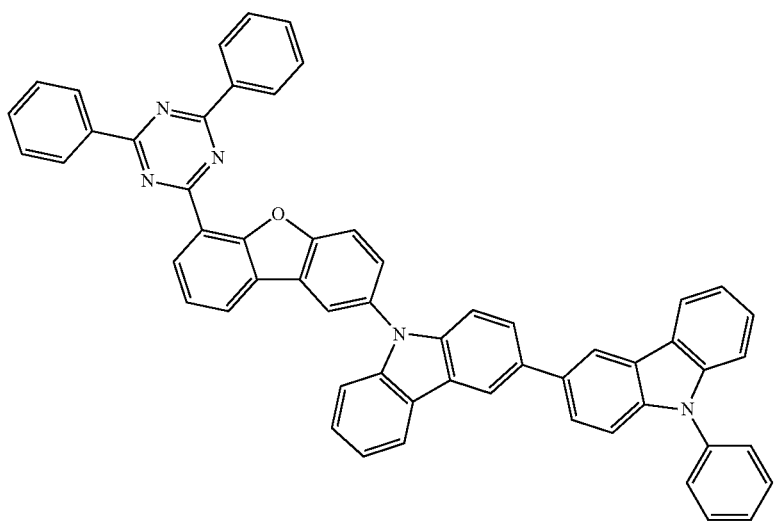
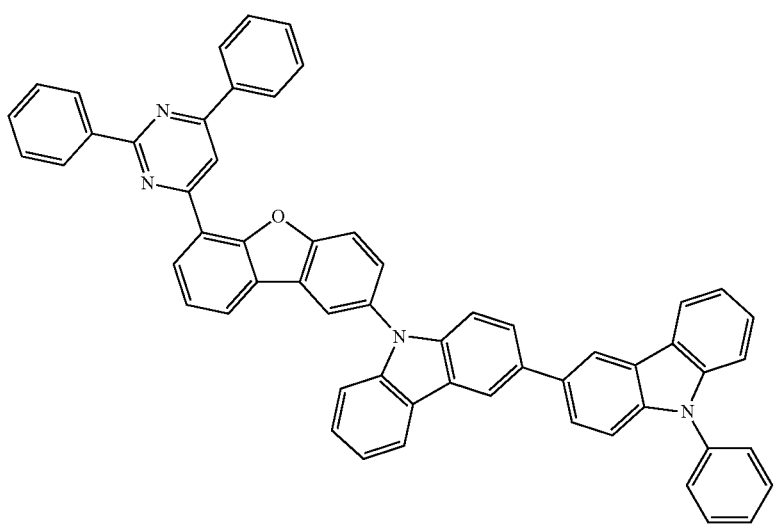

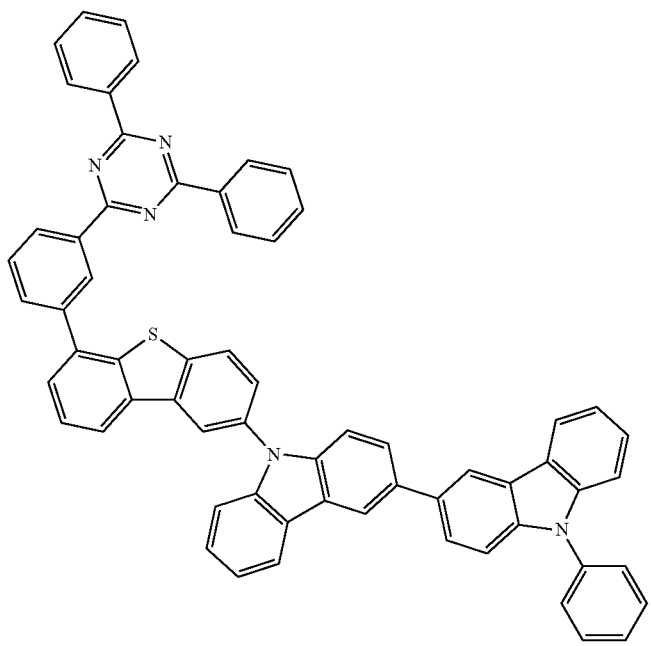
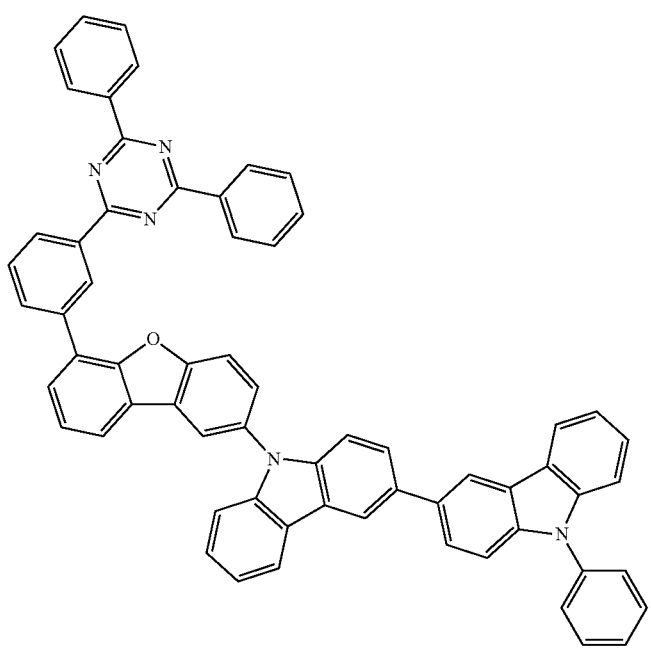

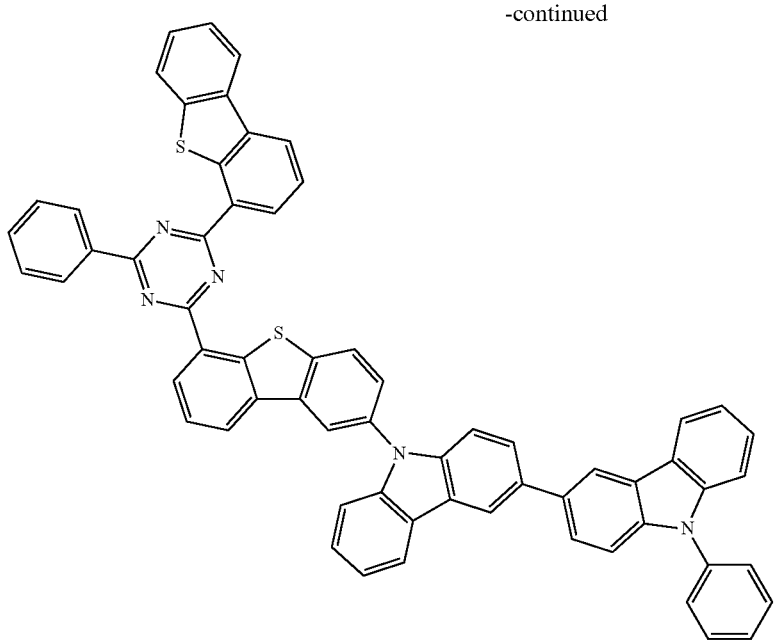
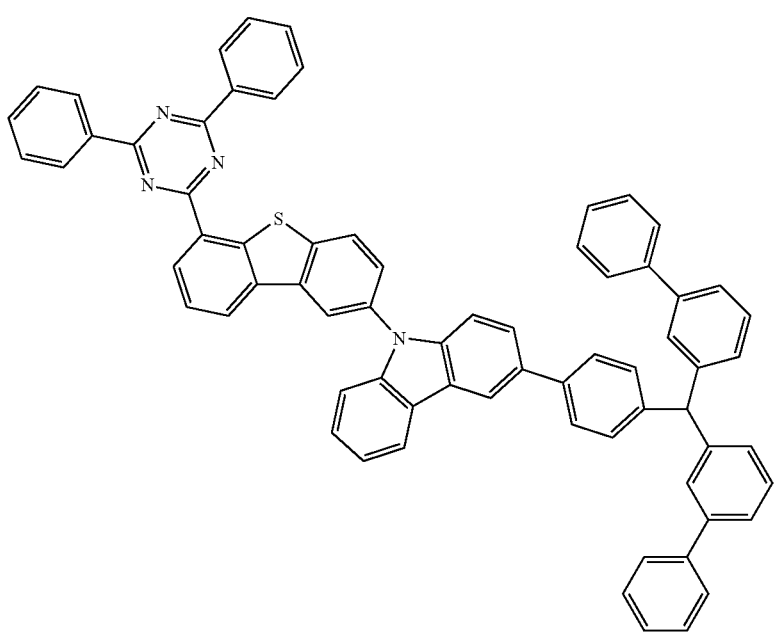
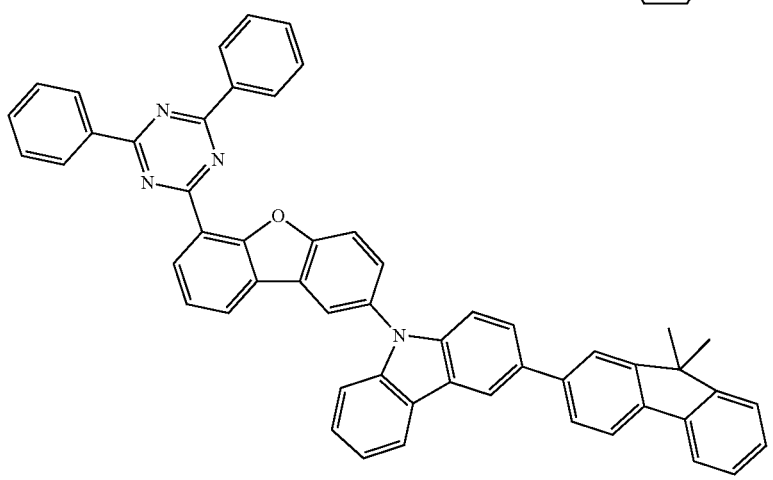

-continued
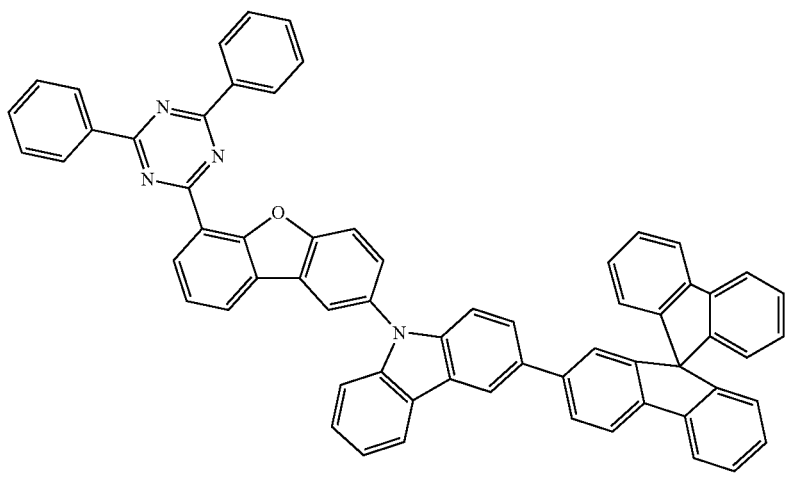
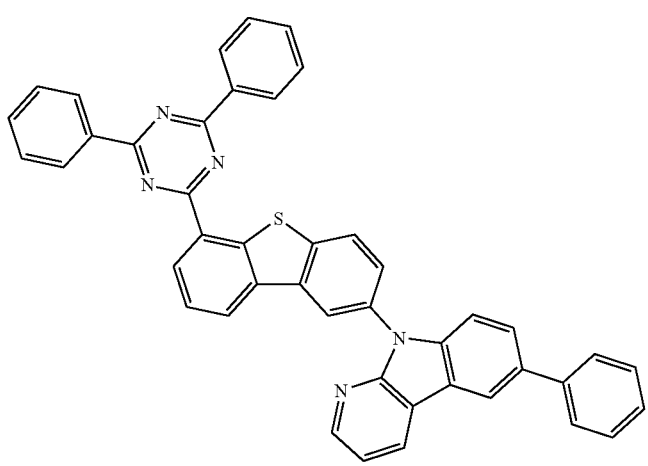
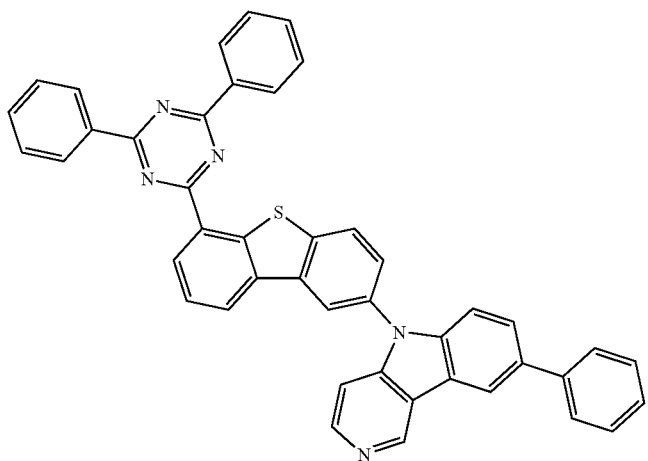

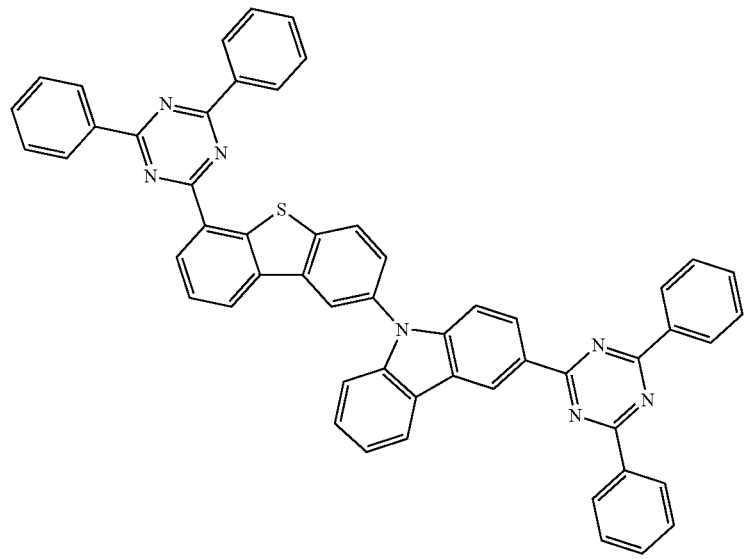
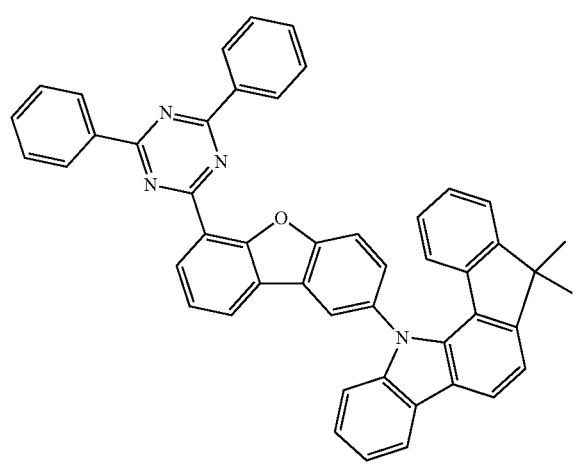
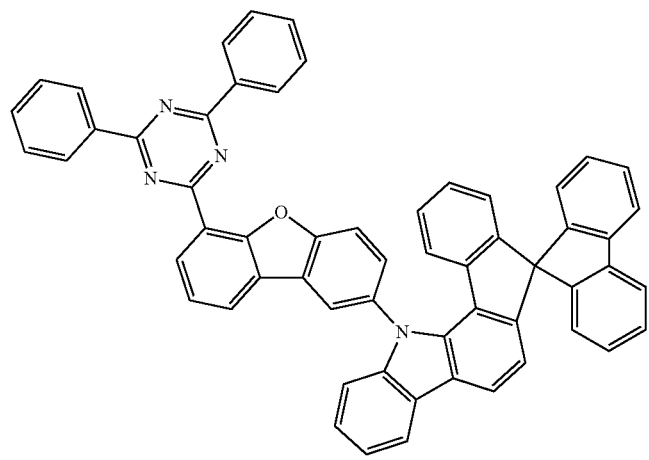

-continued
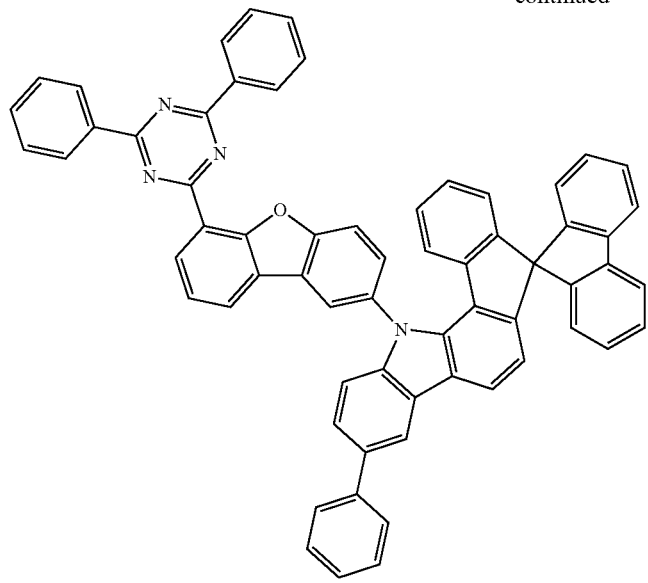
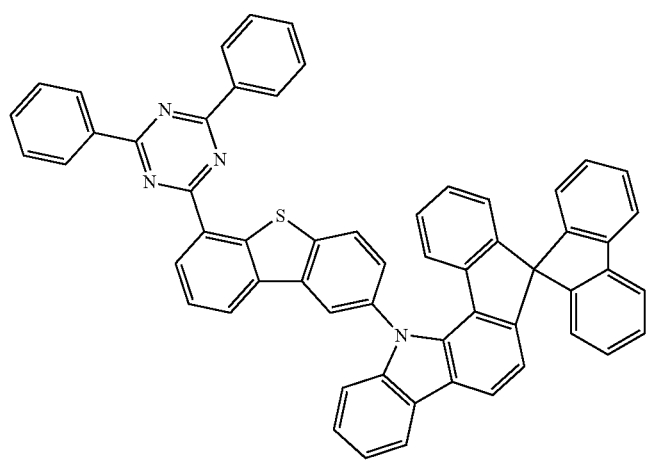
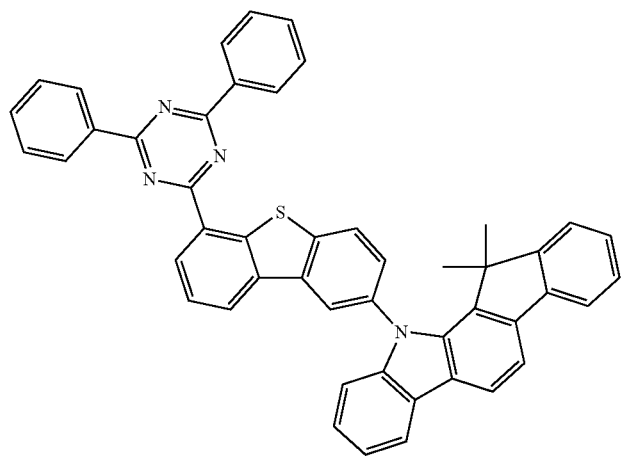

-continued
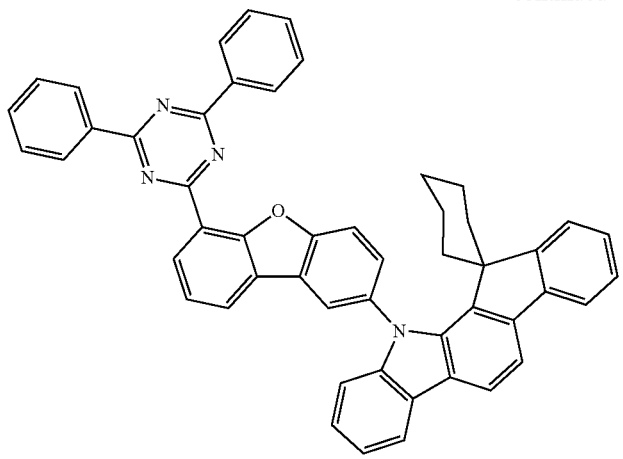
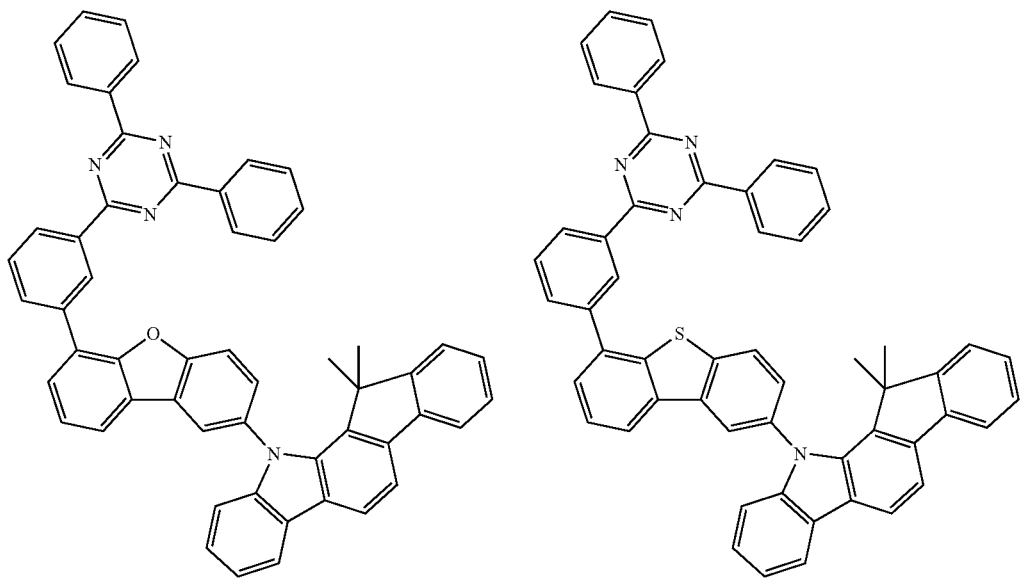
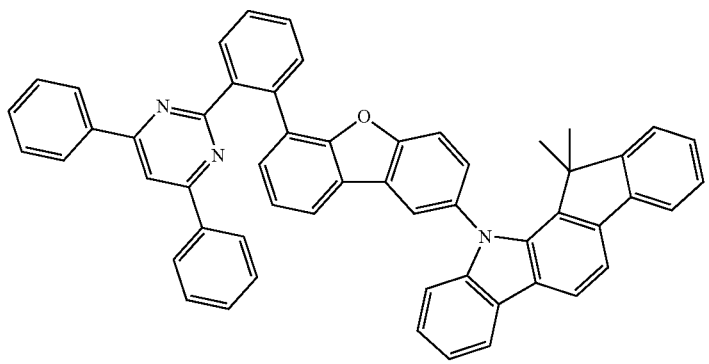

-continued
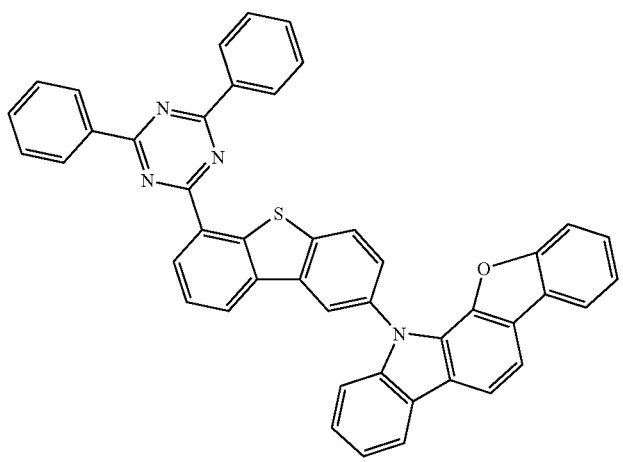
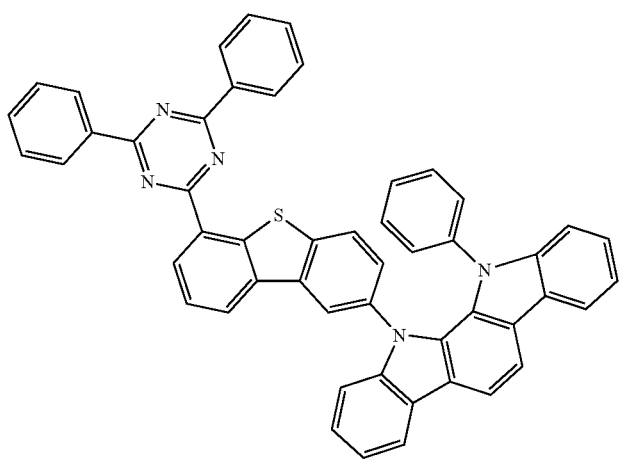
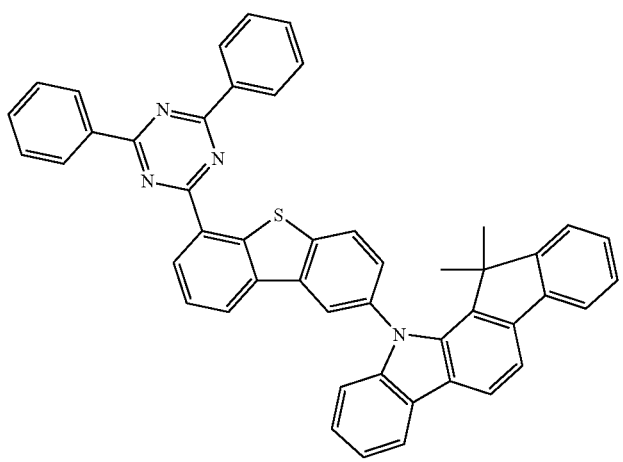

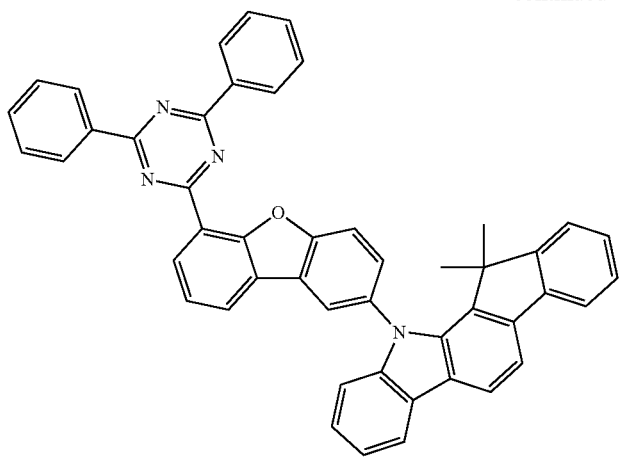
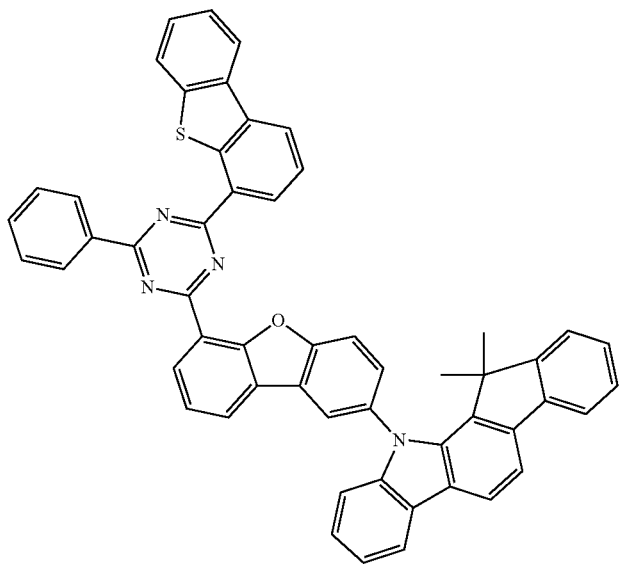
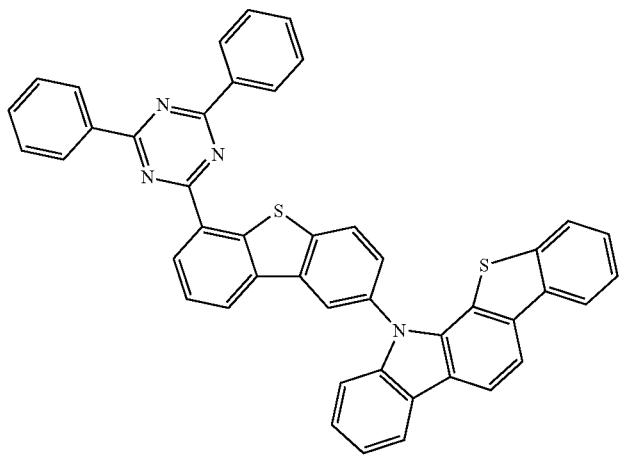

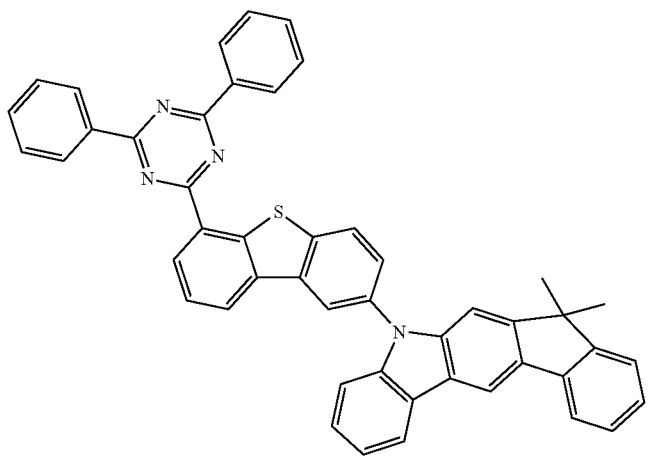
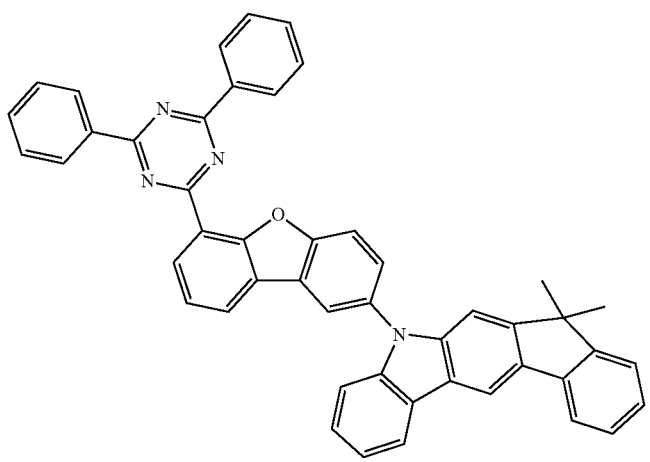
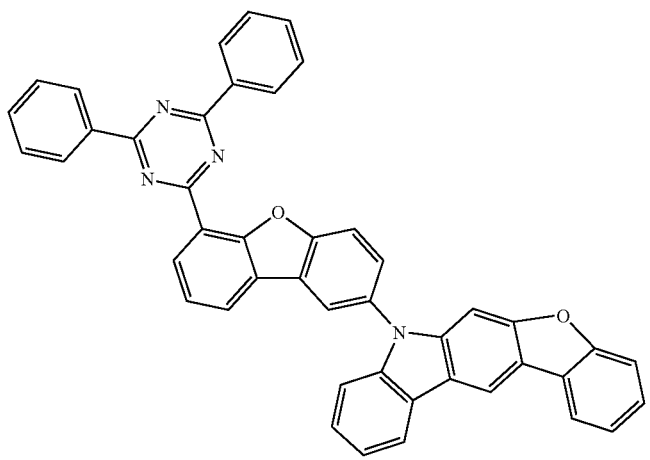

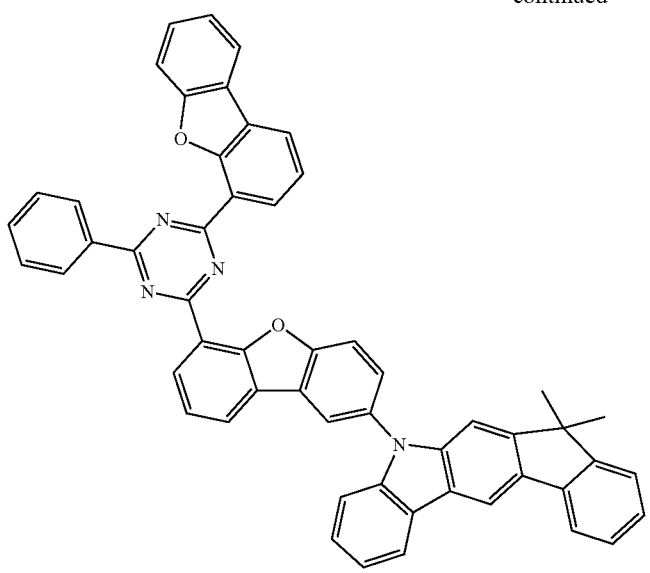
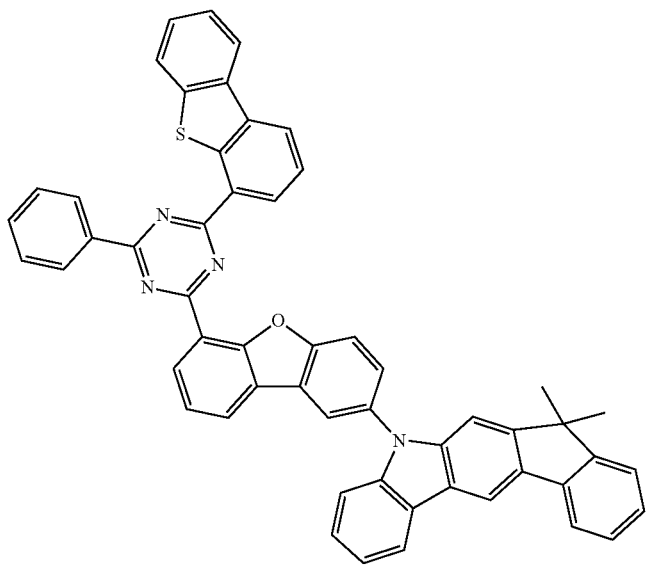
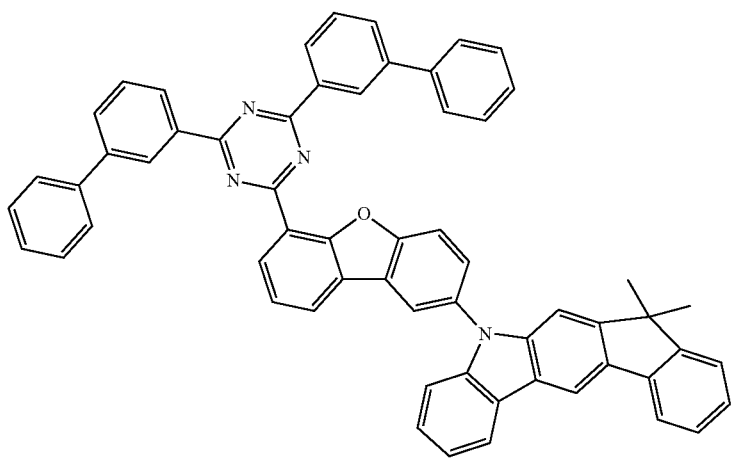

-continued
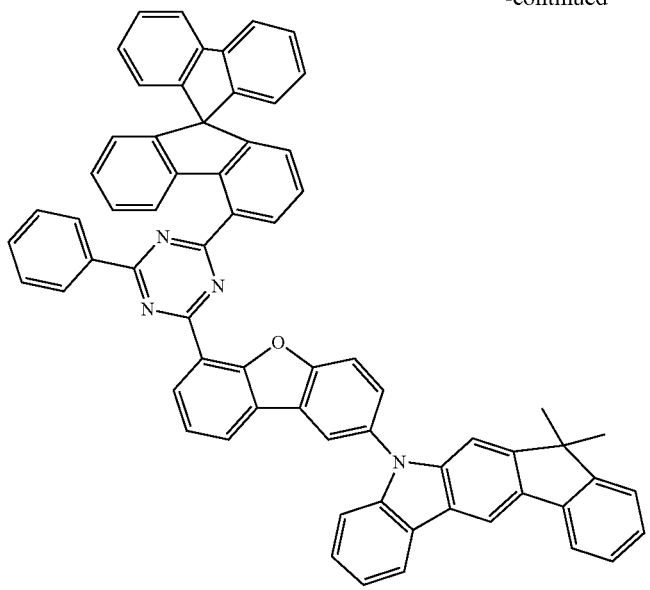
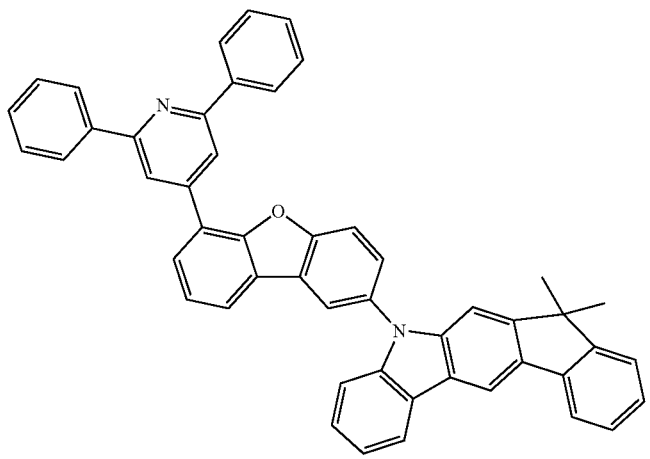
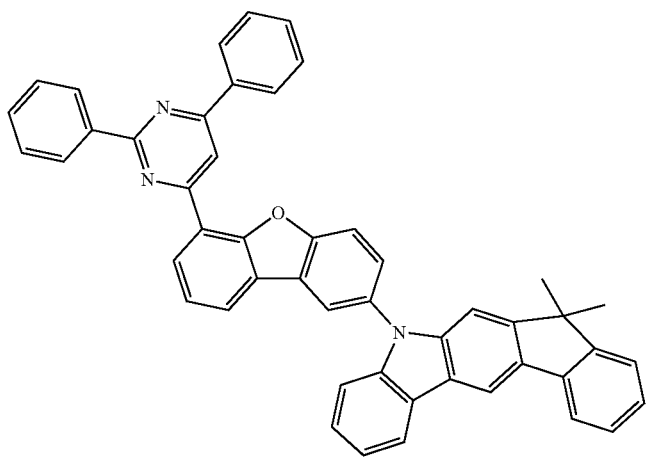

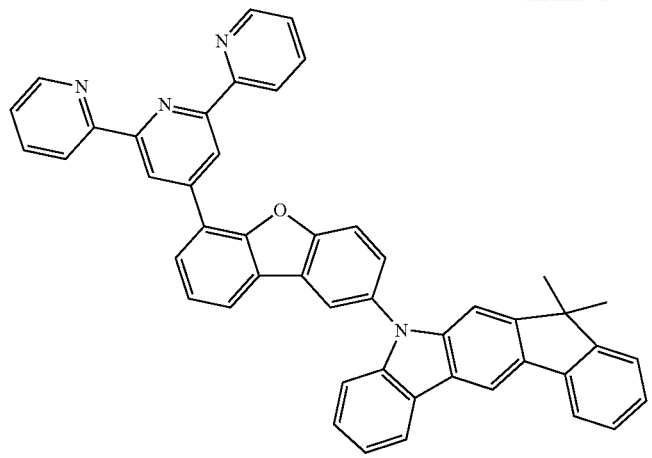
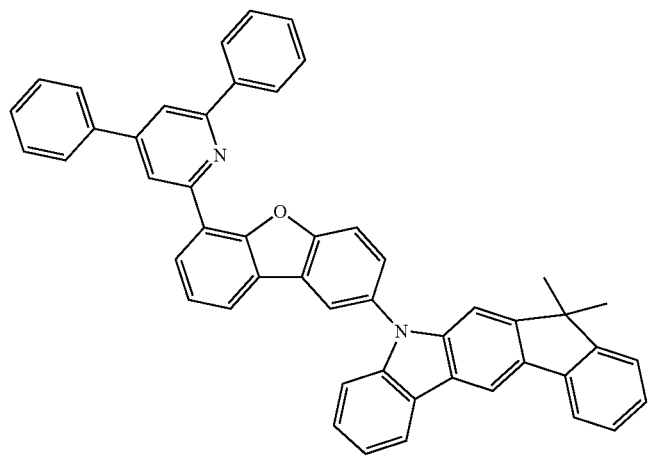
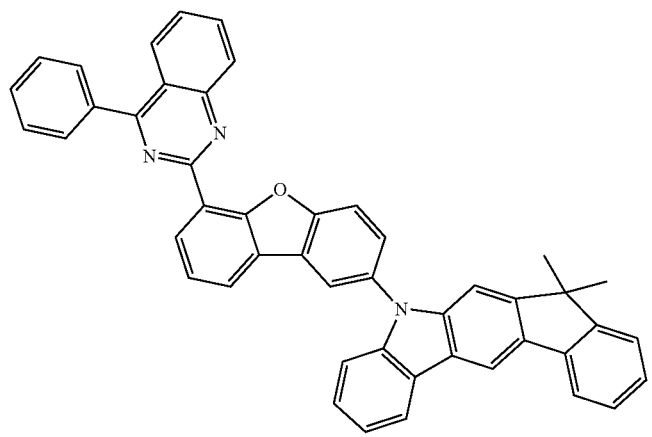
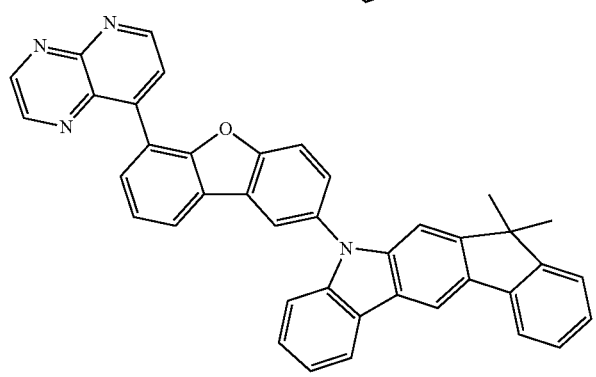

-continued
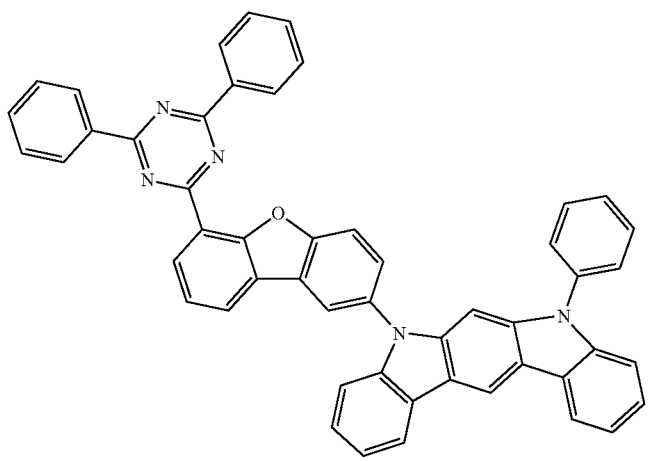
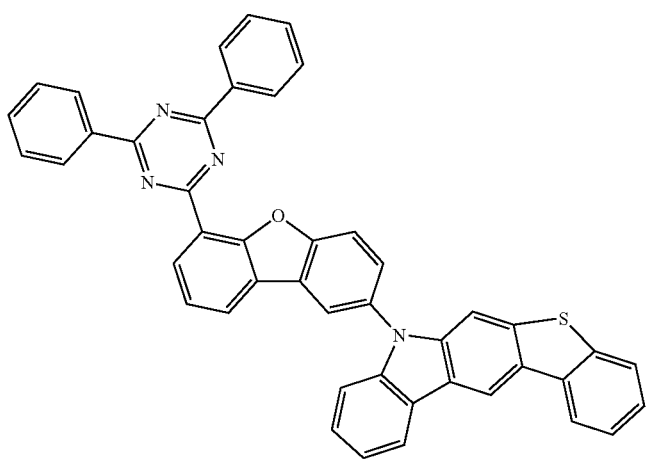
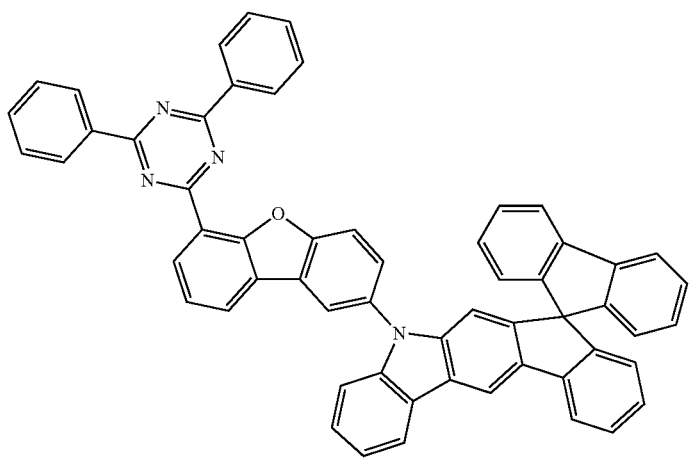

-continued
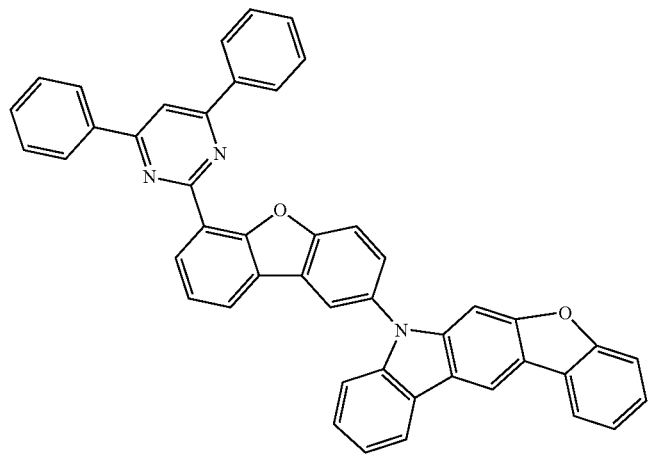
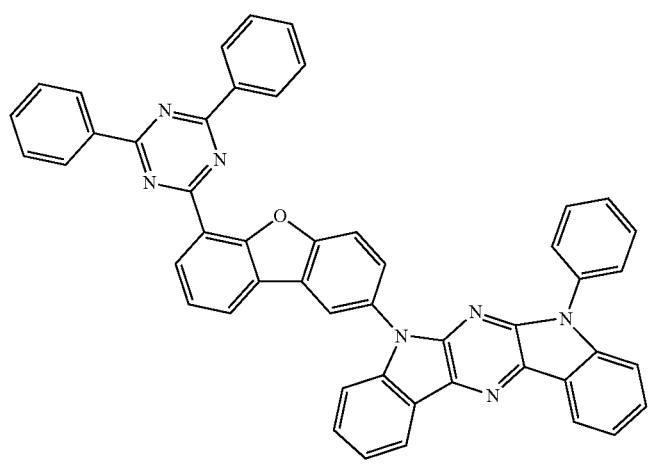
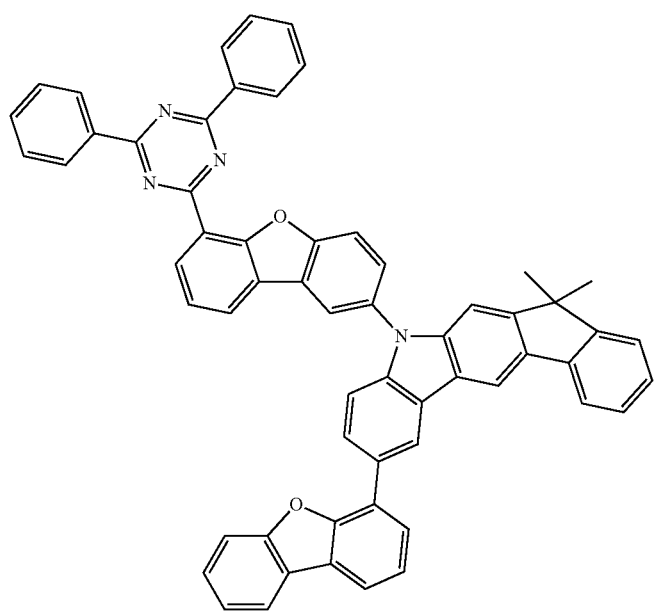

-continued
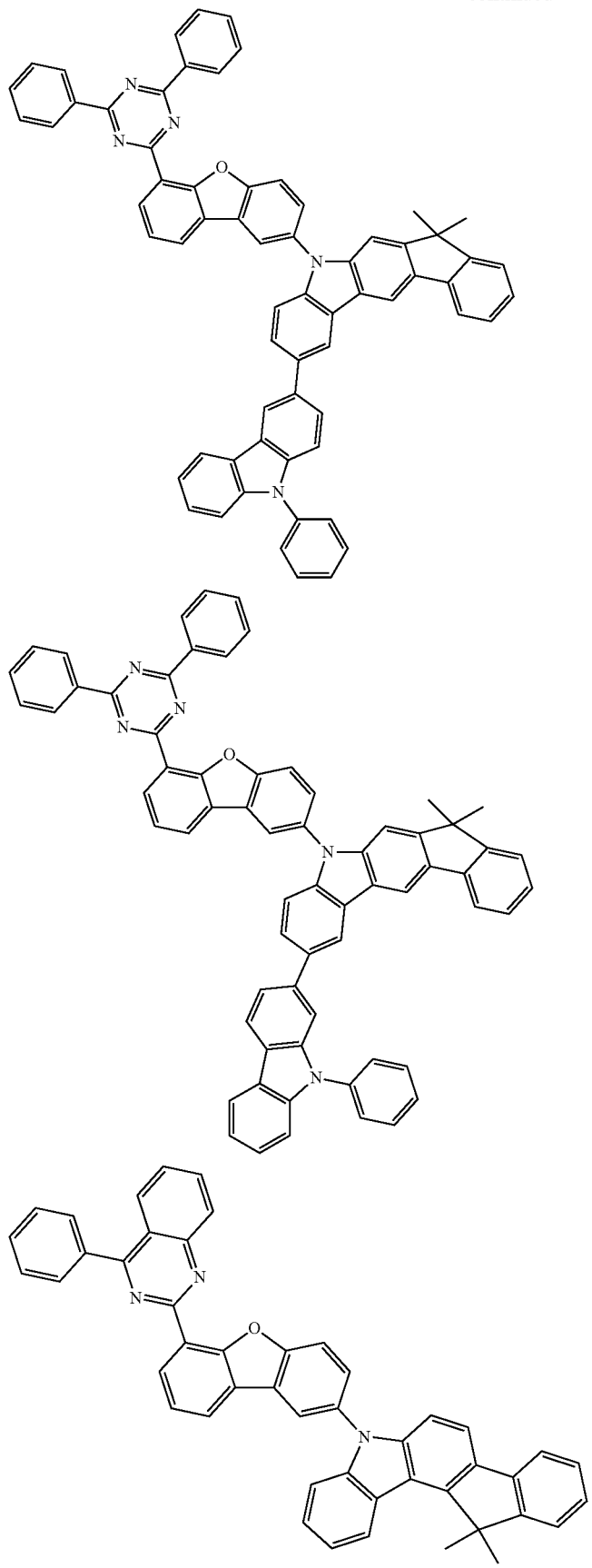

-continued
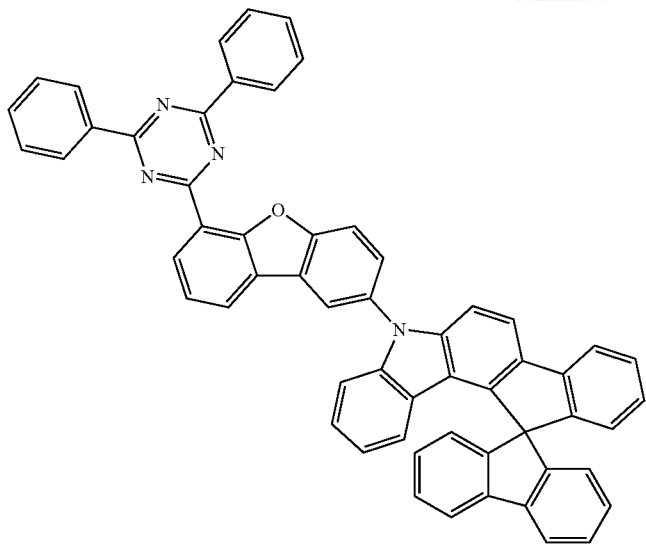
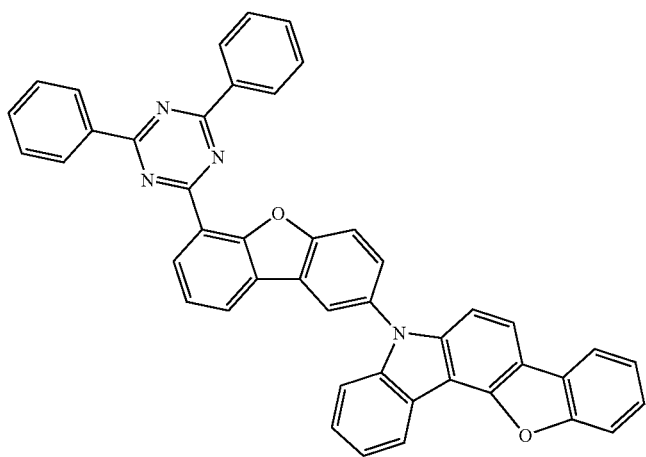
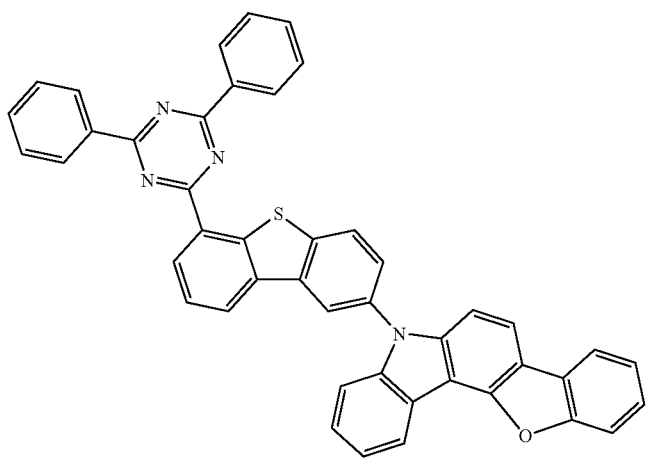

-continued
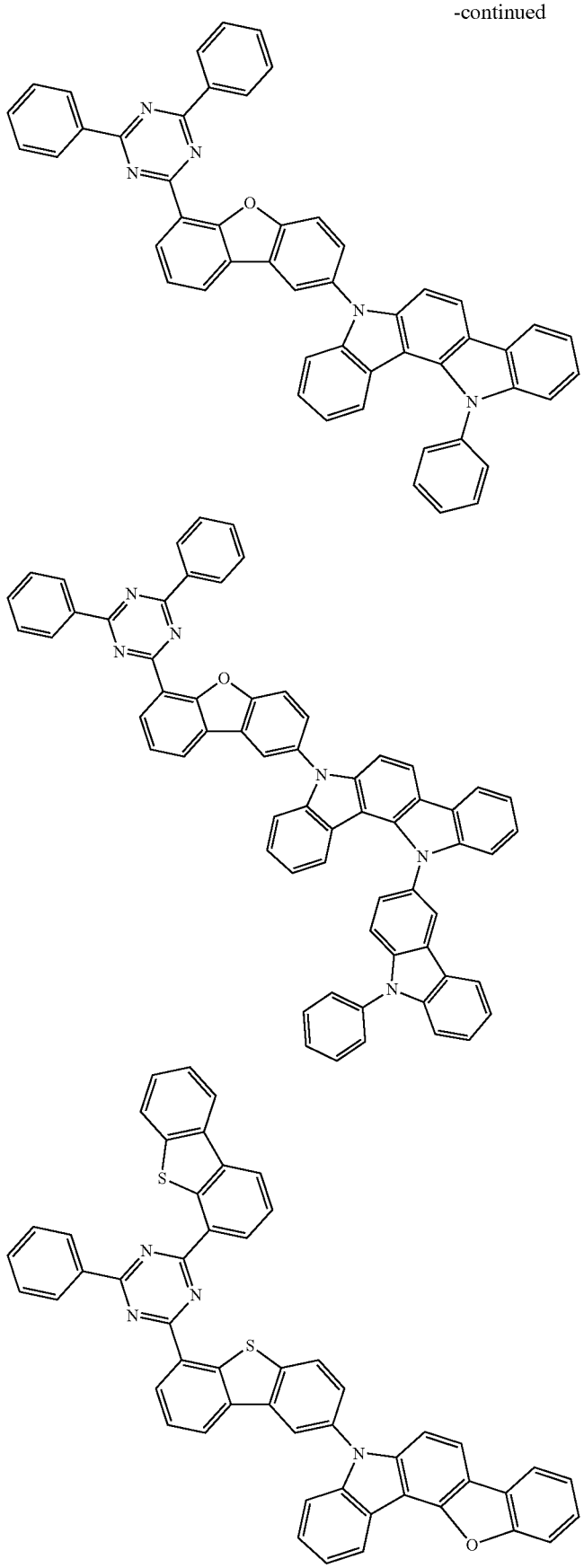

-continued
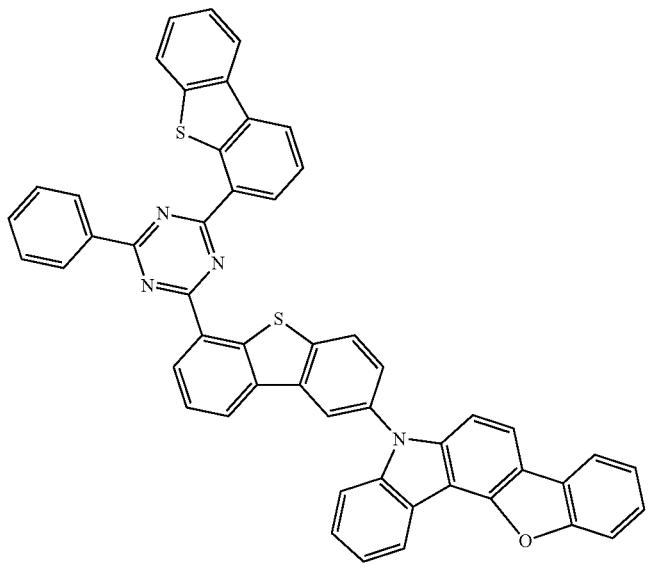
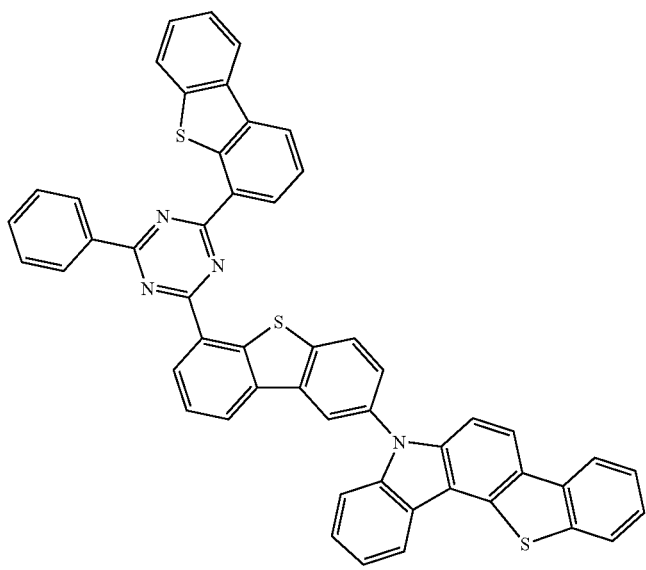
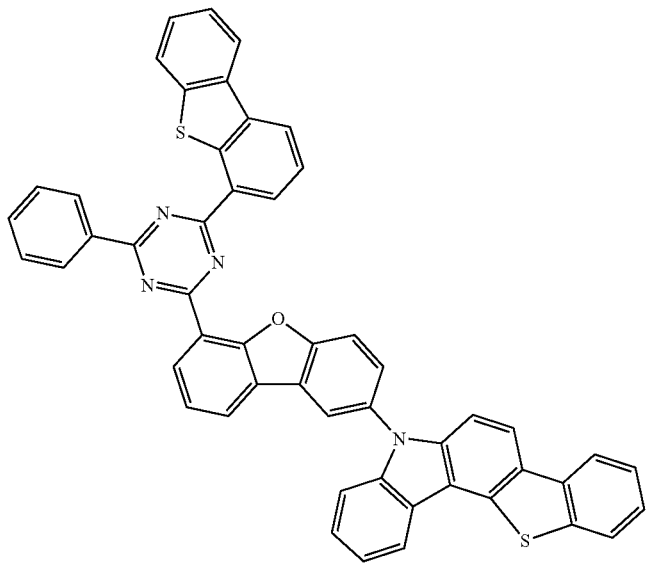

-continued
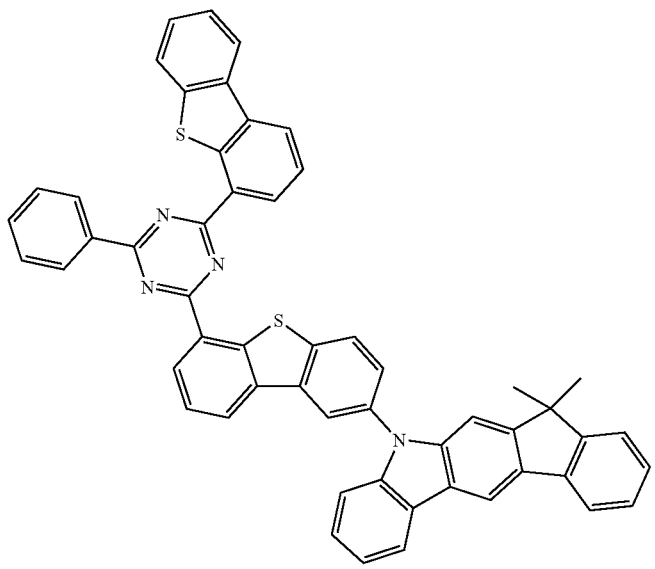
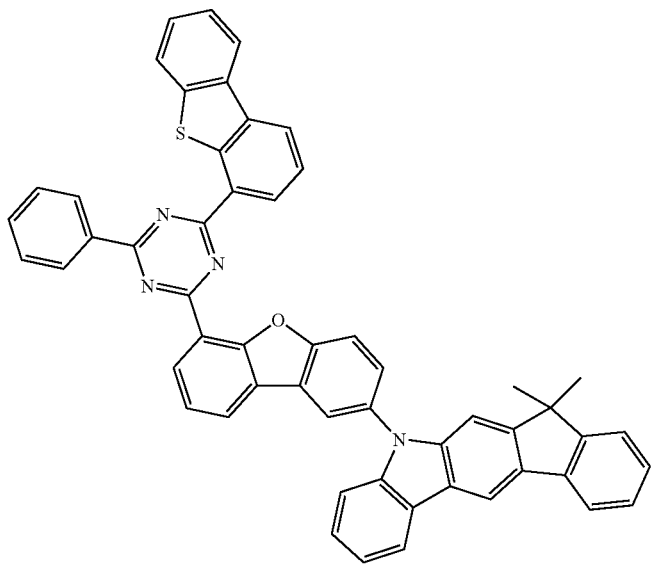
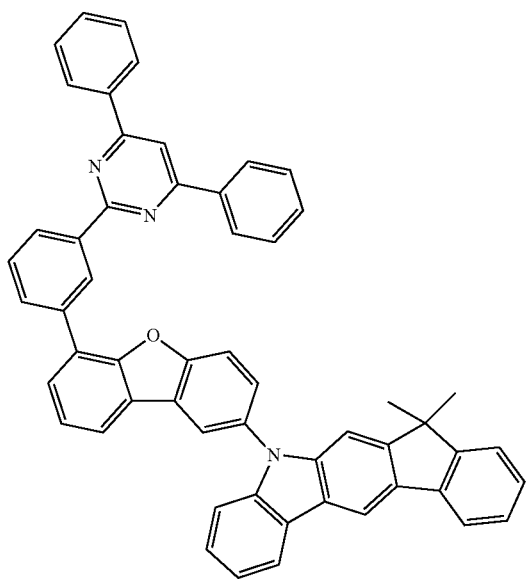
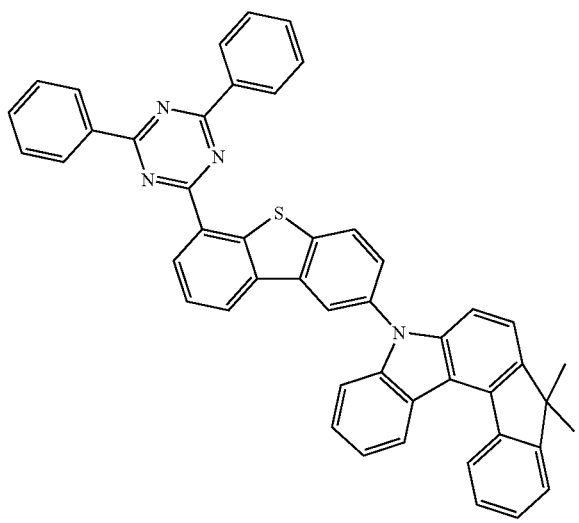

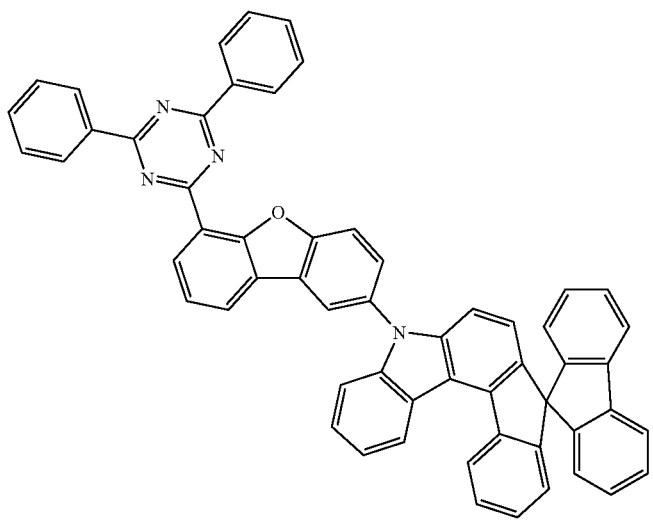
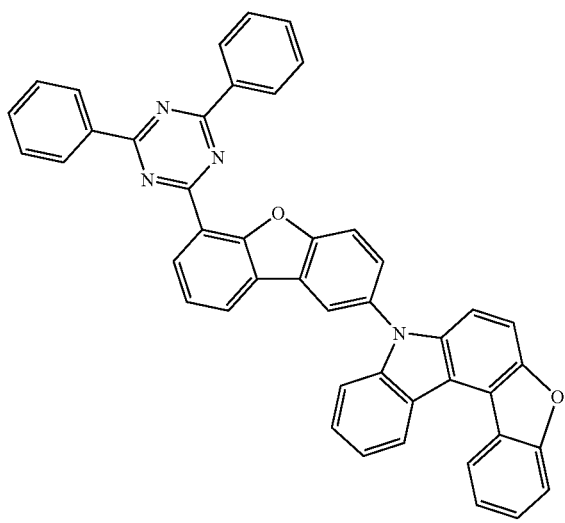
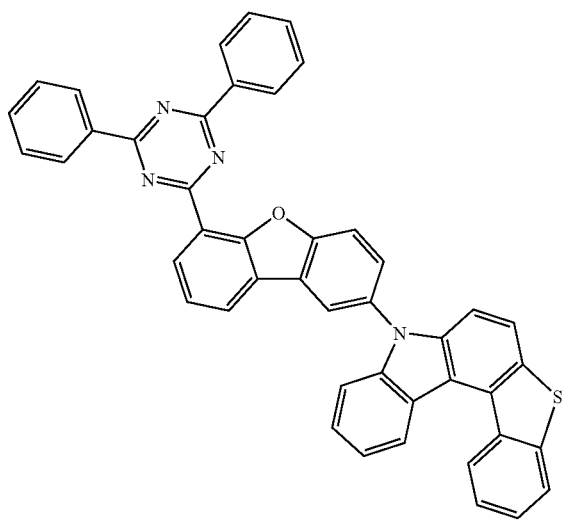
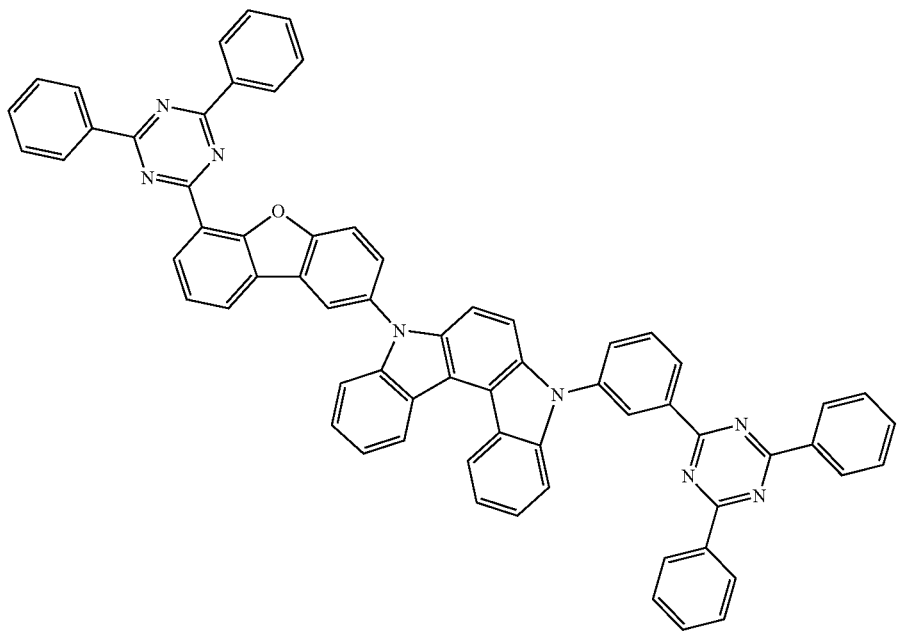

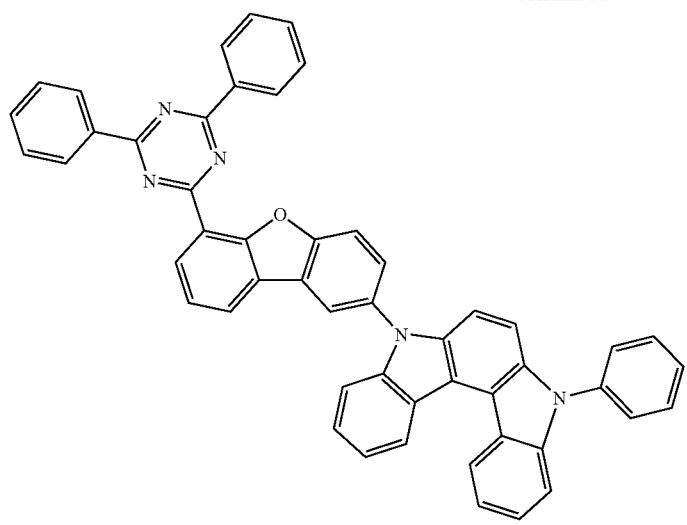
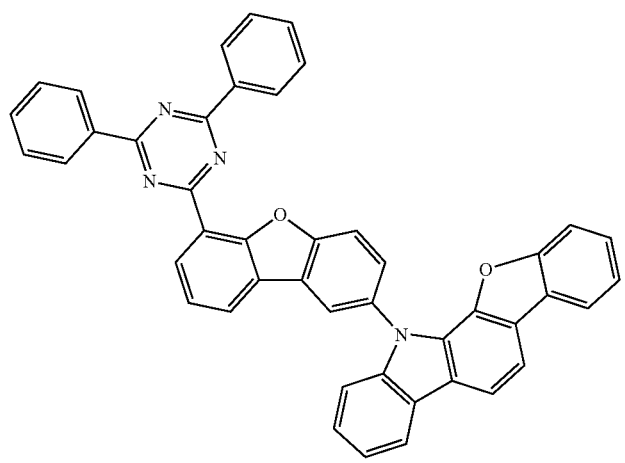
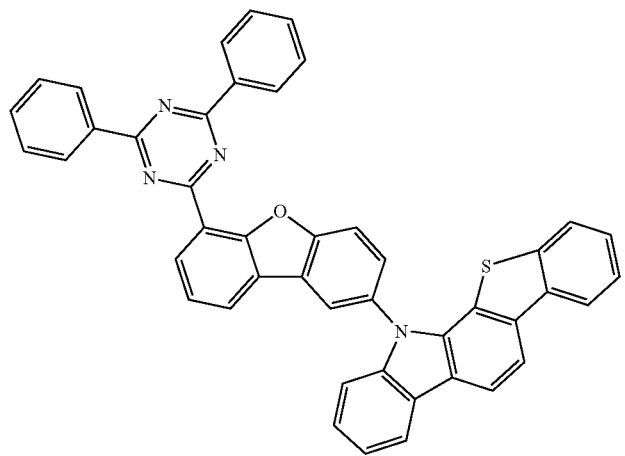

-continued
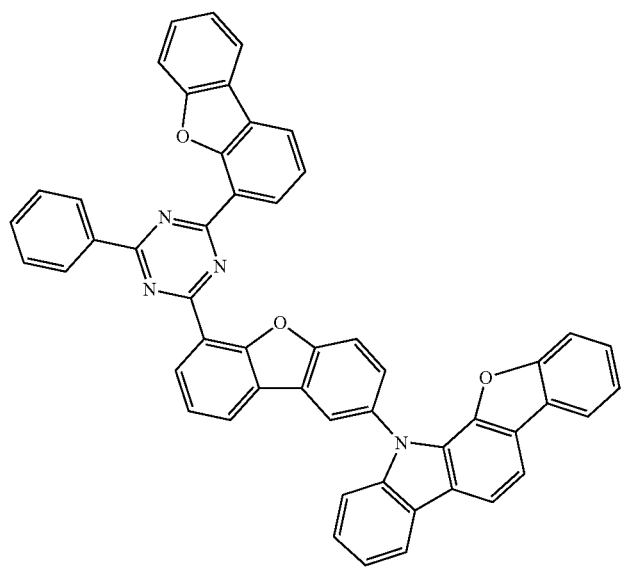
lp;3p
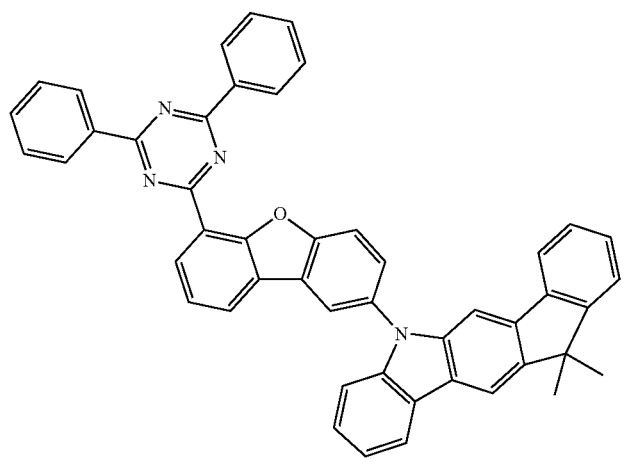
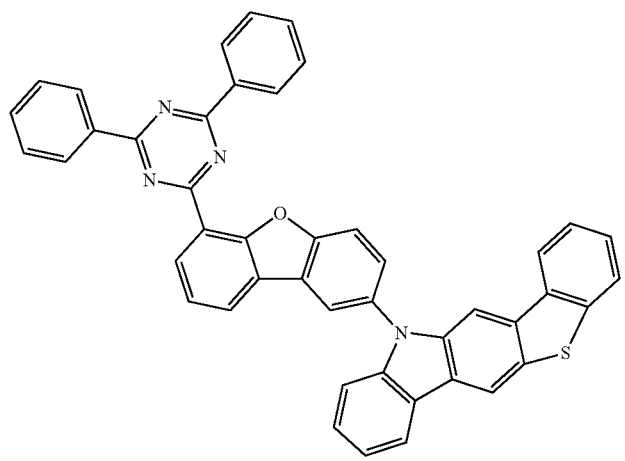

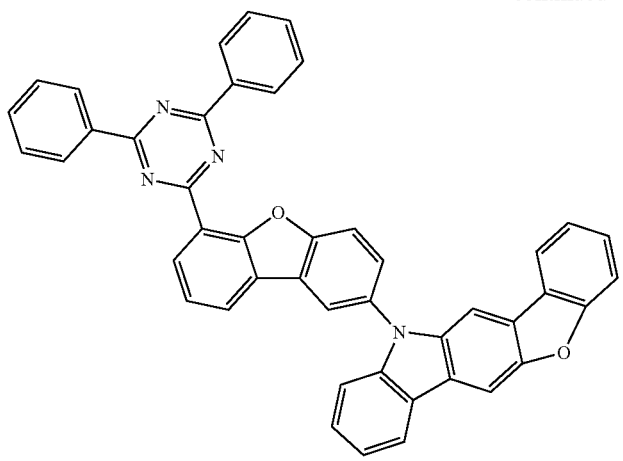
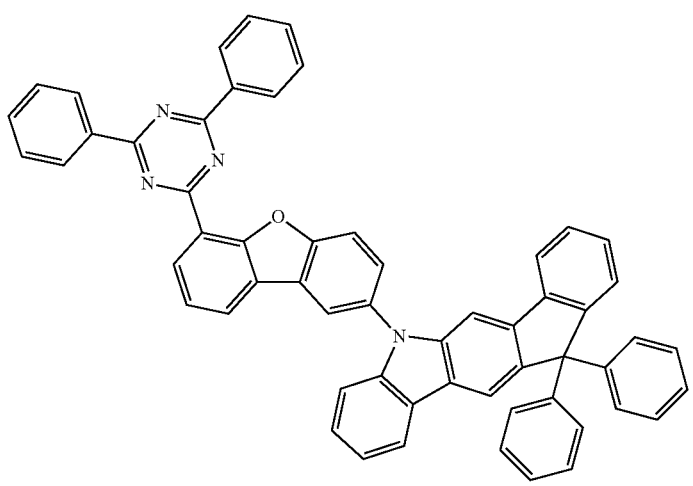
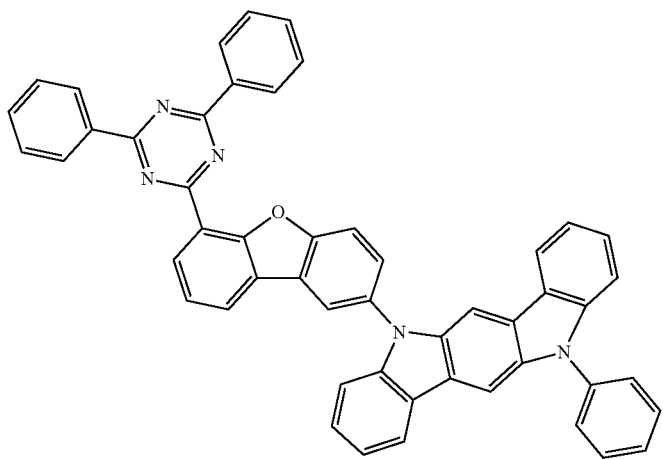

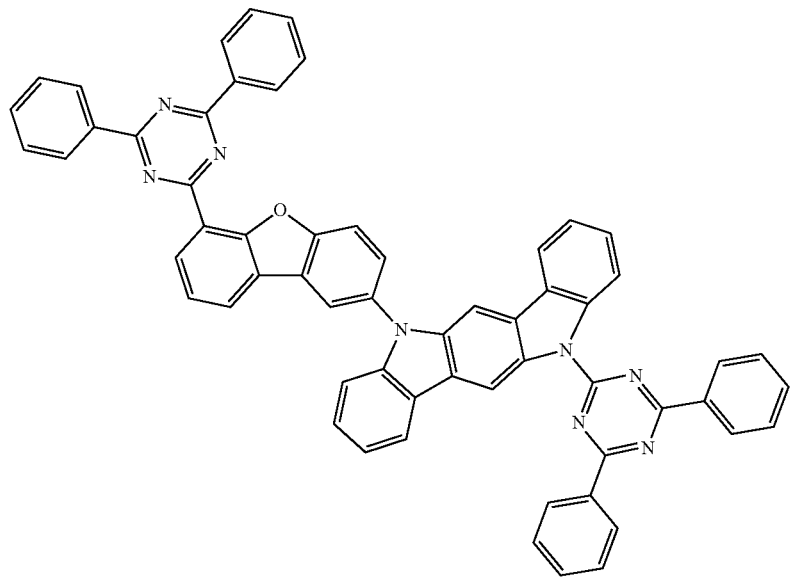
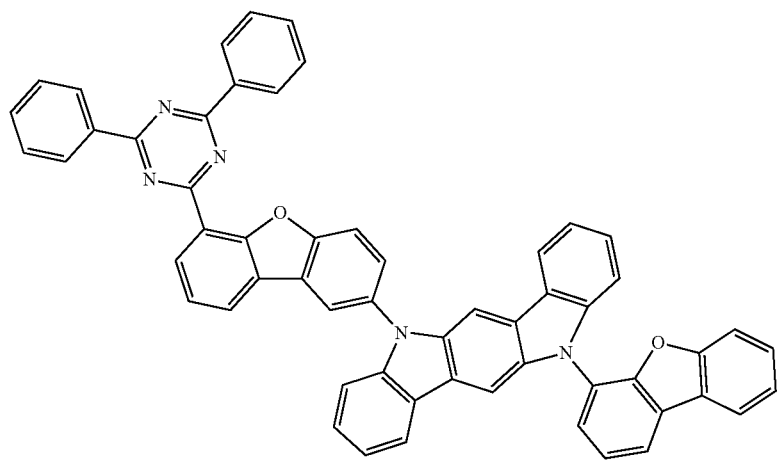
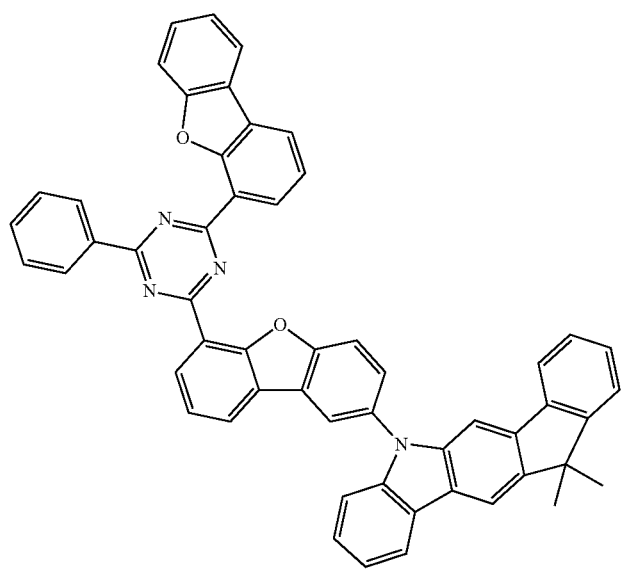

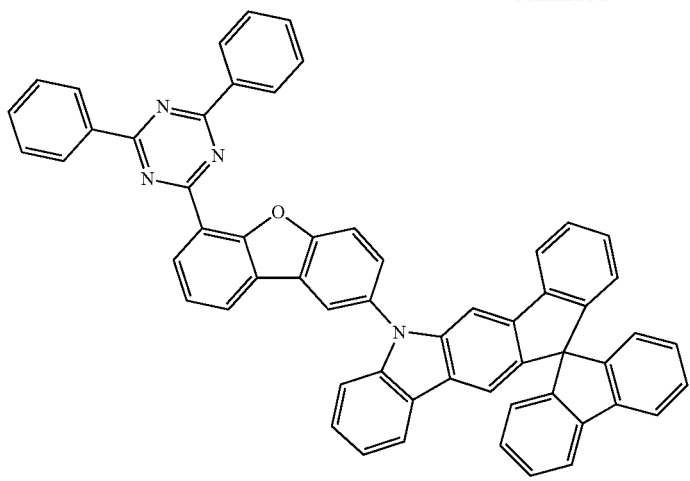
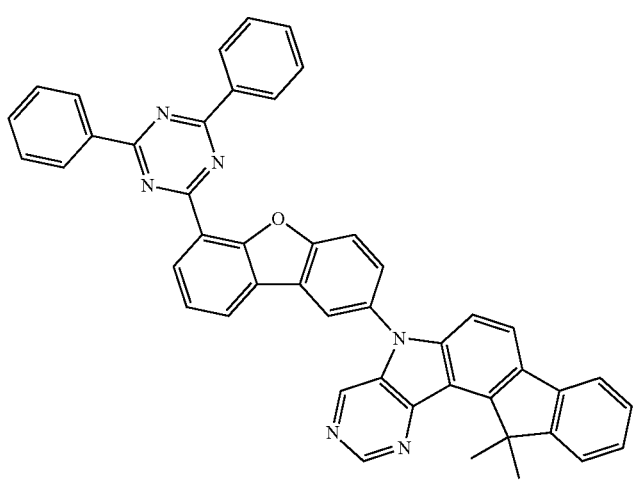
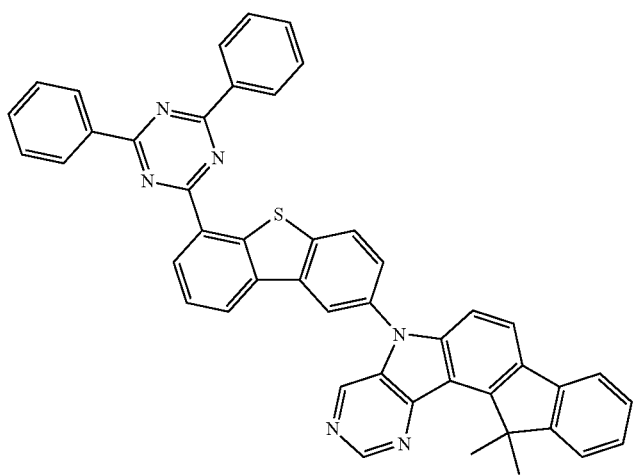

-continued
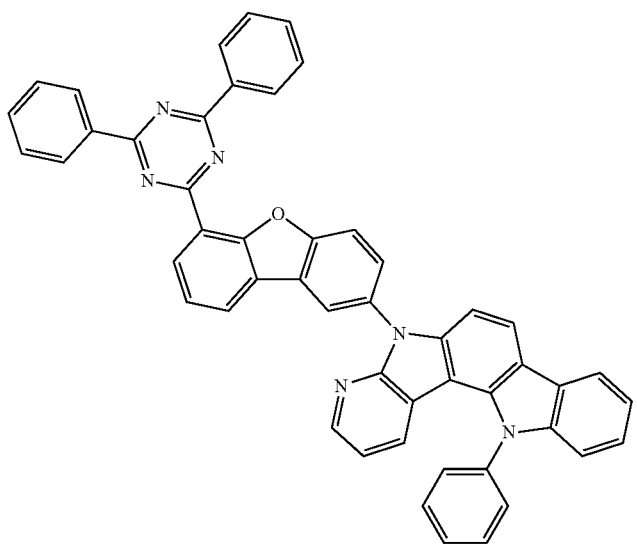
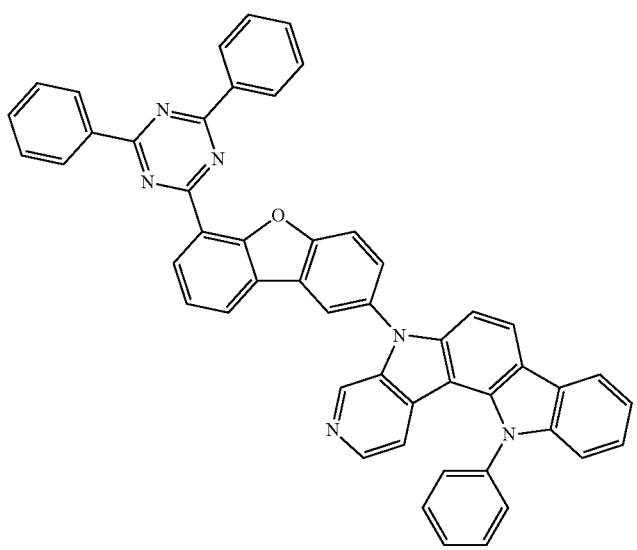
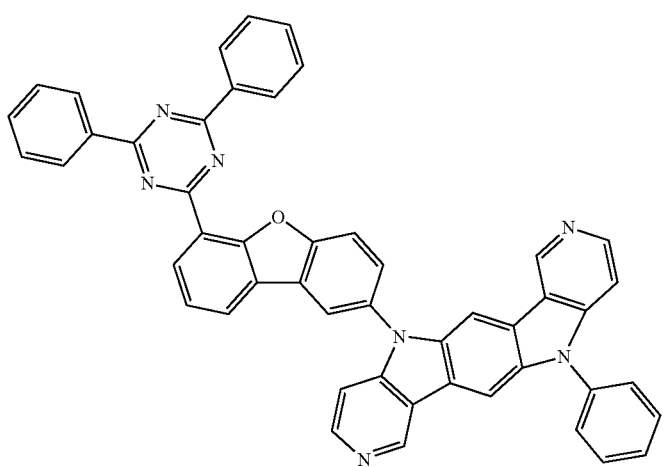

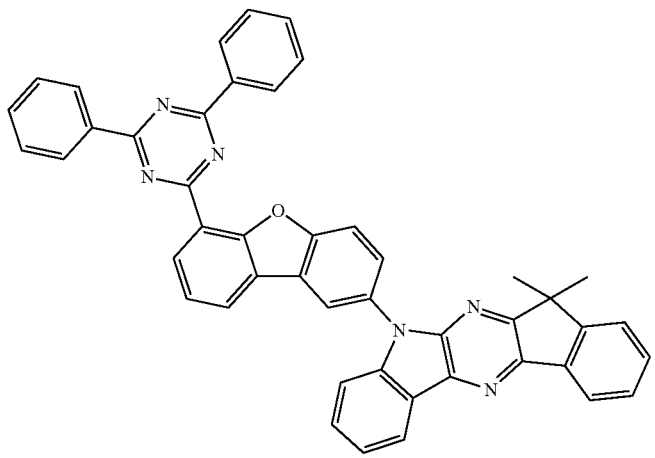
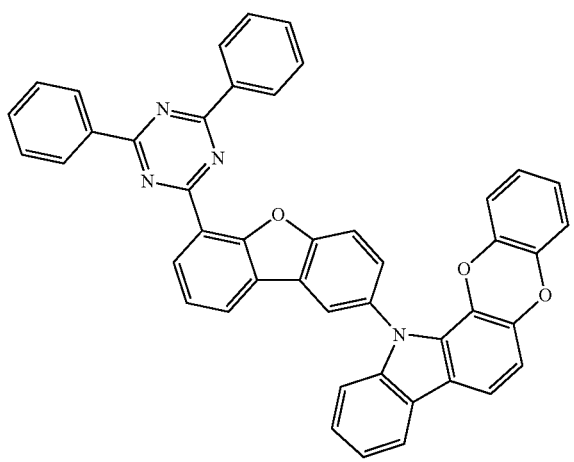
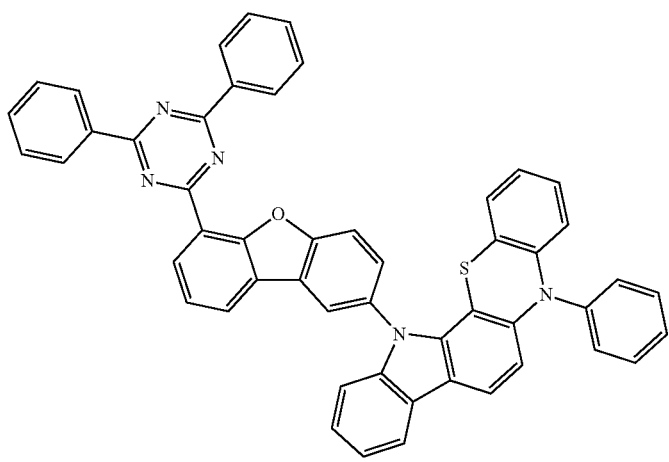

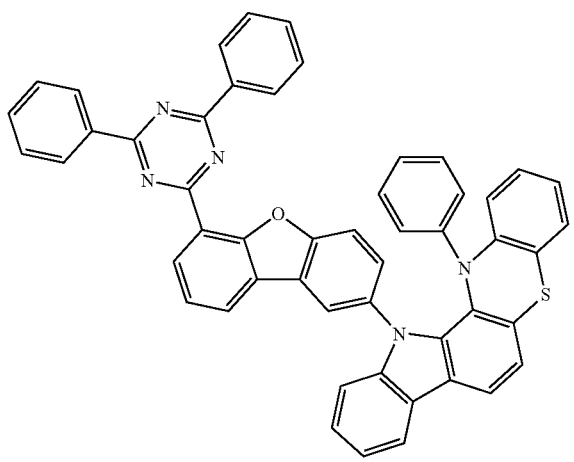
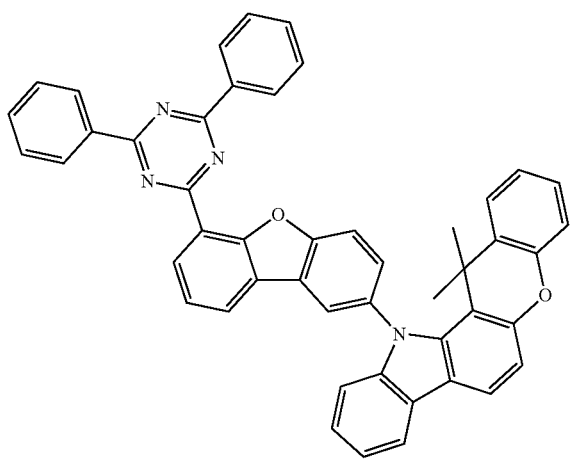
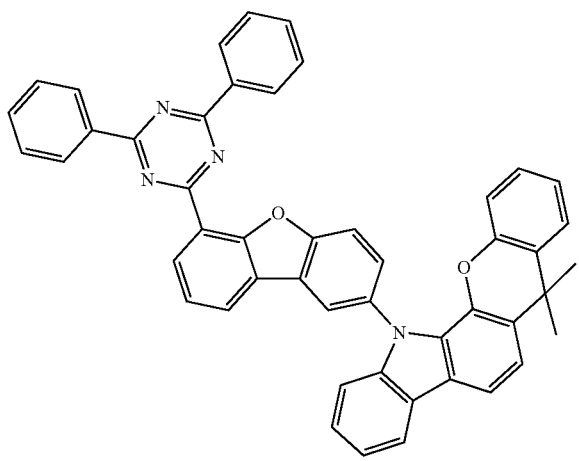

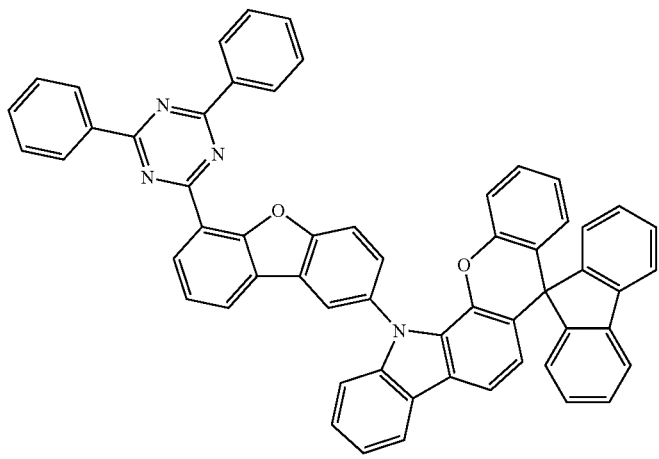
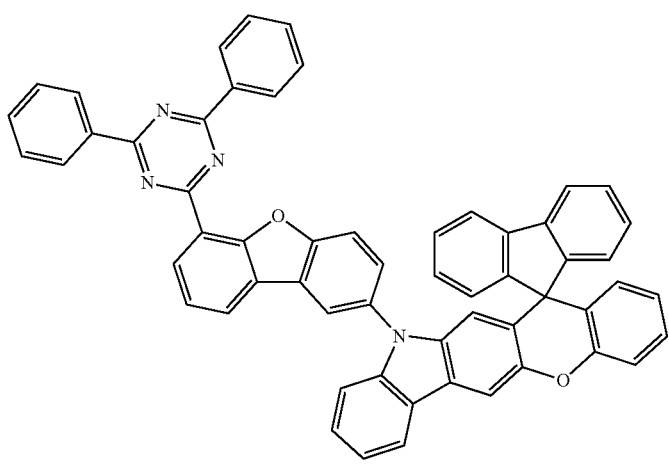
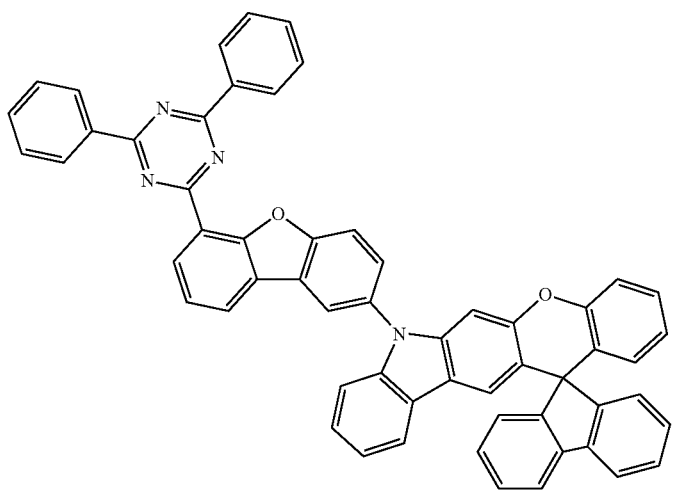

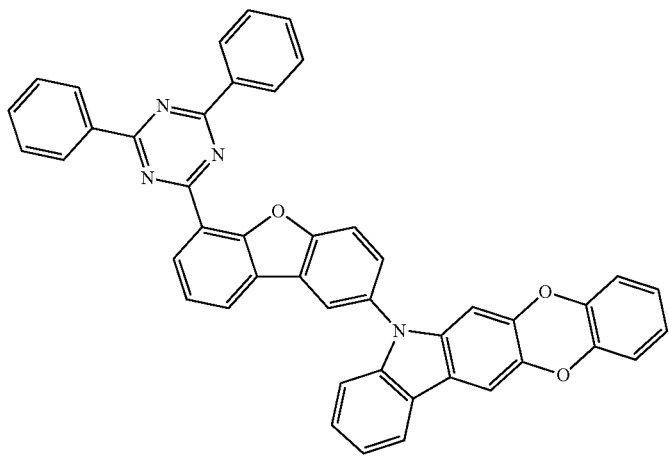
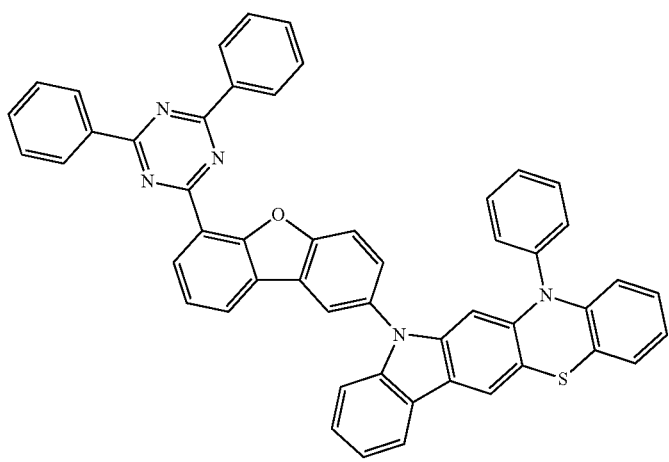
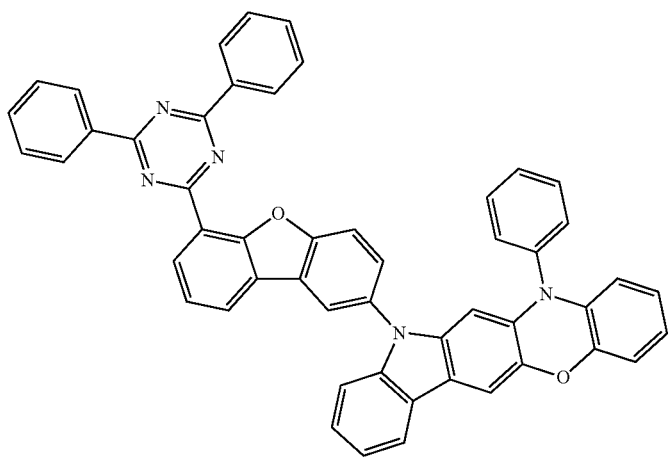

-continued
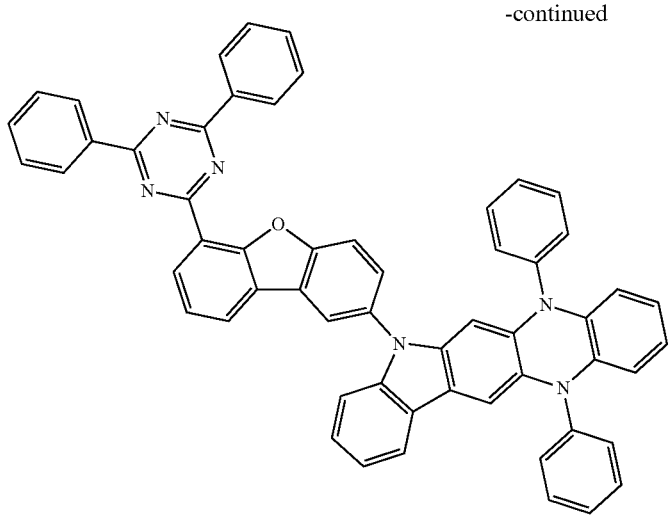
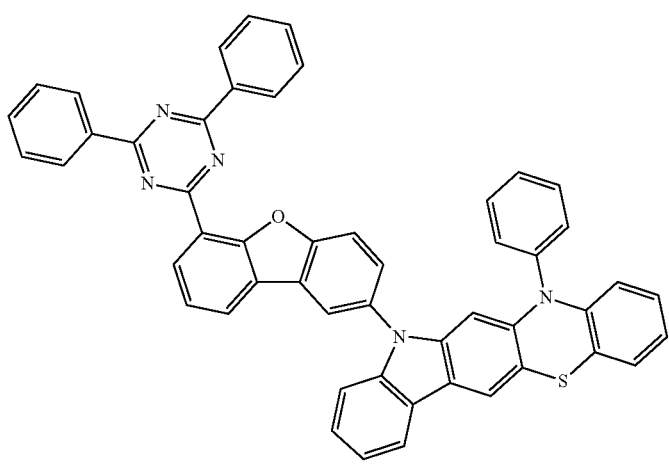
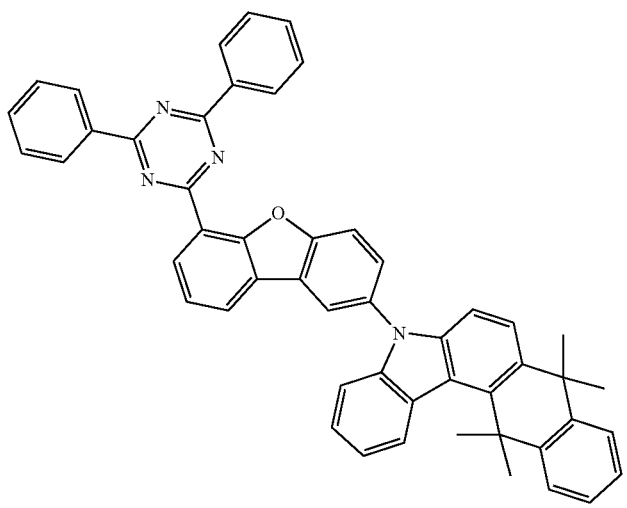

-continued
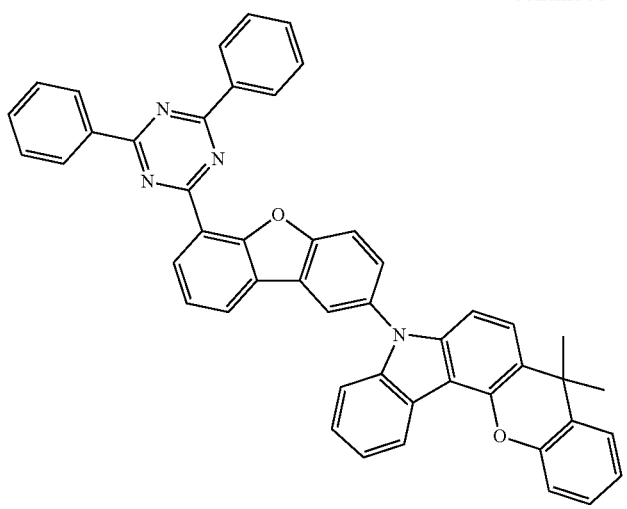
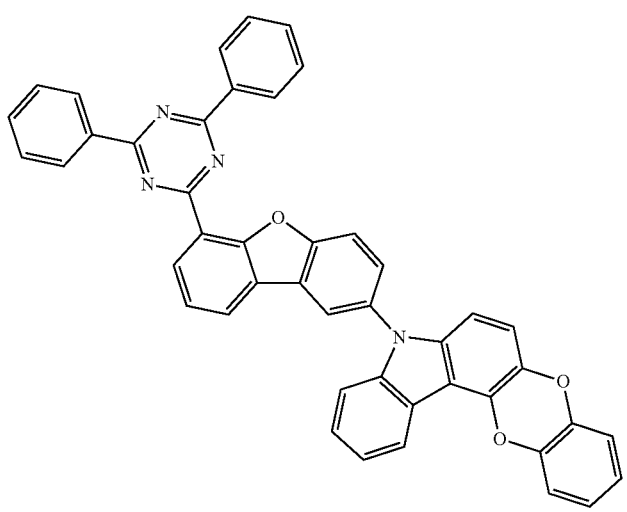
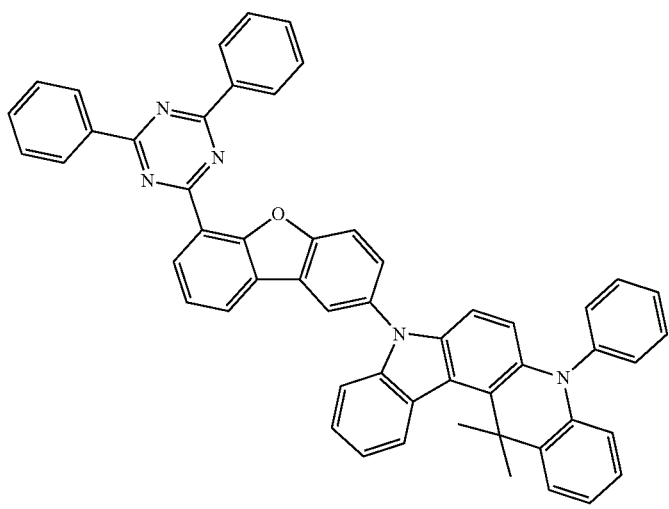

-continued
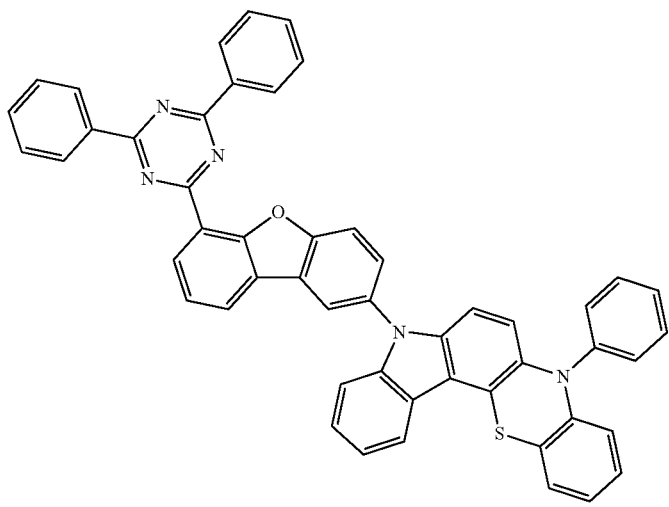
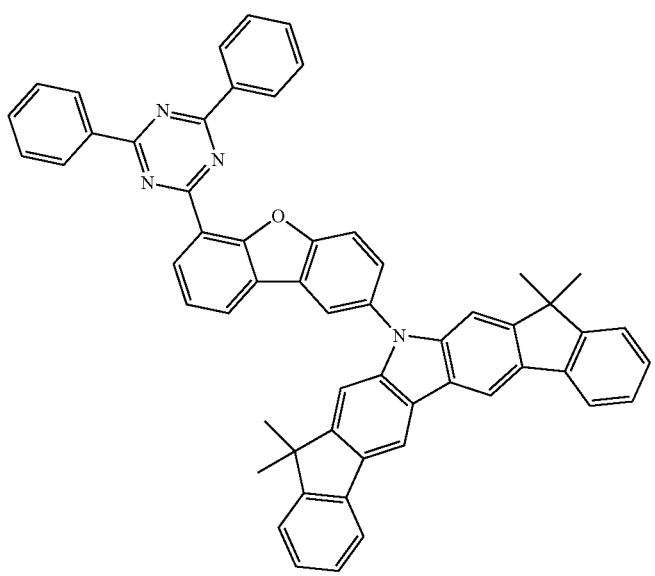
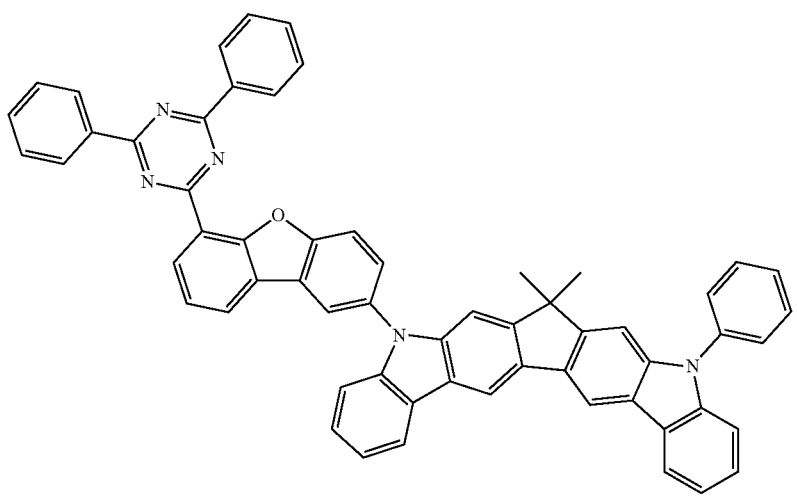

-continued
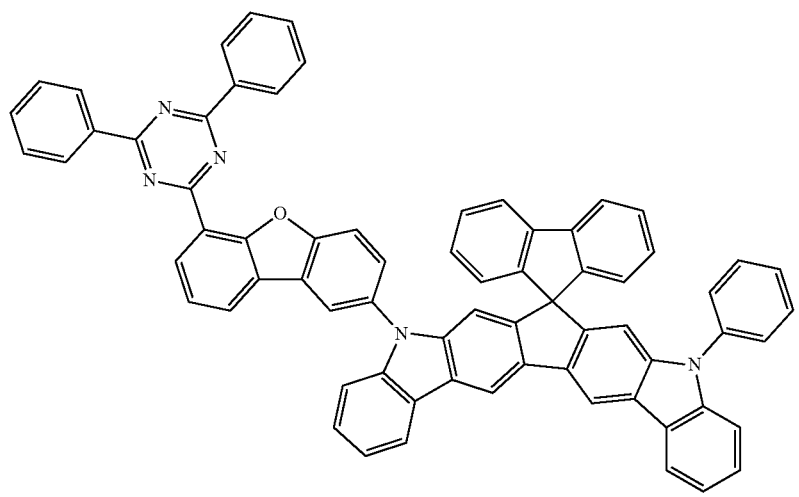
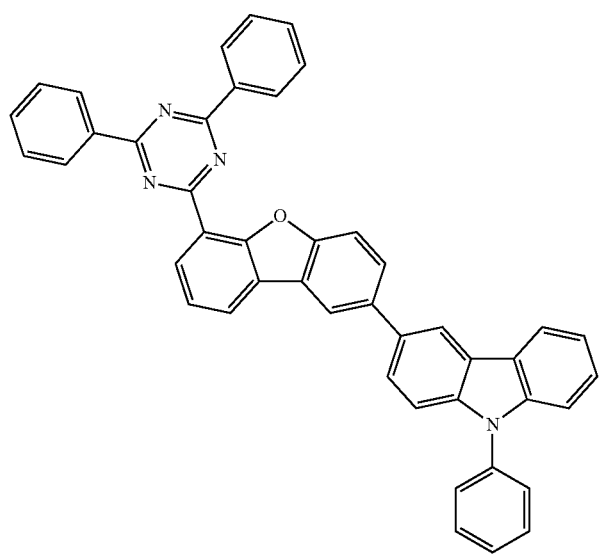
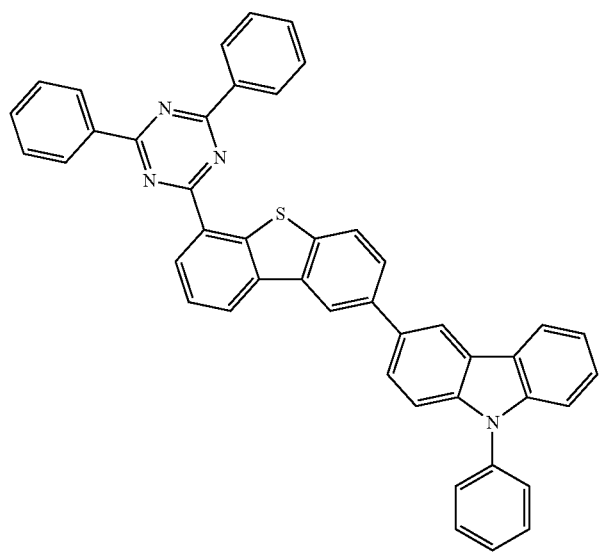

103
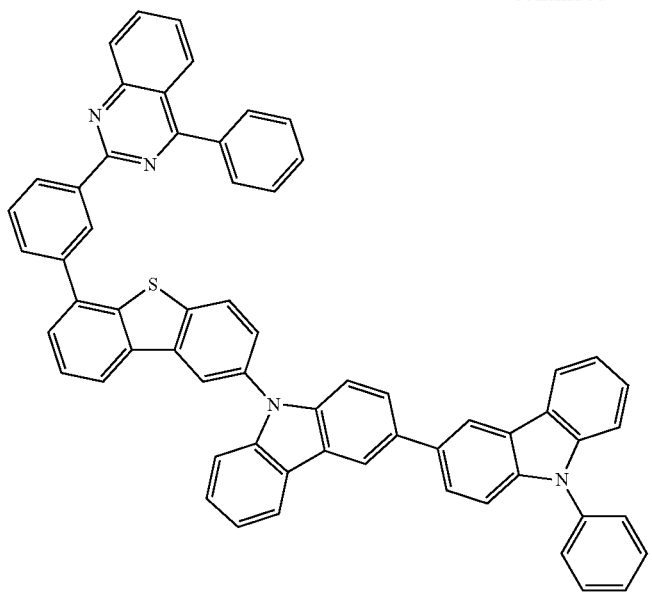
104
-continued
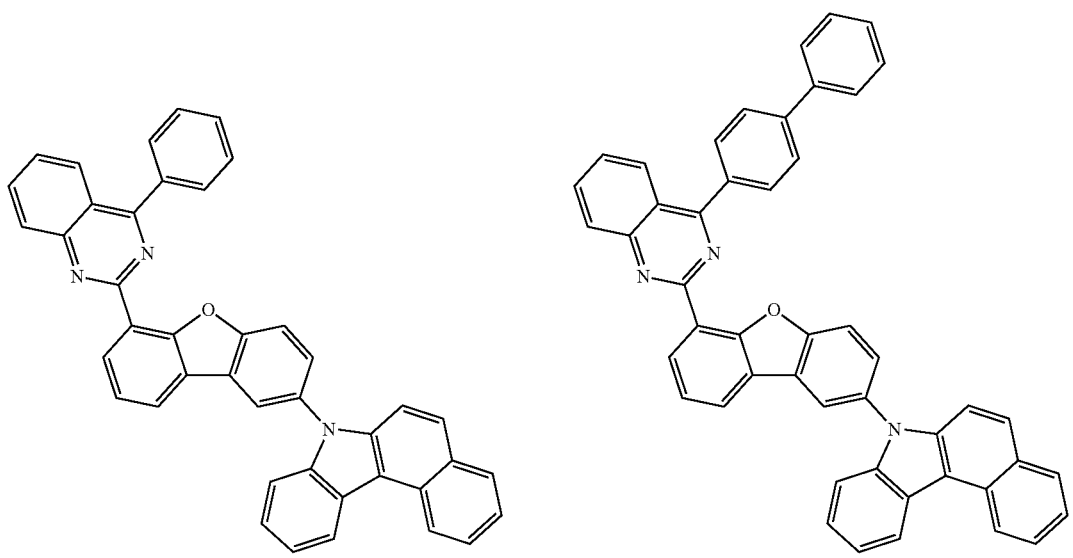

105
106
-continued
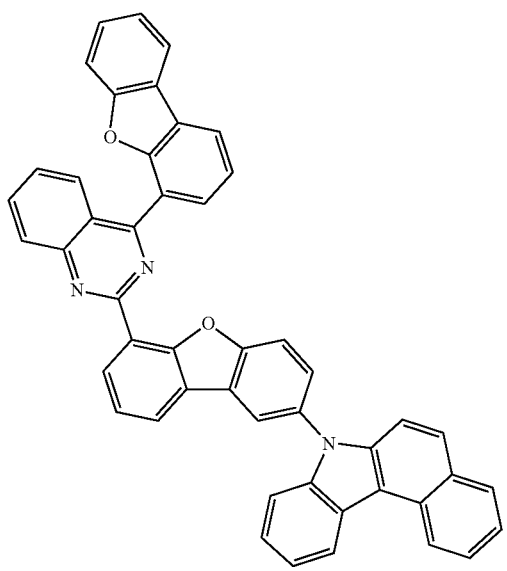
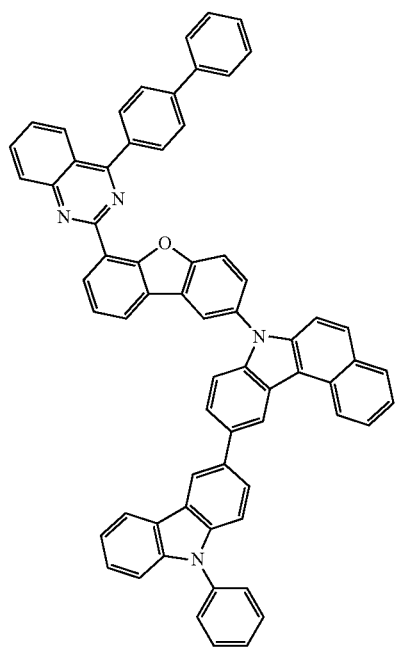
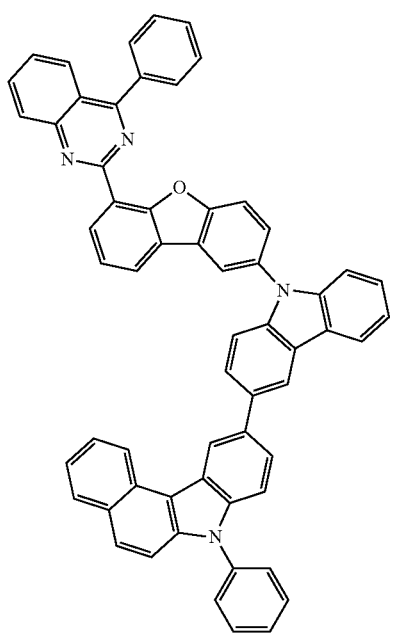
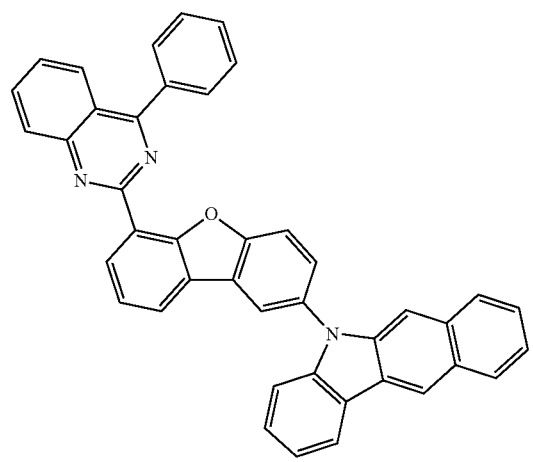

107
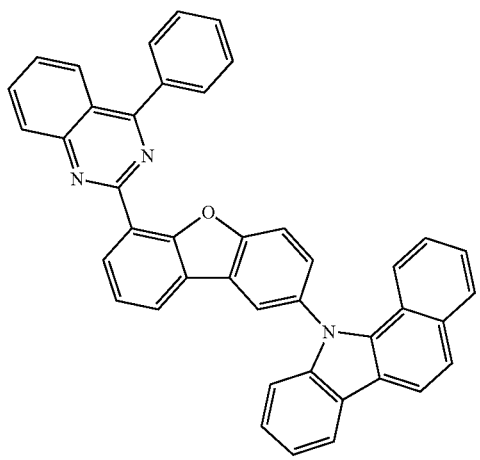
108
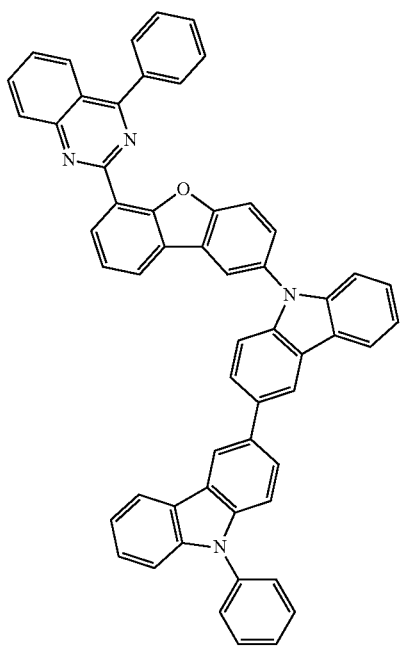
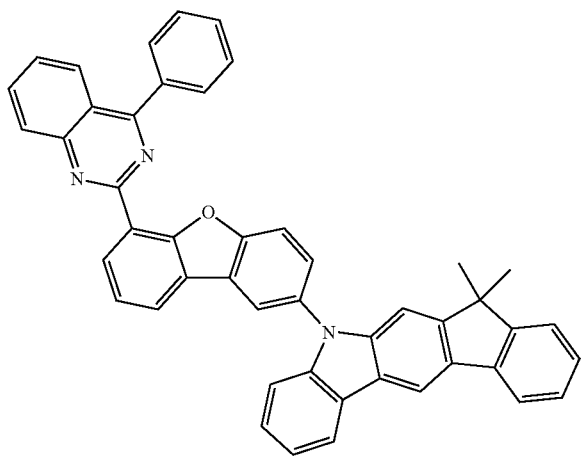
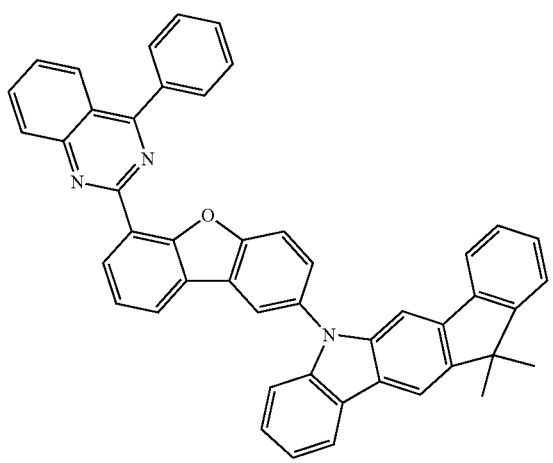
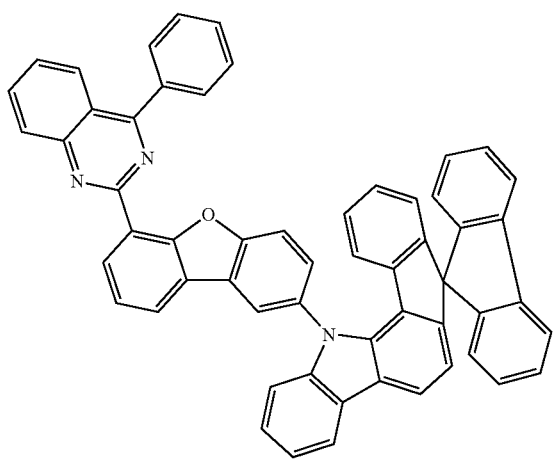

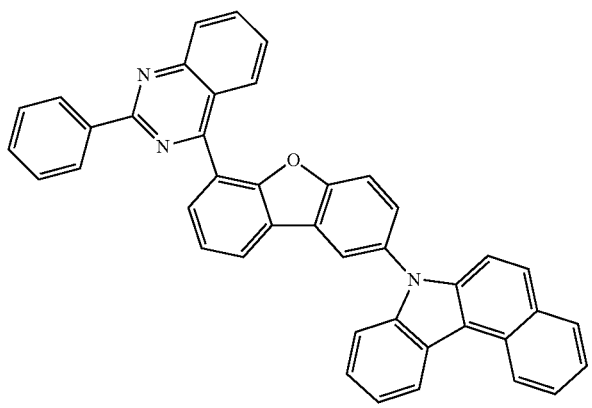
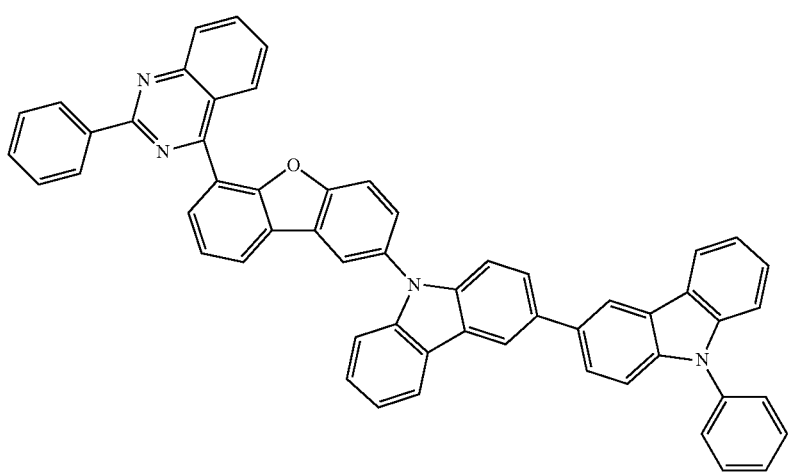
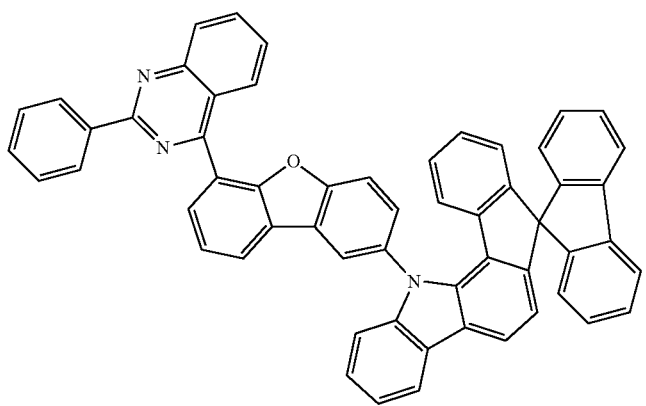

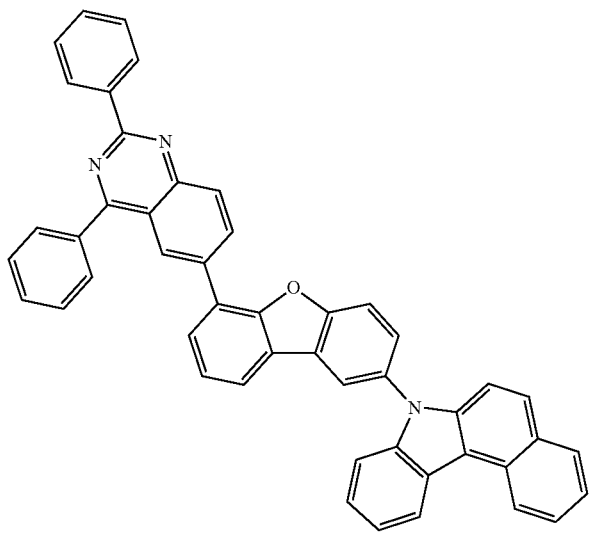
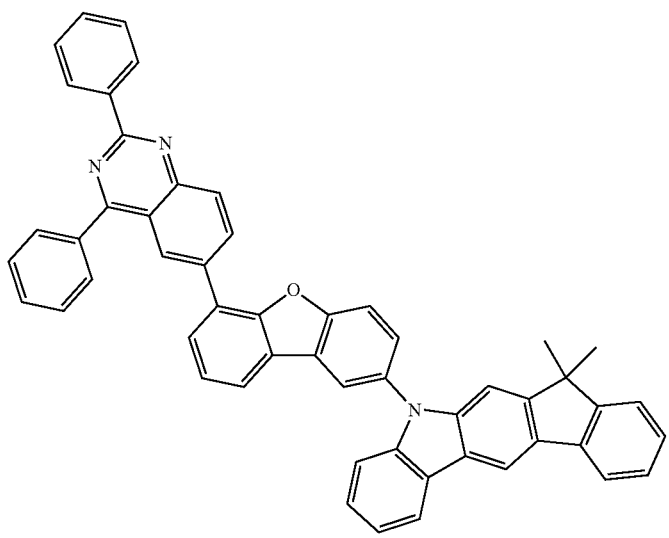
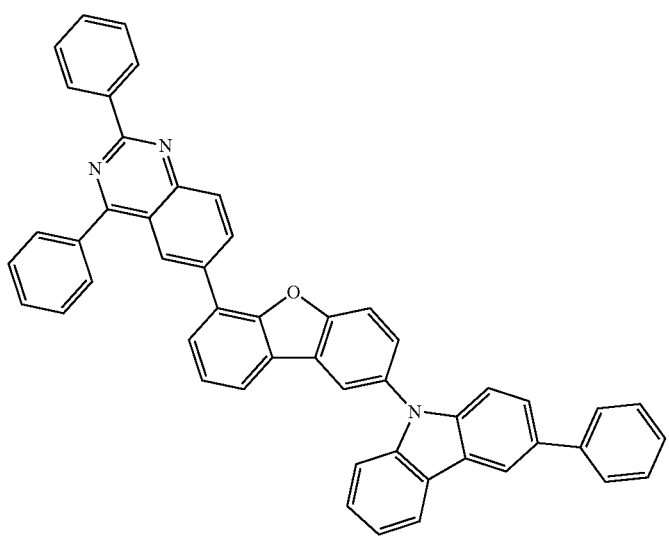

-continued
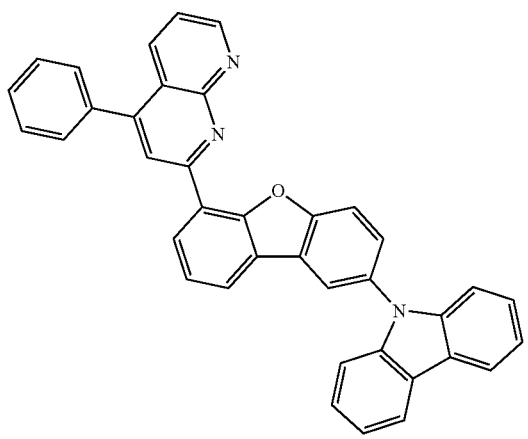
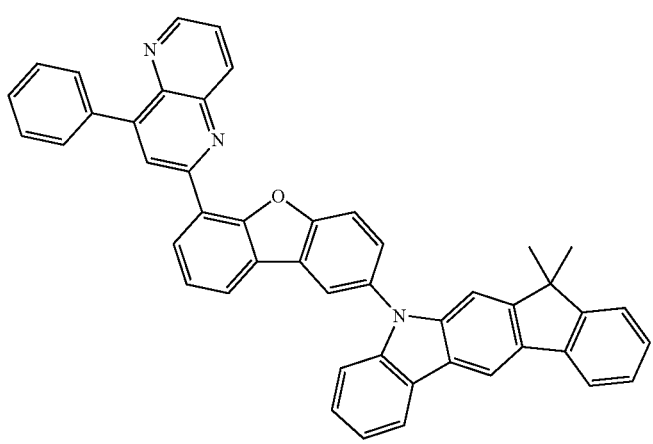
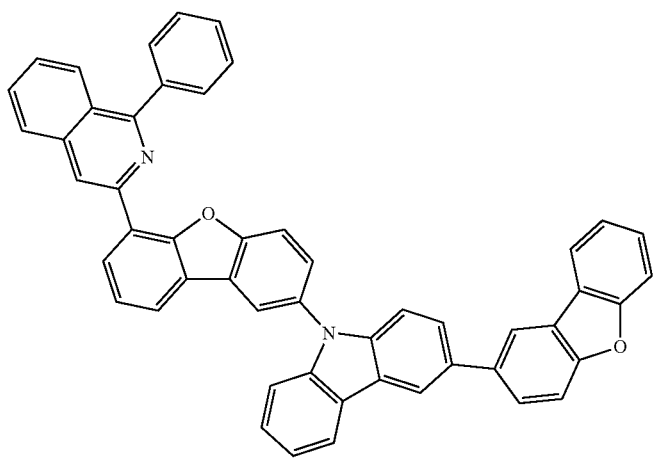

-continued
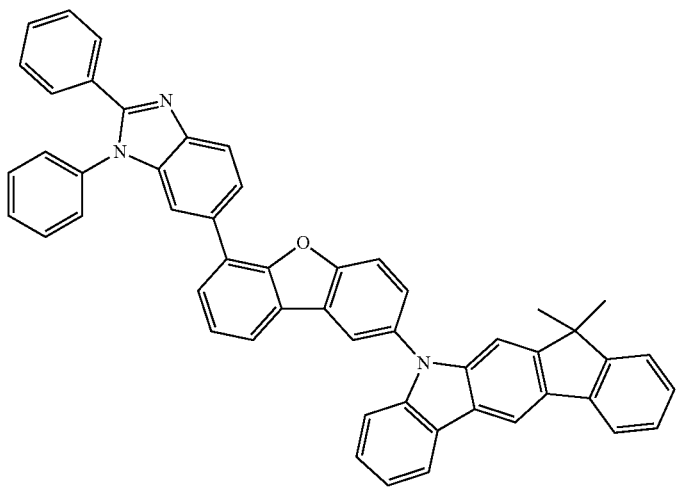
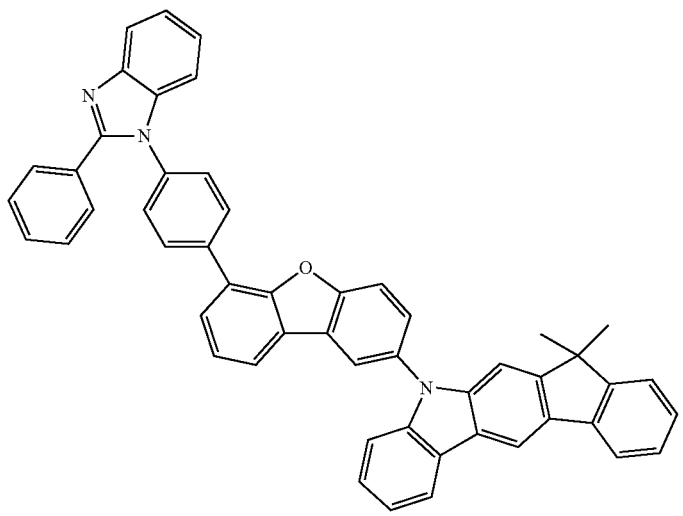
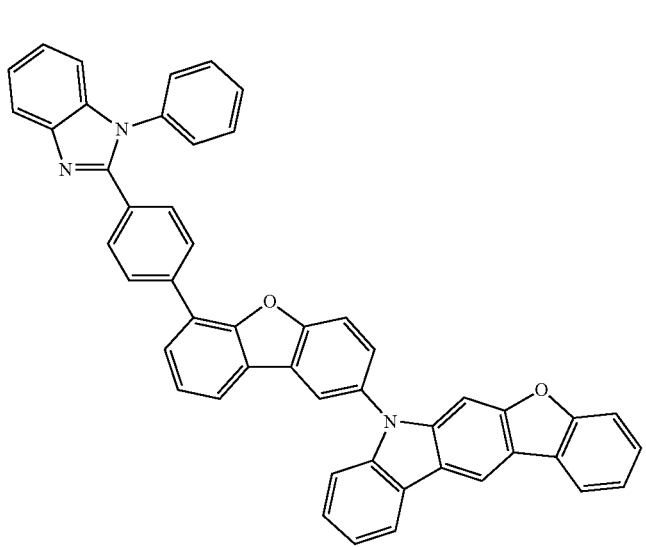

117 118
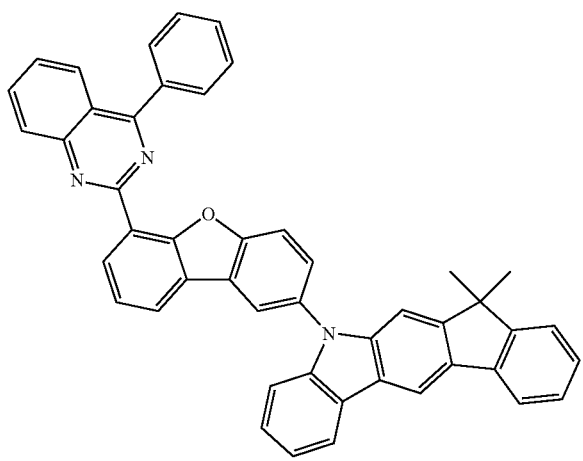
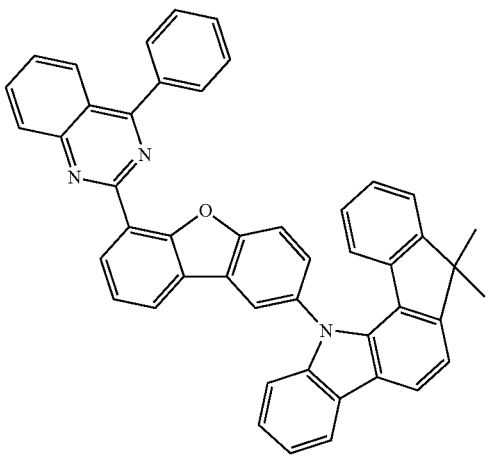
-continued
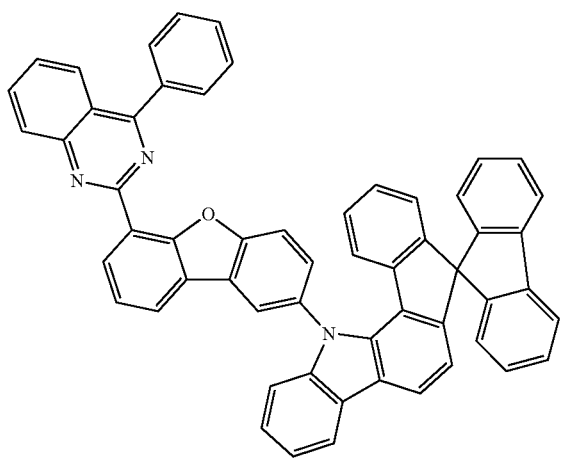
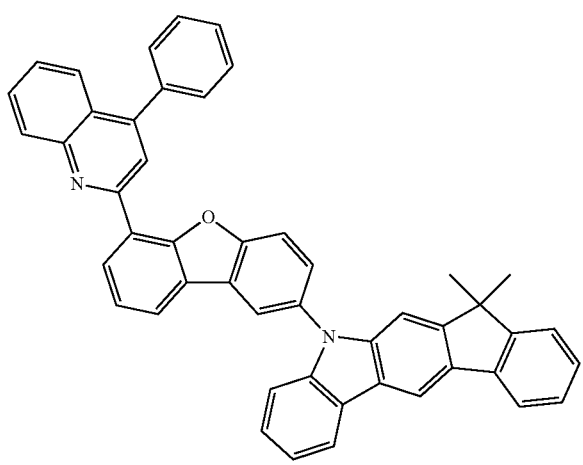
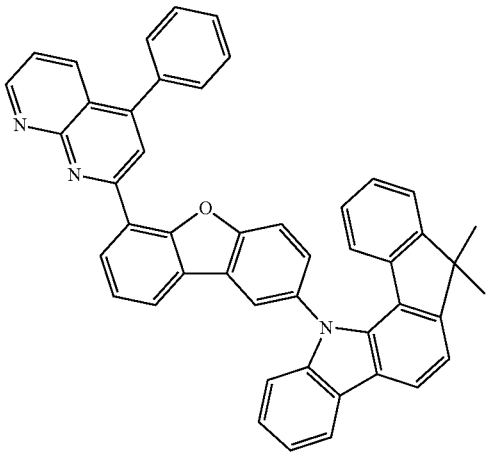

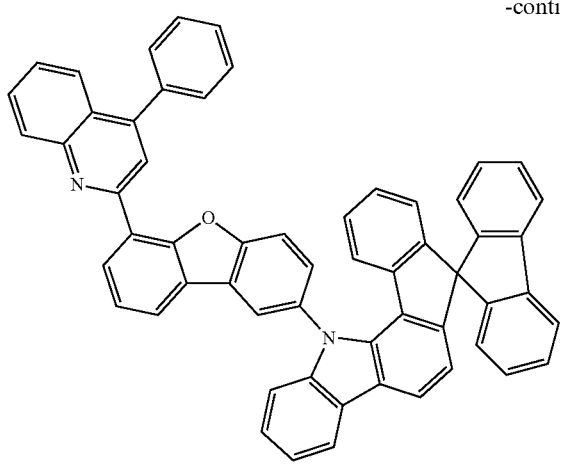

The invention furthermore relates to the use of a compound of the formula (1) in an electronic device, preferably in an electron-transporting layer and/or in an emitting layer The compounds according to the invention can also be used in a hole-transpaort layer.

The electronic device according to the invention is preferably selected from the group consisting of the organic integrated circuits (OICs), organic field-effect transistors (OFETs), organic thin-film transistors (OTFTs), organic light-emitting transistors (OLETs), organic solar cells (OSCs), organic optical detectors, organic photoreceptors, organic field-quench devices (OFQDs), organic light-emitting electrochemical cells (OLECs, LECs or LEECs), organic laser diodes (O-lasers) and organic light-emitting diodes (OLEDs). Particular preference is given here to organic electroluminescent devices, very particularly preferably OLECs and OLEDs and in especially preferably OLEDs.

OLEDs in the sense of the present invention are taken to mean both organic light-emitting diodes comprising small organic molecules (SMOLEDs) and also polymeric light-emitting diodes (PLEDs), where SMOLEDs represent preferred OLEDs.

The organic layer comprising the compound of the formula (1) is preferably a layer having an electron-transporting function. It is particularly preferably an electron-injection layer (EIL), an electron-transport layer (ETL), a hole-blocking layer (HBL) or an emitting layer (EML), where it is more preferred if this compound is present in an emitting layer.

A hole-transport layer in accordance with the present application is a layer having a hole-transporting function which is located between the anode and the emitting layer.

An electron-transport layer in accordance with the present application is a layer having an electron-transporting function which is located between the cathode and the emitting layer.

Hole-injection layers and electron-blocking layers in the sense of the present invention are taken to be special embodiments of hole-transport layers. In the case of a plurality of hole-transport layers between anode and emitting layer, a hole-injection layer is a hole-transport layer which is directly adjacent to the anode or is only separated therefrom by a single coating of the anode. In the case of a plurality of hole-transport layers between anode and emitting layer, an electron-blocking layer is the hole-transport layer which is directly adjacent to the emitting layer on the anode side.

As already mentioned above, the compound of the formula (1) is, in a preferred embodiment, employed as matrix material in an emission layer of an organic electronic device, in particular in an organic electroluminescent device, for example in an OLED or OLEC. The matrix material of the formula (1) is present in the electronic device here in combination with one or more dopants, preferably phosphorescent dopants.

The term phosphorescent dopants typically encompasses compounds in which the light emission takes place through a spin-forbidden transition, for example through a transition from an excited triplet state or a state having a relatively high spin quantum number, for example a quintet state.

Suitable phosphorescent dopants are, in particular, compounds which emit light, preferably in the visible region, on suitable excitation and in addition contain at least one atom having an atomic number greater than 20, preferably greater than 38 and less than 84, particularly preferably greater than 56 and less than 80. The phosphorescent emitters used are preferably compounds which contain copper, molybdenum, tungsten, rhenium, ruthenium, osmium, rhodium, iridium, palladium, platinum, silver, gold or europium, in particular compounds which contain iridium, platinum or copper.

All luminescent iridium, platinum or copper complexes are regarded as phosphorescent compounds in the sense of the present application. Examples of phosphorescent dopants are given in a following section.

A dopant in a system comprising a matrix material and a dopant is taken to mean the component whose proportion in the mixture is the smaller. Correspondingly, a matrix material in a system comprising a matrix material and a dopant is taken to mean the component whose proportion in the mixture is the larger.

The proportion of the matrix material in the emitting layer in this case is between 50.0 and 99.9% by vol., preferably between 80.0 and 99.5% by vol. and particularly preferably between 92.0 and 99.5% by vol. for fluorescent emitting layers and between 85.0 and 97.0% by vol. for phosphorescent emitting layers.

Correspondingly, the proportion of the dopant is between 0.1 and 50.0% by vol., preferably between 0.5 and 20.0% by vol. and particularly preferably between 0.5 and 8.0% by vol. for fluorescent emitting layers and between 3.0 and 15.0% by vol. for phosphorescent emitting layers.

An emitting layer of an organic electroluminescent device may also comprise systems comprising a plurality of matrix materials (mixed-matrix systems) and/or a plurality of dopants. In this case too, the dopants are generally the materials whose proportion in the system is the smaller and the matrix materials are the materials whose proportion in the system is the greater. In individual cases, however, the proportion of an individual matrix material in the system may be smaller than the proportion of an individual dopant.

In a further preferred embodiment of the invention, the compounds of the formula (1) are used as a component of mixed-matrix systems. The mixed-matrix systems preferably comprise two or three different matrix materials, particularly preferably two different matrix materials. One of the two materials here is preferably a material having hole-transporting properties and the other material is a material having electron-transporting properties. However, the desired electron-transporting and hole-transporting properties of the mixed-matrix components may also be combined principally or completely in a single mixed-matrix components, where the further mixed-matrix component(s) fulfil other functions. The two different matrix materials here may be present in a ratio of 1:50 to 1:1, preferably 1:20 to 1:1, particularly preferably 1:10 to 1:1 and very particularly preferably 1:4 to 1:1. Mixed-matrix systems are preferably employed in phosphorescent organic electroluminescent devices. More precise information on mixed-matrix systems is given, inter alia, in the application WO 2010/108579.

Particularly suitable matrix materials which can be used as matrix components of a mixed-matrix system in combination with the compounds according to the invention are selected from the preferred matrix materials for phosphorescent dopants indicated below or the preferred matrix materials for fluorescent dopants, depending on what type of dopant is employed in the mixed-matrix system.

The present invention therefore also relates to a composition comprising at least one compound of the formula (1) and at least one further matrix material. Preferred further matrix materials are the matrix materials mentioned below.

The present invention also relates to a composition comprising at least one compound of the formula (1) and at least one wide band gap material, where a wide band gap material is taken to mean a material in the sense of the disclosure of U.S. Pat. No. 7,294,849. These systems exhibit particularly advantageous performance data in electroluminescent devices. It is particularly preferred if the band gap of the wide band gap material is 3.5 eV or more, where band gap is taken to mean the energy difference between HOMO and LUMO. The orbital energies are determined by the method describe above The present invention furthermore relates to a composition comprising at least one compound of the formula (1) and at least one further organic semiconductor material selected from the group consisting of fluorescent emitters, phosphorescent emitters, host materials, matrix materials, electron-transport materials, electron-injection materials, hole-conductor materials, hole-injection materials, electron-blocking materials and hole-blocking materials.

Preferred phosphorescent dopants for use in mixed-matrix systems are the preferred phosphorescent dopants indicated below.

Examples of phosphorescent dopants are revealed by the applications WO 2000/70655, WO 2001/41512, WO 2002/02714, WO 2002/15645, EP 1191613, EP 1191612, EP 1191614, WO 2005/033244, WO 2005/019373 and US 2005/0258742. In general, all phosphorescent complexes as are used in accordance with the prior art for phosphorescent OLEDs and as are known to the person skilled in the art in the area of organic electroluminescent devices are suitable for use in the devices according to the invention.

Explicit examples of phosphorescent dopants are shown in the following table

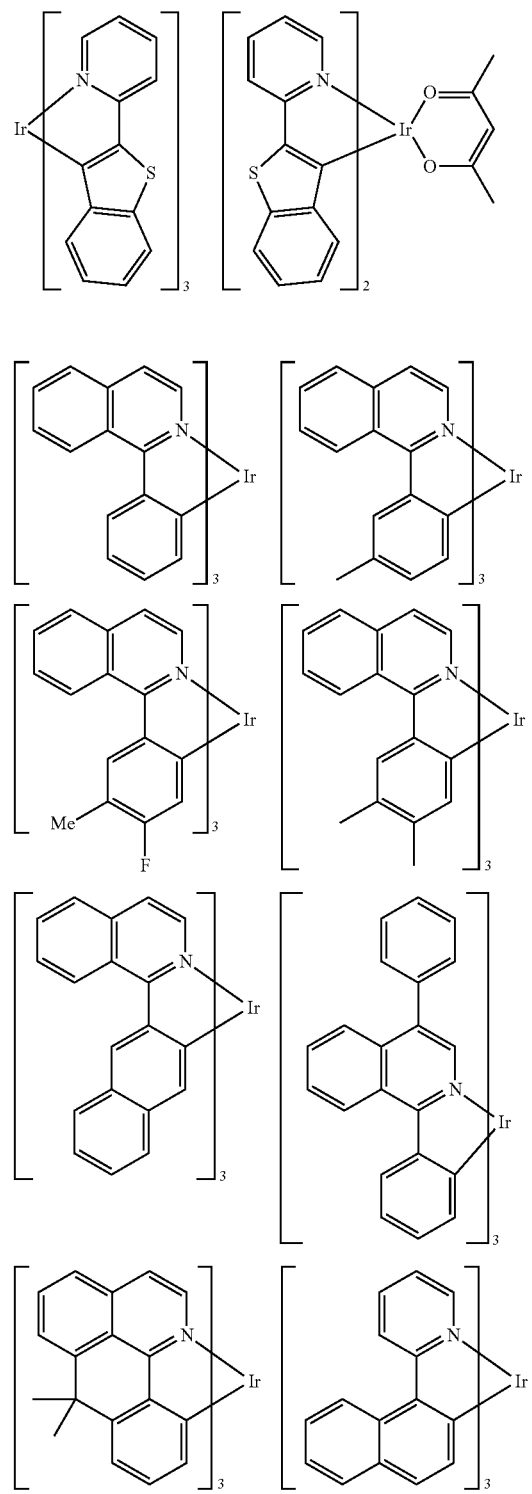

123
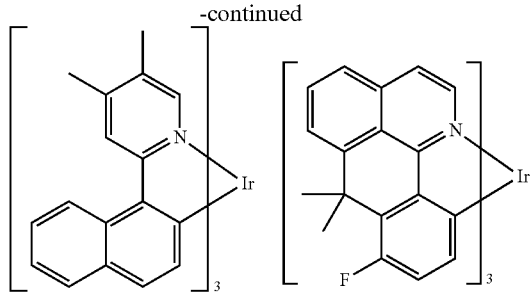
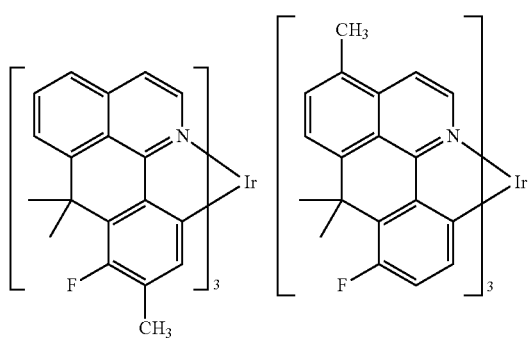
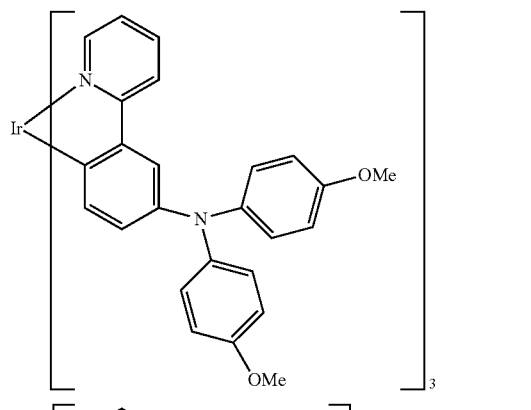
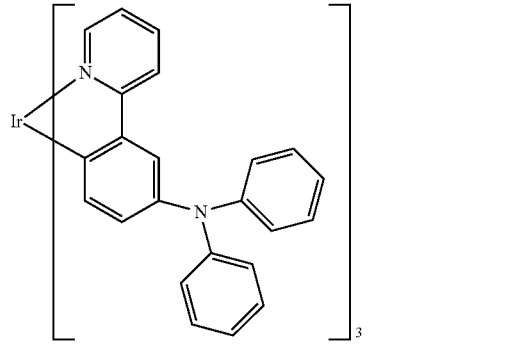
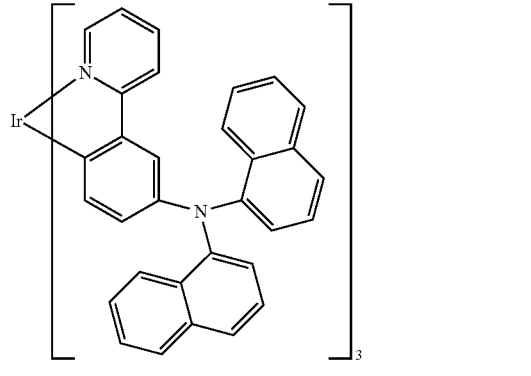
124
-continued
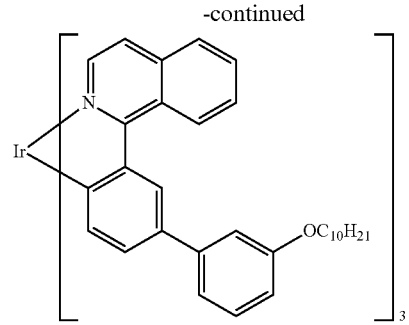
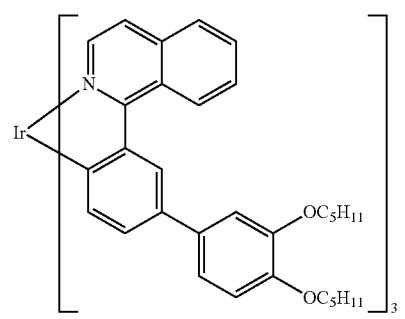
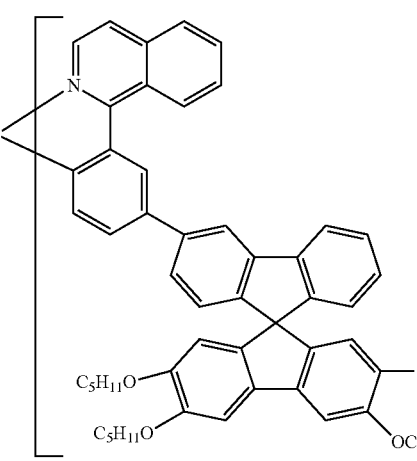
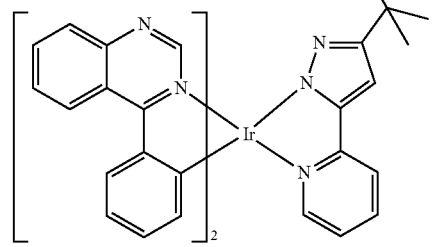
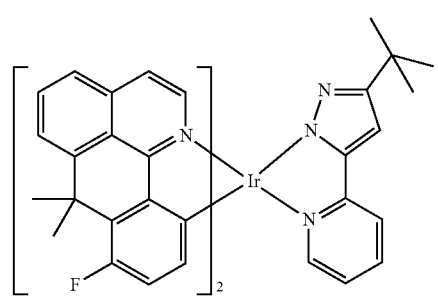

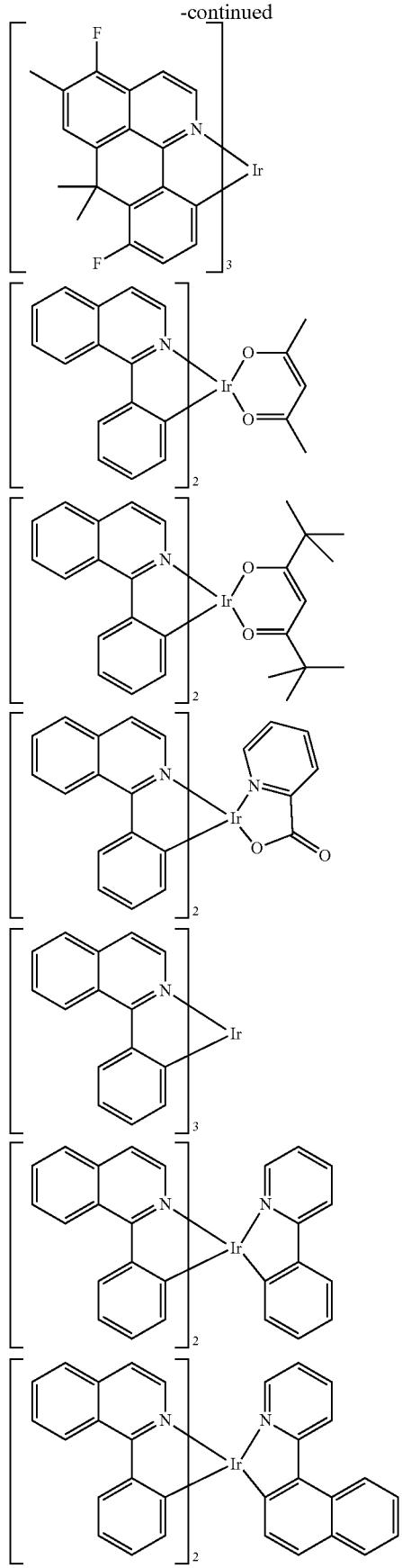
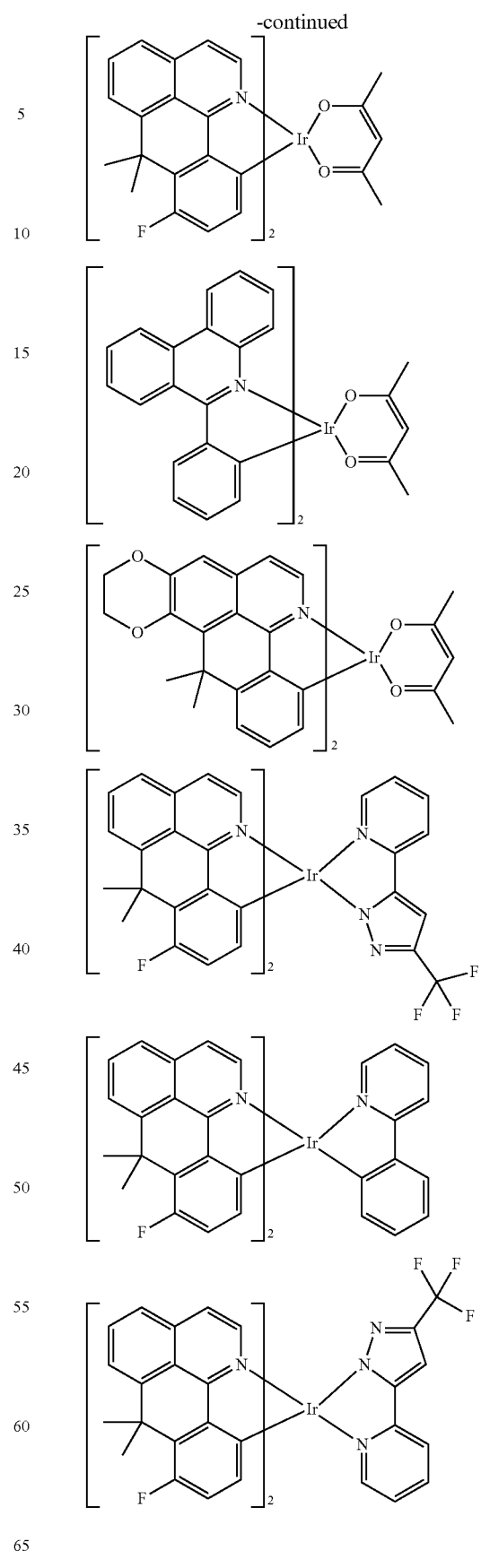

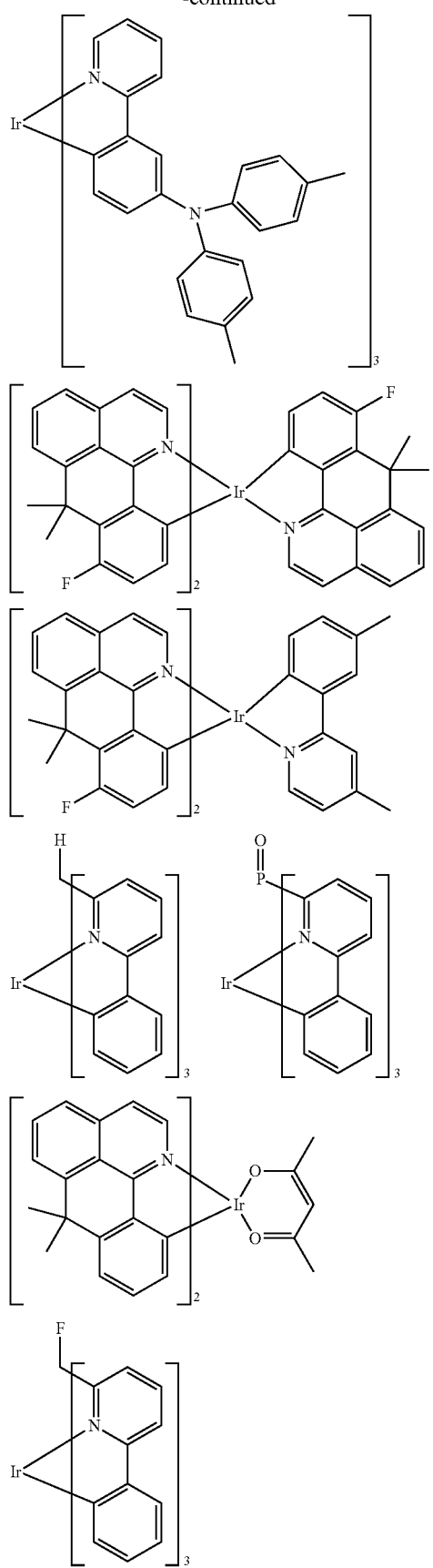
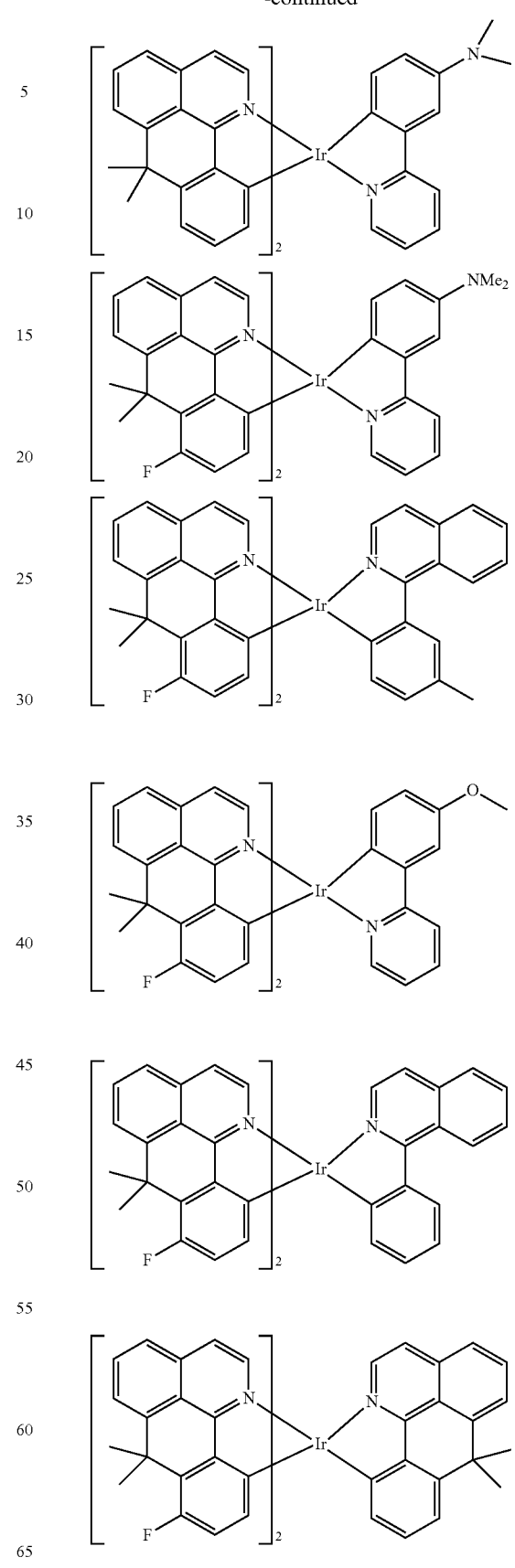

129
-continued
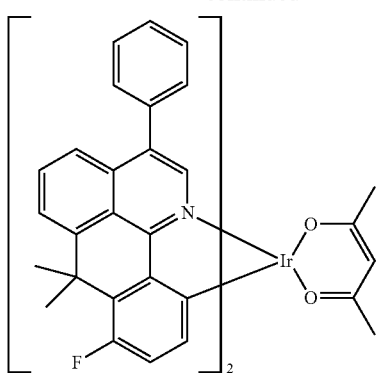
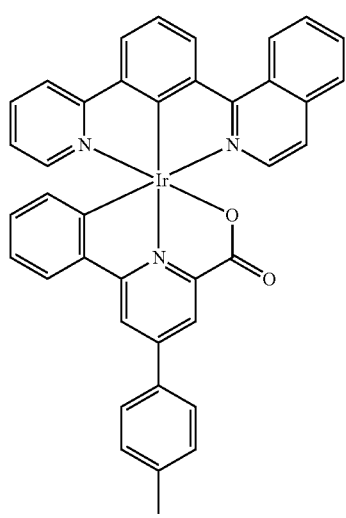
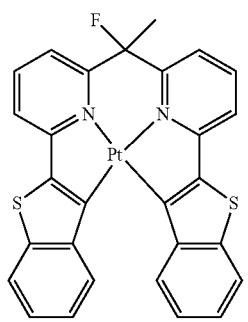
130
-continued
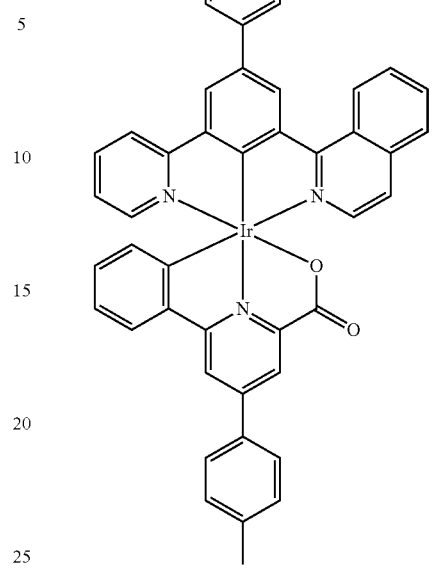
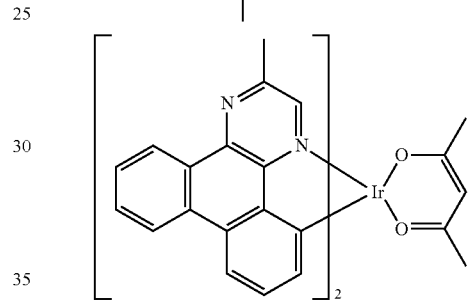
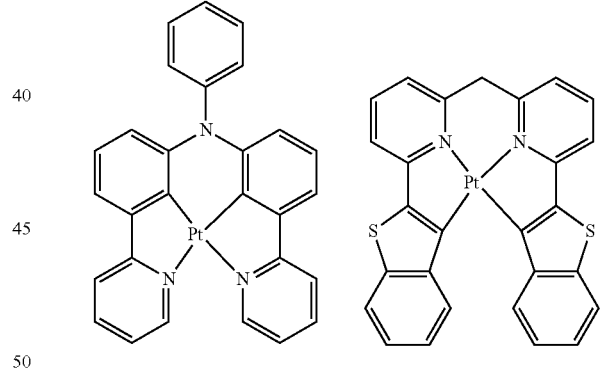
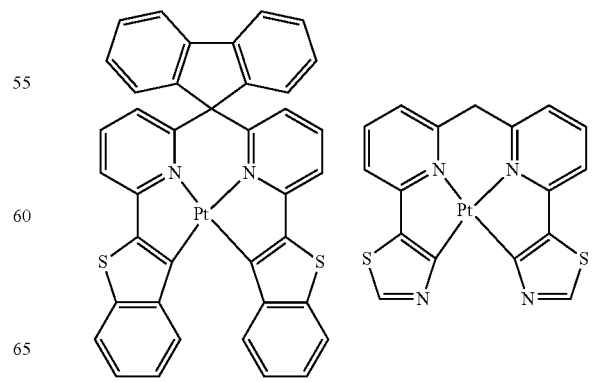

-continued
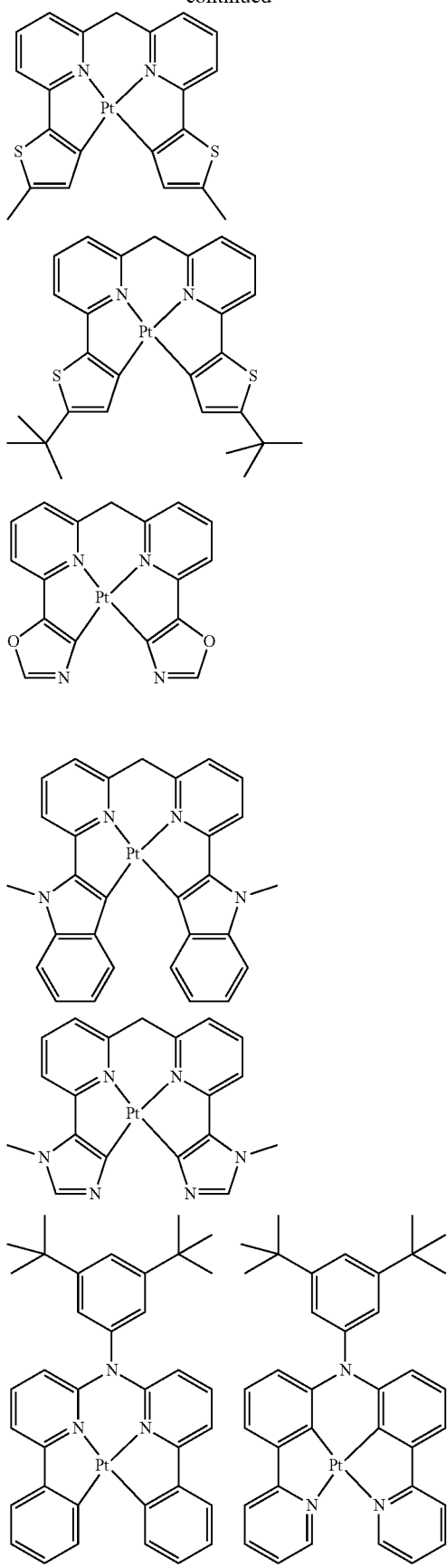
-continued
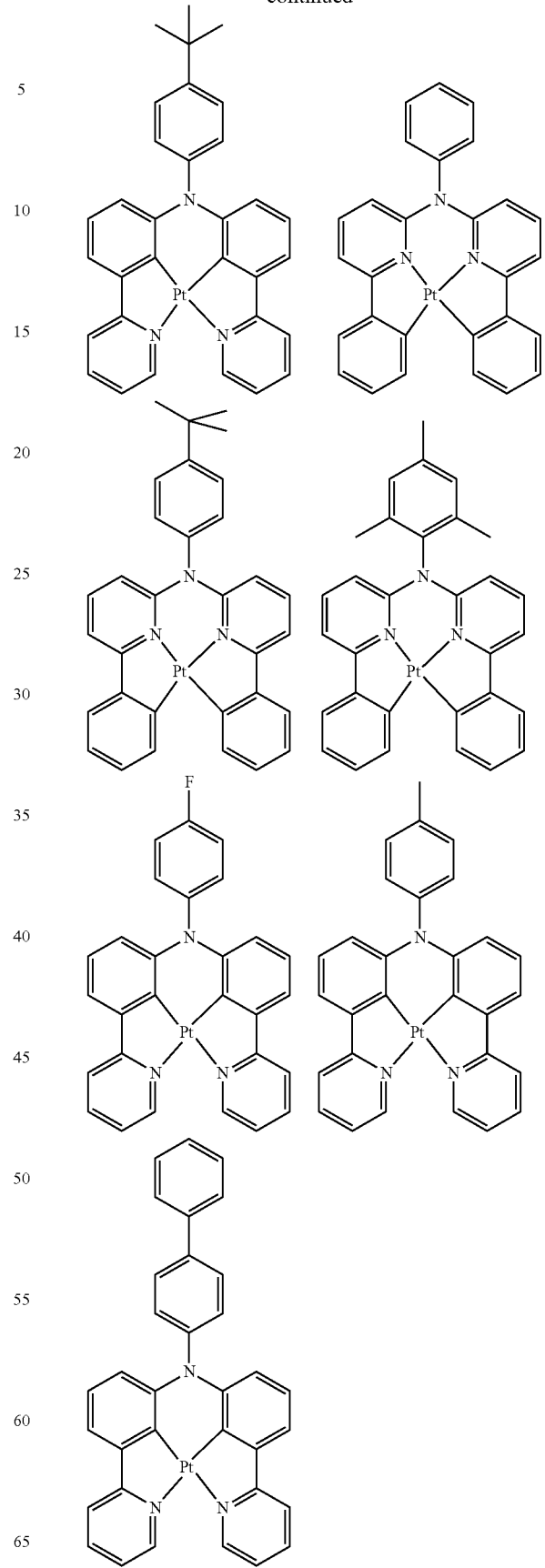

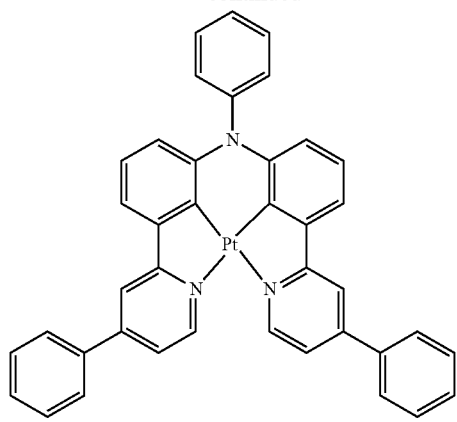
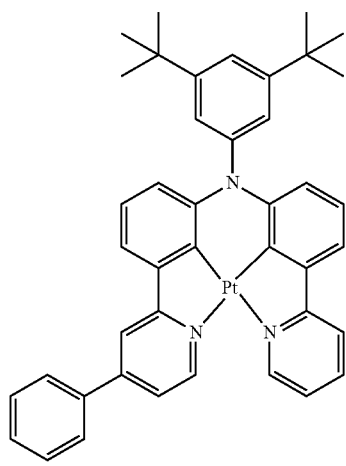
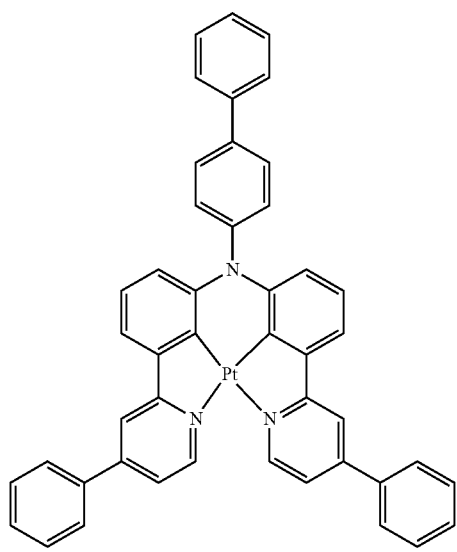
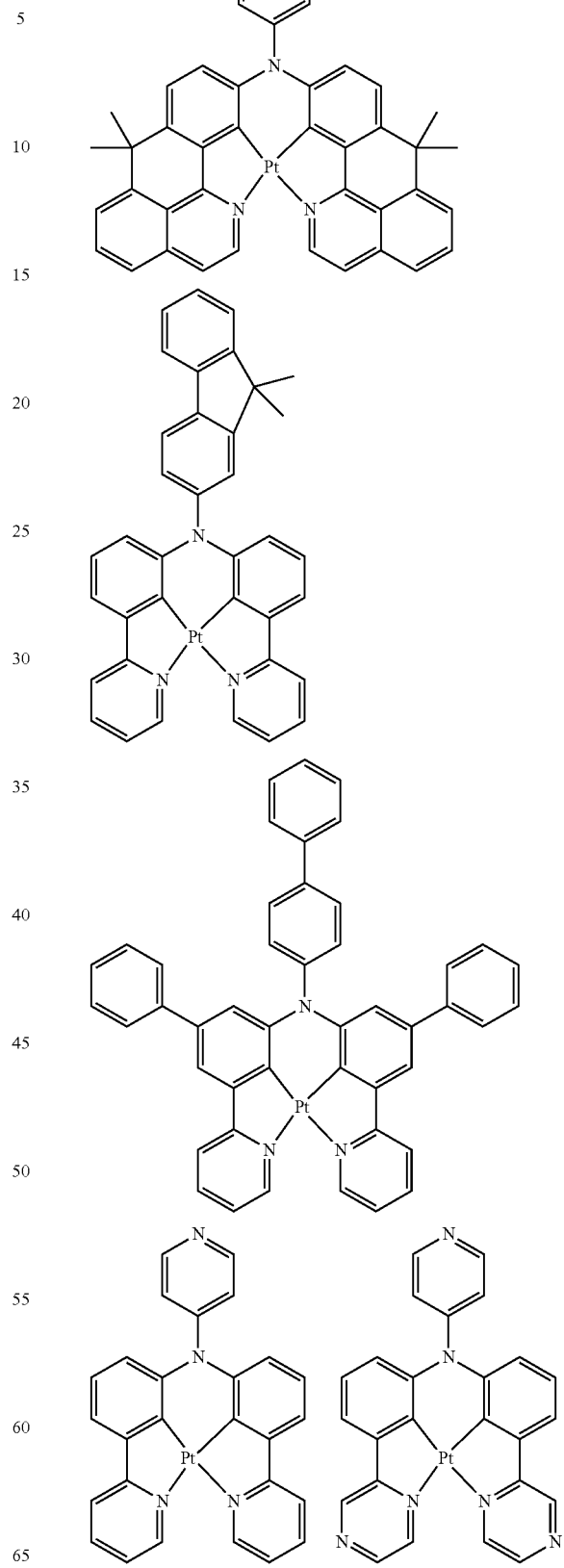

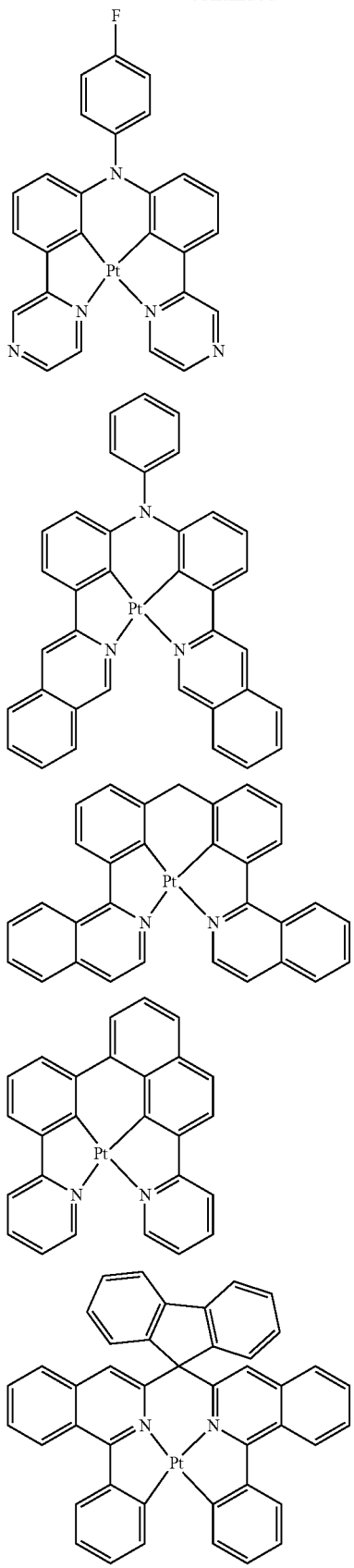
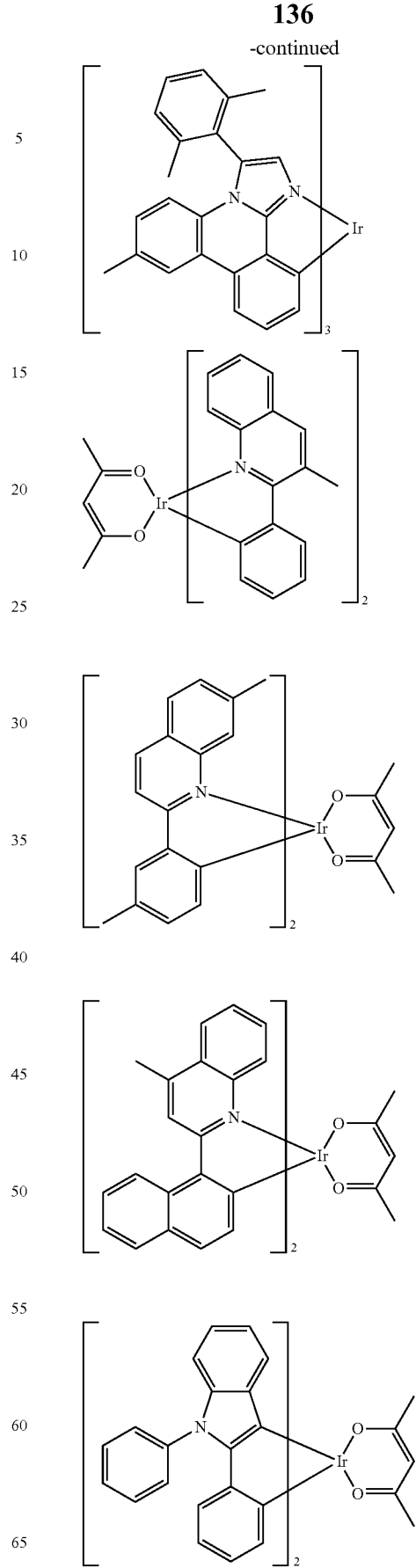

137
-continued
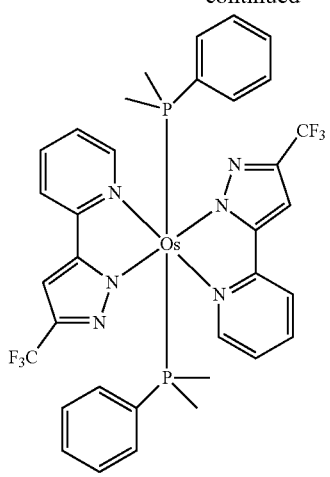
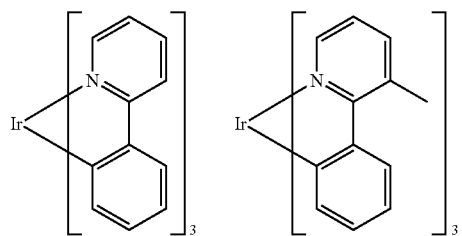
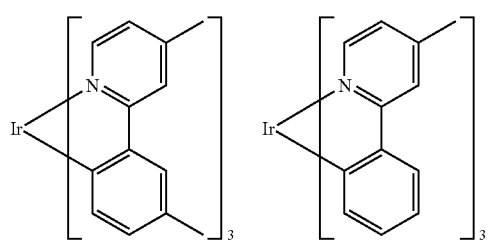
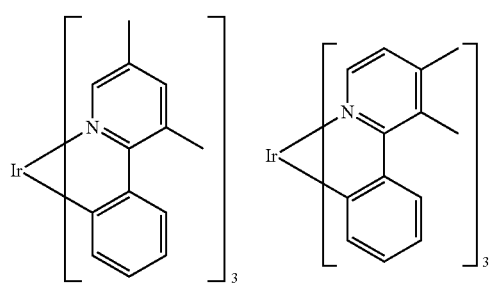
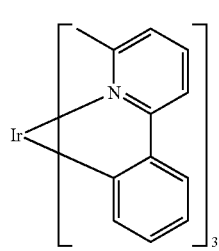
138
-continued
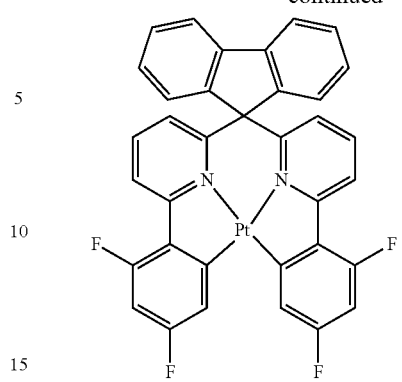
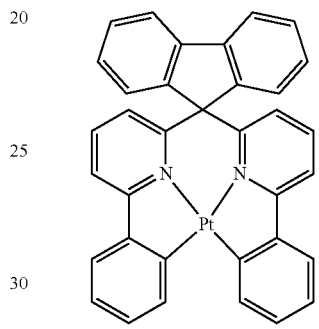
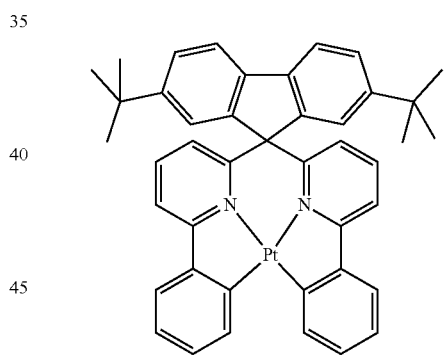
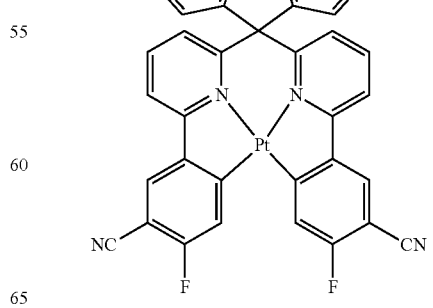

139
-continued
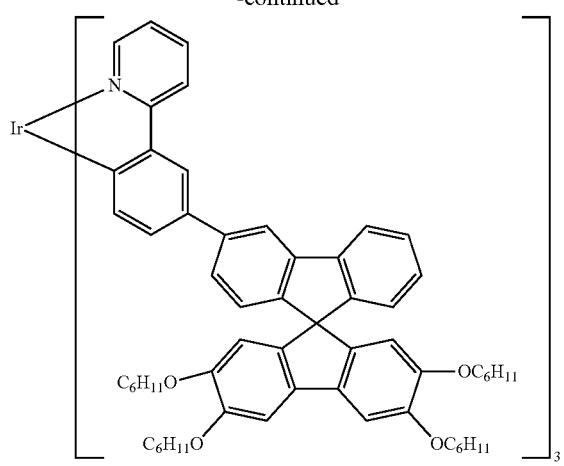
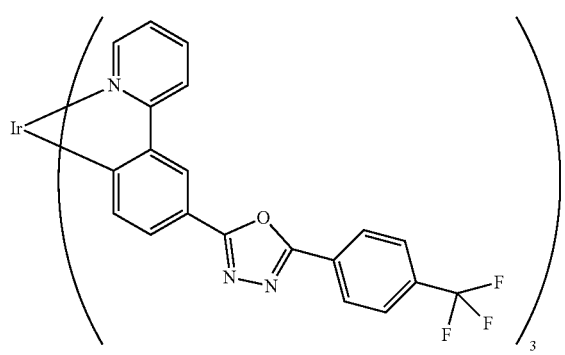
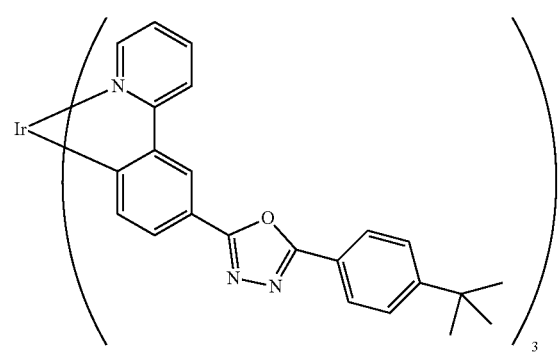
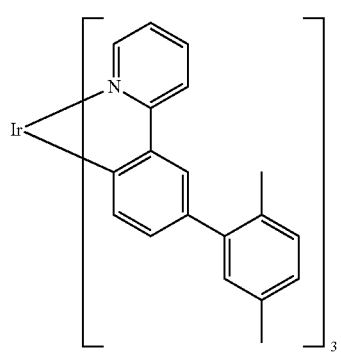
140
-continued
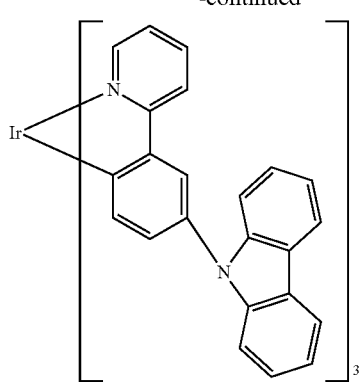
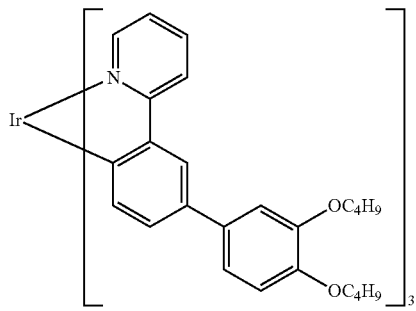
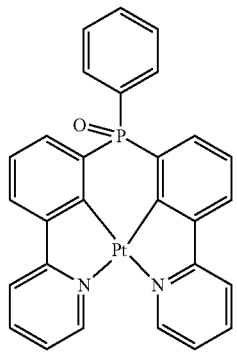
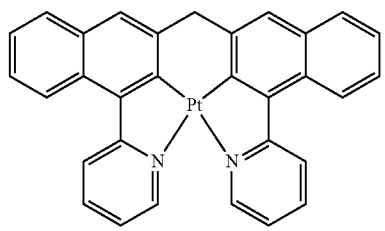
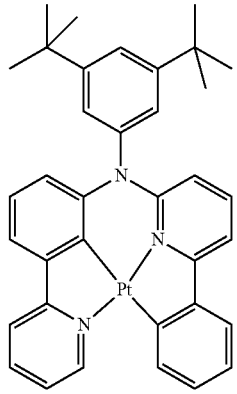
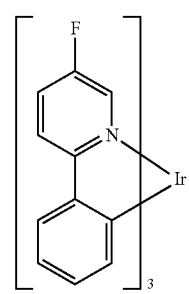

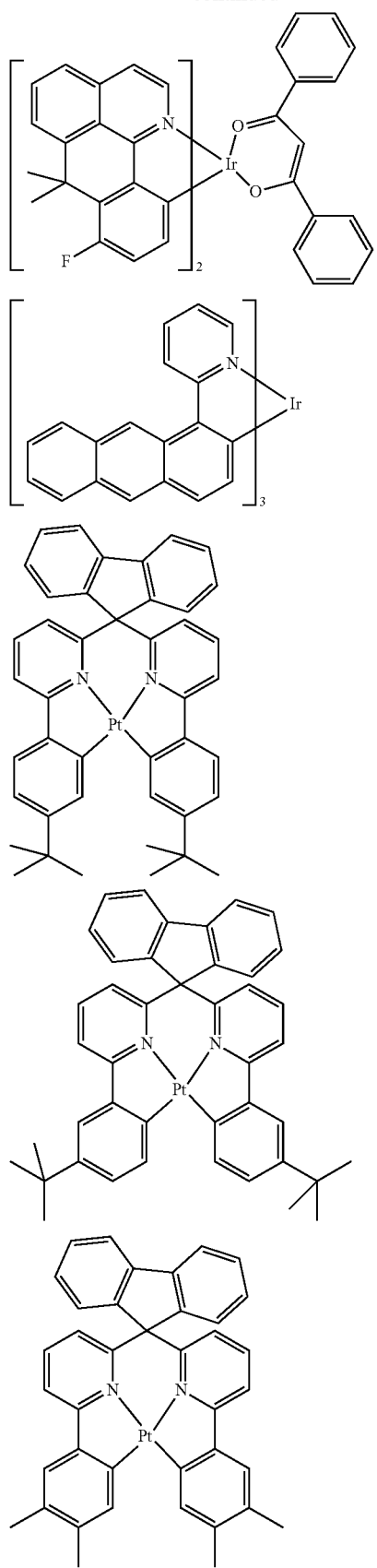

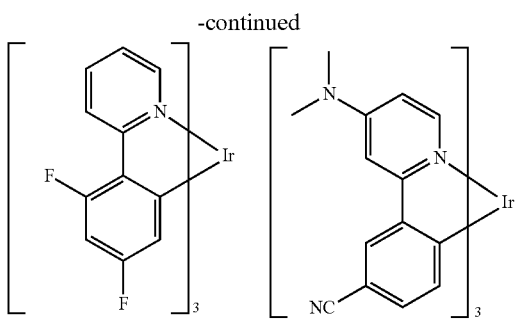
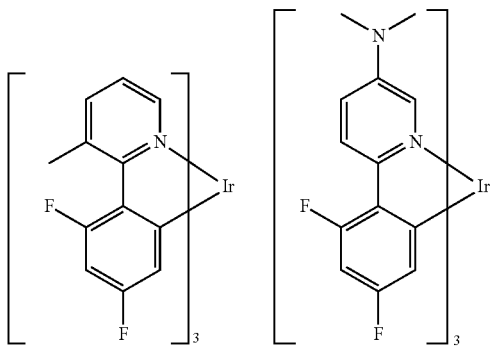
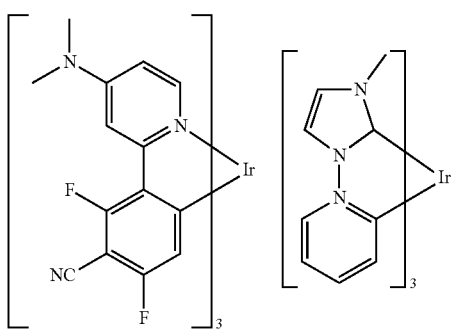
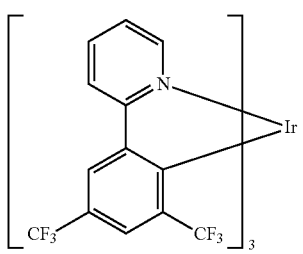
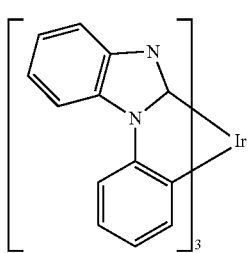
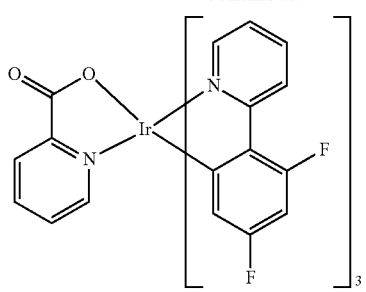
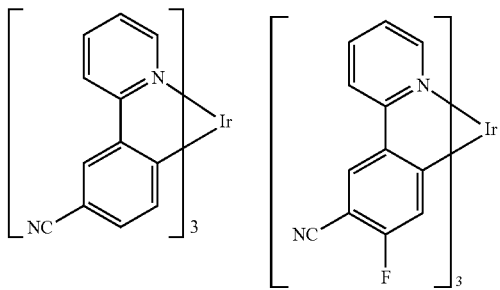
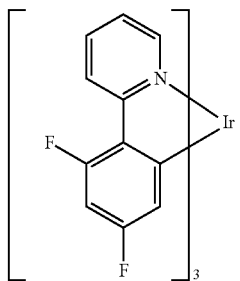
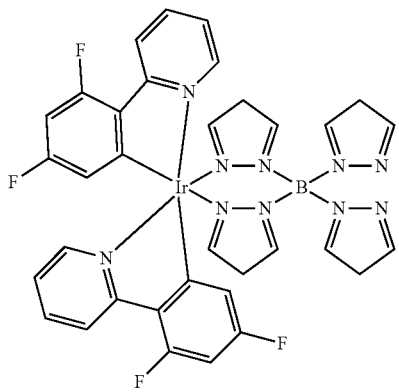
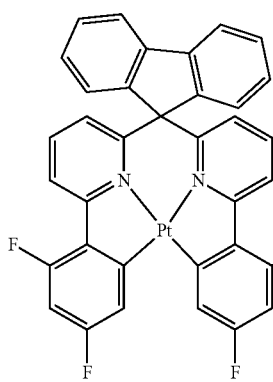

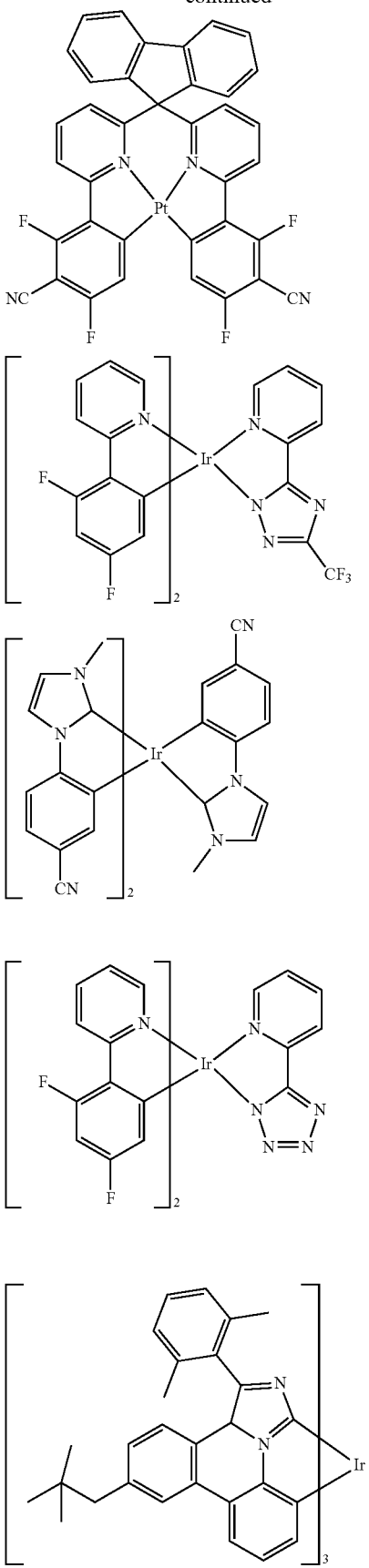

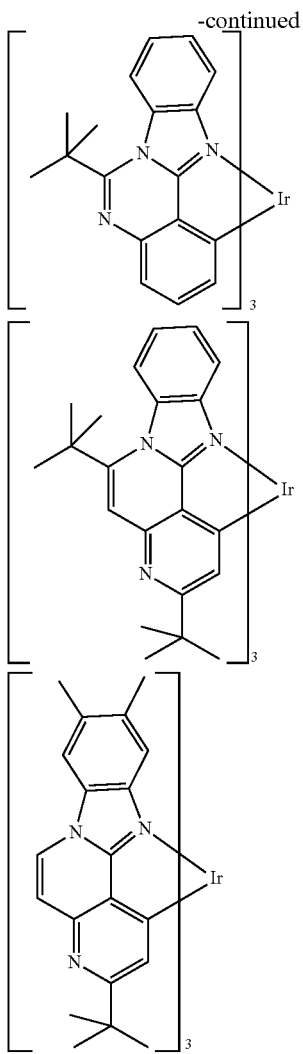

Preferred fluorescent dopants are selected from the class of the arylamines. An arylamine or aromatic amine in the sense of this invention is taken to mean a compound which contains three substituted or unsubstituted aromatic or heteroaromatic ring systems bonded directly to the nitrogen. At least one of these aromatic or heteroaromatic ring systems is preferably a condensed ring system, particularly preferably having at least 14 aromatic ring atoms.

Preferred examples thereof are aromatic anthracenamines, aromatic anthracenediamines, aromatic pyrenamines, aromatic pyrenediamines, aromatic chrysenamines or aromatic chrysenediamines. An aromatic anthracenamine is taken to mean a compound in which one diarylamino group is bonded directly to an anthracene group, preferably in the 9-position. An aromatic anthracenediamine is taken to mean a compound in which two diarylamino groups are bonded directly to an anthracene group, preferably in the 9,10-position. Aromatic pyrenamines, pyrenediamines, chrysenamines and chrysenediamines are defined analogously thereto, where the diarylamino groups are preferably bonded to the pyrene in the 1-position or in the 1,6-position. Further preferred dopants are indenofluorenamines and indeno-fluorenediamines, for example in accordance with WO 2006/108497 or WO 2006/122630, benzoindenofluorenamines and benzoindenofluorenediamines, for example in accordance with WO 2008/006449, and dibenzoindenofluorenamines and dibenzoindeno-fluorenediamines, for example in accordance with WO 2007/140847, and the indenofluorene derivatives containing condensed aryl groups disclosed in WO 2010/012328.

Suitable matrix materials, preferably for fluorescent dopants, besides the compounds of the formula (1), are materials from various classes of substance. Preferred matrix materials are selected from the classes of the oligoarylenes (for example 2,2',7,7'-tetraphenyl-spirobifluorene in accordance with EP 676461 or dinaphthylanthracene), in particular the oligoarylenes containing condensed aromatic groups, the oligoarylenevinylenes (for example DPVBi or spiro-DPVBi in accordance with EP 676461), the polypodal metal complexes (for example in accordance with WO 2004/081017), the hole-conducting compounds (for exam-pie in accordance with WO 2004/058911), the electron-conducting compounds, in particular ketones, phosphine oxides, sulfoxides, etc. (for example in accordance with WO 2005/084081 and WO 2005/084082), the atropisomers (for example in accordance with WO 2006/048268), the boronic acid derivatives (for example in accordance with WO 2006/117052) or the benzanthracenes (for example in accordance with WO 2008/145239). Particularly preferred matrix materials are selected from the classes of the oligoarylenes, comprising naphthalene, anthracene, benzanthracene and/or pyrene or atropisomers of these compounds, the oligoarylenevinylenes, the ketones, the phosphine oxides and the sulfoxides. Very particularly preferred matrix materials are selected from the classes of the oligoarylenes, comprising anthracene, benzanthracene, benzophenanthrene and/or pyrene or atropisomers of these compounds. An oligoarylene in the sense of this invention is intended to be taken to mean a compound in which at least three aryl or arylene groups are bonded to one another.

Preferred matrix materials for phosphorescent dopnats, besides the compounds of the formula (1), are aromatic amines, in particular triarylamines, for example in accordance with US 2005/0069729, carbazole derivatives (for example CBP, N,N-biscarbazolylbiphenyl) or compounds in accordance with WO 2005/039246, US 2005/0069729, JP 2004/288381, EP 1205527 or WO 2008/086851, bridged carbazole derivatives, for example in accordance with WO 2011/088877 and WO 2011/128017, indenocarbazole derivatives, for example in accordance with WO 2010/136109 and WO 2011/000455, azacarbazole derivatives, for example in accordance with EP 1617710, EP 1617711, EP 1731584, JP 2005/347160, indolocarbazole derivatives, for example in accordance with WO 2007/063754 or WO 2008/056746, ketones, for example in accordance with WO 2004/093207 or WO 2010/006680, phosphine oxides, sulfoxides and sulfones, for example in accordance with WO 2005/003253, oligophenylenes, bipolar matrix materials, for example in accordance with WO 2007/137725, silanes, for example in accordance with WO 2005/111172, aza-boroles or boronic esters, for example in accordance with WO 2006/117052, triazine derivatives, for example in accordance with WO 2010/015306, WO 2007/063754 or WO 2008/056746, zinc complexes, for example in accordance with EP 652273 or WO 2009/062578, aluminium complexes, for example BAlq, diazasilole and tetraazasilole derivatives, for example in accordance with WO 2010/054729, diazaphosphole derivatives, for example in accordance with WO 2010/054730, and aluminium complexes, for example BAIQ.

Apart from cathode, anode and the layer comprising the compound of the formula (1), the electronic device may also comprise further layers. These are selected, for example, from in each case one or more hole-injection layers, hole-transport layers, hole-blocking layers, emitting layers, electron-transport layers, electron-injection layers, electron-blocking layers, exciton-blocking layers, interlayers, charge-generation layers (IDMC 2003, Taiwan; Session 21 OLED (5), T. Matsumoto, T. Nakada, J. Endo, K. Mon, N. Kawamura, A. Yokoi, J. Kido, *Multiphoton Organic EL Device Having Charge Generation Layer*) and/or organic or inorganic p/n junctions. However, it should be pointed out that each of these layers does not necessarily have to be present.

The sequence of the layers of the organic electroluminescent device is preferably the following:

anode/hole-injection layer/hole-transport layer/emitting layer/electron-transport layer/electron-injection layer/cathode.

It should again be pointed out here that not all the said layers have to be present, and/or that further layers may additionally be present.

The organic electroluminescent device according to the invention may comprise a plurality of emitting layers. These emission layers in this case particularly preferably have in total a plurality of emission maxima between 380 nm and 750 nm, resulting overall in white emission, i.e. various emitting compounds which are able to fluoresce or phosphoresce and which emit blue or yellow or orange or red light are used in the emitting layers. Particular preference is given to three-layer systems, i.e. systems having three emitting layers, where the three layers exhibit blue, green and orange or red emission (for the basic structure see, for example, WO 2005/011013). It should be noted that, for the generation of white light, an emitter compound used individually which emits in a broad wavelength range may also be suitable instead of a plurality of emitter compounds emitting in colour.

Suitable charge-transport materials, as can be used in the hole-injection or hole-transport layer or electron-blocking layer or in the electron-transport layer of the organic electroluminescent device according to the invention, are, for example, the compounds disclosed in Y. Shirota et al., Chem. Rev. 2007, 107(4), 953-1010, or other materials as are employed in these layers in accordance with the prior art.

Materials which can be used for the electron-transport layer are all materials as are used in accordance with the prior art as electron-transport materials in the electron-transport layer.

Particularly suitable are aluminium complexes, for example $Alq_3$, zirconium complexes, for example $Zrq_4$, benzimidazole derivatives, triazine derivatives, pyrimidine derivatives, pyridine derivatives, pyrazine derivatives, quinoxaline derivatives, quinoline derivatives, oxadiazole derivatives, aromatic ketones, lactams, boranes, diazaphosphole derivatives and phosphine oxide derivatives. Furthermore suitable materials are derivatives of the above-mentioned compounds, as disclosed in JP 2000/053957, WO 2003/060956, WO 2004/028217, WO 2004/080975 and WO 2010/072300.

The hole-transport materials are particularly preferably materials which can be used in a hole-transport, hole-injection or electron-blocking layer, indenofluorenamine derivatives (for example in accordance with WO 06/122630 or WO 06/100896), the amine derivatives disclosed in EP 1661888, hexaazatriphenylene derivatives (for example in accordance with WO 01/049806), amine derivatives containing condensed aromatic rings (for example in accordance with U.S. Pat. No. 5,061,569), the amine derivatives disclosed in WO 95/09147, monobenzoindenofluorenamines (for example in accordance with WO 08/006449), dibenzoindenofluorenamines (for example in accordance with WO 07/140847), spirobifluorenamines (for example in accordance with WO 2012/034627 or the as yet unpublished EP 12000929.5), fluorenamines (for example in accordance with the as yet unpublished applications EP 12005369.9, EP 12005370.7 and EP 12005371.5), spirodibenzopyranamines (for example in accordance with the as yet unpublished application EP 11009127.9) and dihydroacridine derivatives (for example in accordance with the as yet unpublished EP 11007067.9).

The cathode of the electronic device preferably comprises metals having a low work function, metal alloys or multilayered structures comprising various metals, such as, for example, alkaline-earth metals, alkali metals, main-group metals or lanthanoids (for example Ca, Ba, Mg, Al, In, Mg, Yb, Sm, etc.). Also suitable are alloys comprising an alkali metal or alkaline-earth metal and silver, for example an alloy comprising magnesium and silver. In the case of multilayered structures, further metals which have a relatively high work function, such as, for example, Ag or Al, can also be used in addition to the said metals, in which case combinations of the metals, such as, for example, Ca/Ag, Mg/Ag or Ag/Ag, are generally used. It may also be preferred to introduce a thin interlayer of a material having a high dielectric constant between a metallic cathode and the organic semiconductor. Suitable for this purpose are, for example, alkali metal fluorides or alkaline-earth metal fluorides, but also the corresponding oxides or carbonates (for example LiF, $Li_2O$, $BaF_2$, MgO, NaF, CsF, $Cs_2CO_3$, etc.). Furthermore, lithium quinolinate (LiQ) can be used for this purpose. The layer thickness of this layer is preferably between 0.5 and 5 nm.

The anode preferably comprises materials having a high work function. The anode preferably has a work function of greater than 4.5 eV vs. vacuum. Suitable for this purpose are on the one hand metals having a high redox potential, such as, for example, Ag, Pt or Au. On the other hand, metal/metal oxide electrodes (for example $Al/Ni/NiO_x$, $Al/PtO_x$) may also be preferred. For some applications, at least one of the electrodes must be transparent or partially transparent in order to facilitate either irradiation of the organic material (organic solar cells) or the coupling-out of light (OLEDs, O-lasers). Preferred anode materials here are conductive mixed metal oxides. Particular preference is given to indium tin oxide (ITO) or indium zinc oxide (IZO). Preference is furthermore given to conductive, doped organic materials, in particular conductive doped polymers. Furthermore, the anode may also consist of a plurality of layers, for example of an inner layer of ITO and an outer layer of a metal oxide, preferably tungsten oxide, molybdenum oxide or vanadium oxide During production, the electronic device is appropriately (depending on the application) structured, provided with contacts and finally sealed, since the lifetime of the devices according to the invention is shortened in the presence of water and/or air.

In a preferred embodiment, the electronic device according to the invention is characterised in that one or more layers are applied by means of a sublimation process, in which the materials are applied by vapour deposition in vacuum sublimation units at an initial pressure of less than $10^{-5}$ mbar, preferably less than $10^{-6}$ mbar. However, it is also possible here for the initial pressure to be even lower, for example less than $10^{-7}$ mbar.

Preference is likewise given to an organic electroluminescent device, characterised in that one or more layers are applied by means of the OVPD (organic vapour phase deposition) process or with the aid of carrier-gas sublimation, in which the materials are applied at a pressure of between $10^{-5}$ mbar and 1 bar. A special case of this process is the OVJP (organic vapour jet printing) process, in which the materials are applied directly through a nozzle and are thus structured (for example M. S. Arnold et al., *Appl. Phys. Lett.* 2008, 92, 053301).

Preference is furthermore given to an organic electroluminescent device, characterised in that one or more layers are produced from solution, such as, for example, by spin coating, or by means of any desired printing process, such as, for example, screen printing, flexographic printing, nozzle printing or offset printing, but particularly preferably LITI (light induced thermal imaging, thermal transfer printing) or ink-jet printing. Soluble compounds of the formula (1) are necessary for this purpose. High solubility can be achieved through suitable substitution of the compounds.

For the production of an organic electroluminescent device according to the invention, it is furthermore preferred to apply one or more layers from solution and one or more layers by a sublimation process.

The invention thus furthermore relates to a process for the production of the electronic device according to the invention, characterised in that at least one organic layer is applied by gas-phase deposition or from solution.

In accordance with the invention, the electronic devices comprising one or more compounds of the formula (1) can be employed in displays, as light sources in lighting applications and as light sources in medical and/or cosmetic applications (for example light therapy).

The present invention also relates to a formulation comprising at least one compound of the formula (1) or at least one of the above-mention compositions and at least one solvent.

Suitable and preferred solvents are, for example, toluene, anisole, o-, m- or p-xylene, methyl benzoate, mesitylene, tetralin, veratrol, THF, methyl-THF, THP, chlorobenzene, dioxane, phenoxytoluene, in particular 3-phenoxytoluene, (−)-fenchone, 1,2,3,5-tetramethylbenzene, 1,2,4,5-tetramethylbenzene, 1-methylnaphthalene, 2-methylbenzothiazole, 2-phenoxyethanol, 2-pyrrolidinone, 3-methylanisole, 4-methylanisole, 3,4-dimethylanisole, 3,5-dimethylanisole, acetophenone, α-terpineol, benzothiazole, butyl benzoate, cumene, cyclohexanol, cyclohexanone, cyclohexylbenzene, decalin, dodecylbenzene, ethyl benzoate, indane, methyl benzoate, NMP, p-cymene, phenetol, 1,4-diisopropylbenzene, dibenzyl ether, diethylene glycol butyl methyl ether, triethylene glycol butyl methyl ether, diethylene glycol dibutyl ether, triethylene glycol dimethyl ether, diethylene glycol monobutyl ether, tripropylene glycol dimethyl ether, tetraethylene glycol dimethyl ether, 2-isopropylnaphthalene, pentylbenzene, hexylbenzene, heptylbenzene, octylbenzene, 1,1-bis(3,4-dimethylphenyl)ethane or mixtures of these solvents.

Devices comprising the compounds of the formula (1) can be employed in a very versatile manner. Thus, for example, electroluminescent devices comprising one or more compounds of the formula (1) can be employed in displays for televisions, mobile telephones, computers and cameras. However, the devices can also be used in lighting applications. Furthermore, electroluminescent devices, for example in OLEDs or OLECs, comprising at least one of the compounds of the formula (1) can be used for phototherapy in medicine or cosmetics. Thus, a large number of diseases (psoriasis, atopic dermatitis, inflammation, acne, skin cancer, etc.) can be treated or skin wrinkling, skin reddening and skin ageing can be prevented or reduced. Furthermore, the light-emitting devices can be utilised in order to keep drinks, meals or foods fresh or in order to sterilise equipment (for example medical equipment).

The present invention therefore relates to an electronic device, preferably an organic electroluminescent device, very preferably an OLED or OLEC and very particularly preferably an OLED, comprising at least one compound of the formula (1) for use in medicine for phototherapy.

The present invention furthermore preferably relates to an electronic device, preferably an organic electroluminescent device, very preferably an OLED or OLEC and very particularly preferably an OLED, comprising at least one compound of the formula (1) for use for the phototherapeutic treatment of skin diseases.

The present invention furthermore very preferably relates to an electronic device, preferably an organic electroluminescent device, very preferably an OLED or OLEC and very particularly preferably an OLED, comprising at least one compound of the formula (1) for use for the phototherapeutic treatment of psoriasis, atopic dermatitis, inflammatory diseases, vitiligo, wound healing and skin cancer.

The present invention furthermore relates to the use of the electronic device, preferably an organic electroluminescent device, very preferably an OLED or OLEC and very particularly preferably an OLED, comprising at least one compound of the formula (1) in cosmetics, preferably for the treatment of acne, ageing skin and of cellulite.

The compounds according to the invention or the organic electroluminescent devices according to the invention are distinguished over the prior art by the following surprising advantages:

1. The compounds according to the invention are very highly suitable for use in an emission layer and exhibit improved performance data compared with compounds from the prior art.
2. The compounds according to the invention have a relatively low sublimation temperature, high temperature stability and can therefore be sublimed without decomposition and without a residue. Furthermore, they have high oxidation stability and a high glass-transition temperature, which is advantageous both for the processability, for example from solution or from the gas phase, and also for the compound in electronic devices.
3. The use of the compounds according to the invention in electronic devices, in particular employed as electron-transport or electron-injection material, but also as matrix material, results in high efficiencies, low operating voltages and in long lifetimes.

It should be pointed out that variations of the embodiments described in the present invention fall within the scope of this invention. Each feature disclosed in the present invention can, unless explicitly excluded, be replaced by alternative features which serve the same, an equivalent or a similar purpose. Thus, each feature disclosed in the present invention should, unless stated otherwise, be regarded as an example of a generic series or as an equivalent or similar feature.

All features of the present invention can be combined with one another in any way, unless certain features and/or steps are mutually exclusive. This applies, in particular, to preferred features of the present invention. Equally, features of non-essential combinations can be used separately (and not in combination).

It should furthermore be pointed out that many of the features, and in particular those of the preferred embodiments of the present invention, are themselves inventive and should not merely be regarded as part of the embodiments of the present invention. For these features, independent protection may be sought in addition or as an alternative to each invention claimed at present.

The teaching on technical action disclosed with the present invention can be abstracted and combined with other examples.

The invention is illustrated in greater detail by the following examples, without wishing to restrict it thereby.

EXAMPLES

The following syntheses are carried out, unless indicated otherwise, under a protective-gas atmosphere in dried solvents. The solvents and reagents can be purchased, for example, from Sigma-ALDRICH or ABCR. The numbers in square brackets for chemical compounds which are known from the literature relate to the CAS numbers.

Example 1

Synthesis of 2-dlbenzofuran-4-yl-4,6-diphenyl-1,3,5-triazine

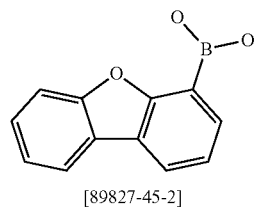

[89827-45-2]

+

[3842-55-5]

→

28.9 g (136 mmol) of dibenzofuran-4-boronic acid, 33 g (124.1 mmol) of 2-chloro-4,6-diphenyl-1,3,5-triazine and 78.9 ml (158 mmol) of Na$_2$CO$_3$ (2 M solution) are suspended in 120 ml of toluene, 120 ml of ethanol and 100 ml of water. 2.6 g (2.2 mmol) of Pd(PPh$_3$)$_4$ are added to this suspension, and the reaction mixture is heated under reflux for 16 h. After cooling, the organic phase is separated off, filtered through silica gel, washed three times with 200 ml of water and subsequently evaporated to dryness. The residue is recrystallised from toluene. The yield is 45 g (112 mmol), corresponding to 91% of theory.

The following compounds can be obtained analogously:

| Starting material 1 | Starting material 2 | Product | Yield |
|---|---|---|---|
| [89827-45-2] | [56181-49-8] | | 82% |
| [89827-45-2] | [864377-22-0] | | 79% |

| Starting material 1 | Starting material 2 | Product | Yield |
|---|---|---|---|
| 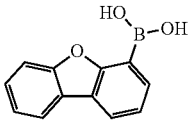 [89827-45-2] | 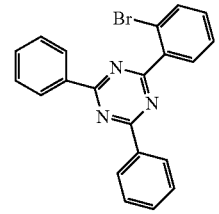 [SMILES: Brc1ccccc1-c1nc(-c2ccccc2)nc(-c2ccccc2)n1] 77989-15-2 | 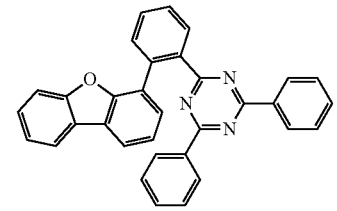 [SMILES: c1ccc(-c2nc(-c3ccccc3)nc(-c3ccccc3-c3cccc4c3oc3ccccc34)n2)cc1] | 70% |
| 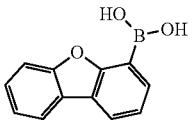 [89827-45-2] | 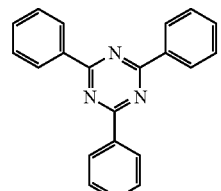 [23449-08-3] | 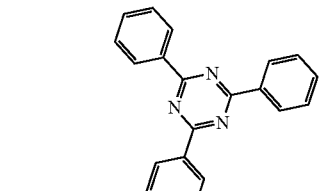 | 78% |
| 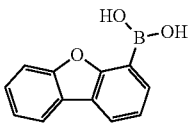 [SMILES: OB(O)c1cccc2c1oc1ccccc12] [89827-45-2] | 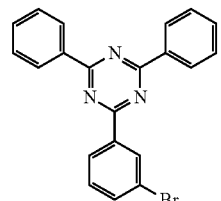 864377-31-1] | 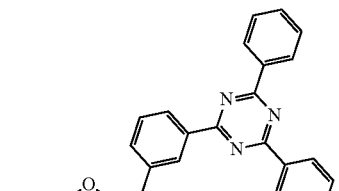 | 82% |
| 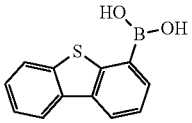 [SMILES: OB(O)c1cccc2c1sc1ccccc12] [108847-20-7] | 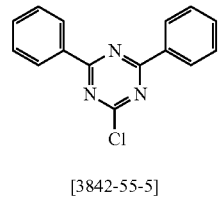 [3842-55-5] | 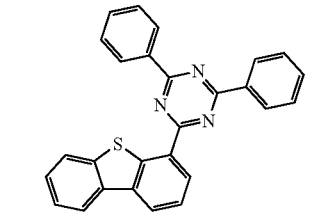 [SMILES: c1ccc(-c2nc(-c3ccccc3)nc(-c3cccc4c3sc3ccccc34)n2)cc1] | 80% |
| 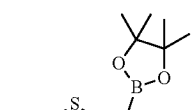 [912824-84-1] | 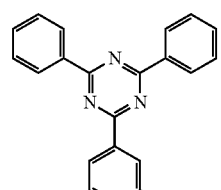 864377-31-1] | 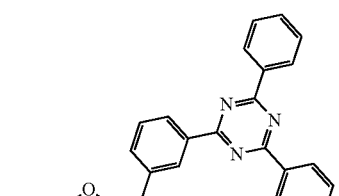 | 84% |

Example 2

Synthesis of 2-(8-bromodibenzofuran-4-yl)-4,6-diphenyl-1,3,5-triazine

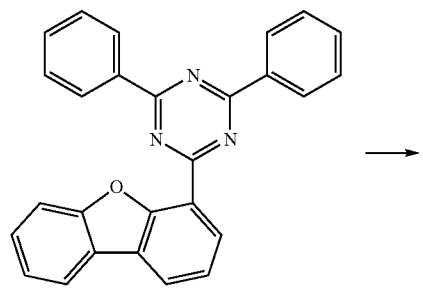

→

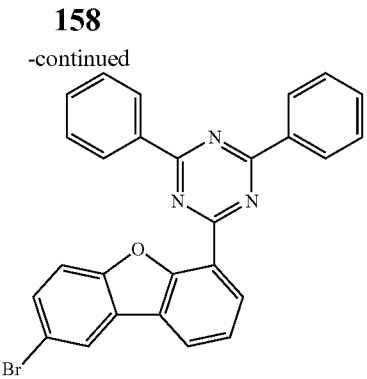

16 g (41 mmol) of 2-dibenzofuran-4-yl-4,6-diphenyl-1,3,5-triazine are initially introduced in 100 ml of dry dimethylformamide (DMF) with 8 mg of N-bromosuccinimide (NBS) (45 mmol, 1.1 mol %). The reaction mixture is heated at 120° C. for 24 h, and the solvent is then removed in vacuo. The residue is purified by column chromatography on silica gel with heptane/DCM (2/1) as eluent. The yield is 14.6 g (30 mmol), corresponding to 75% of theory.

The following compounds can be obtained analogously:

| Starting material 1 | Product | Yield |
|---|---|---|
| | | 73% |
| | | 58% |
| | | 61% |

-continued

| Starting material 1 | Product | Yield |
|---|---|---|
| | | 62% |
| | | 63% |
| | | 74% |
| | | 59% |

Example 3

Synthesis of 9-[6-(4,6-diphenyl-1,3,5-triazin-2-yl)dibenzofuran-2-yl]-3-phenyl-9H-carbazole

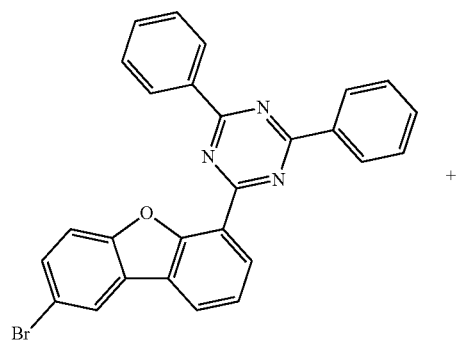

+

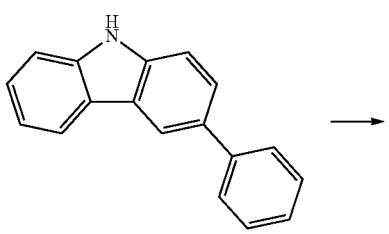

→

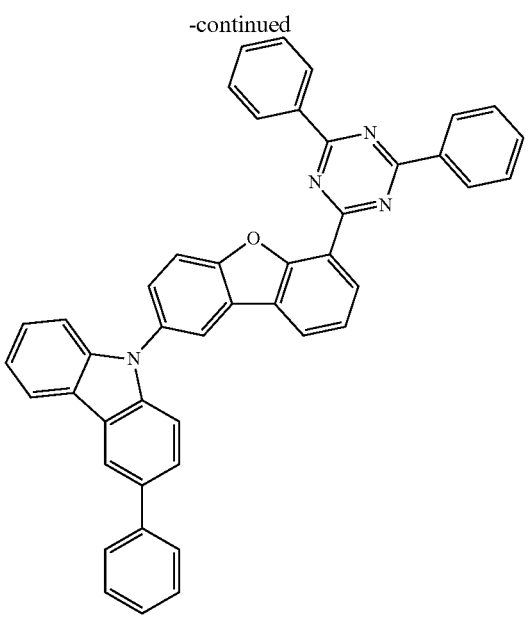

A degassed solution of 70 g (147 mmol) of 2-(8-bromodibenzofuran-4-yl)-4,6-diphenyl-1,3,5-triazine and 35.7 g (147 mmol) of 3-phenyl-9H-carbazole in 600 ml of toluene is saturated with $N_2$ for 1 h. Then, firstly 2.09 ml (8.6 mmol) of $P(tBu)_3$, then 1.38 g (6.1 mmol) of palladium(II) acetate are added gto the solution, and 17.7 g (185 mmol) of NaOtBu in the solid state are subsequently added to the solution. The reaction mixture is heated under reflux for 1 h. After cooling to room temperature, 500 ml of water are carefully added. The aqueous phase is washed with 3×50 ml of toluene, dried over $MgSO_4$, and the solvent is removed in vacuo. The crude product is then purified by chromatography over silica gel with heptane/ethyl acetate (20/1). The residue is recrystallised from toluene and finally sublimed in a high vacuum ($p=5\times10^{-6}$ mbar).

The yield is 77.7 g (121 mmol), corresponding to 83% of theory.

The following compounds can be obtained analogously:

| Starting material 1 | Starting material 2 | Product | Yield |
|---|---|---|---|
|  | [103012-26-6] |  | 92% |

-continued

| Starting material 1 | Starting material 2 | Product | Yield |
|---|---|---|---|
| | [1257220-47-5] | | 87% |
| | [1257220-47-5] | | 87% |
| | [1060735-14-9] | | 83% |
| | [1024598-06-8] | | 57% |

-continued
| Starting material 1 | Starting material 2 | Product | Yield |
|---|---|---|---|
| 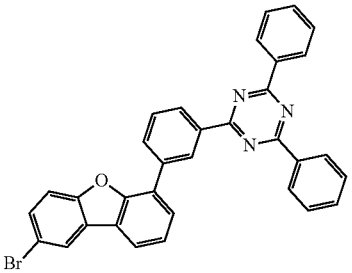 | 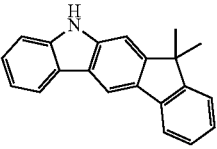 [SMILES: CC1(C)c2ccccc2-c2cc3c(cc21)[nH]c1ccccc13]
[1257220-47-5] | 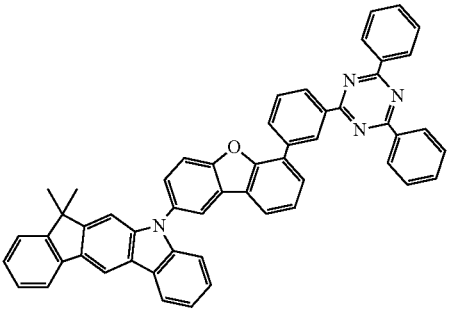 | 62% |
| 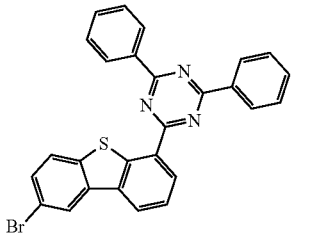 | 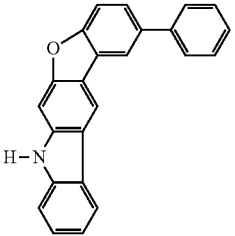 [SMILES: c1ccc(-c2ccc3oc4cc5[nH]c6ccccc6c5cc4c3c2)cc1]
[1439927-96-4] | 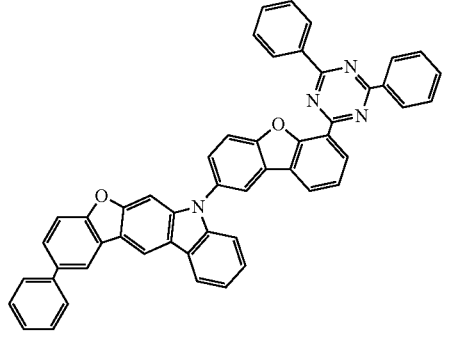 [SMILES: c1ccc(-c2ccc3oc4cc5c(cc4c3c2)c2ccccc2n5-c2ccc3oc4c(-c5nc(-c6ccccc6)nc(-c6ccccc6)n5)cccc4c3c2)cc1] | 72% |
| 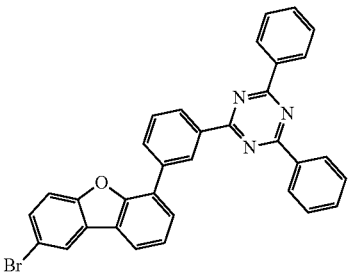 | 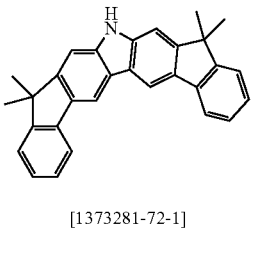
[1373281-72-1] | 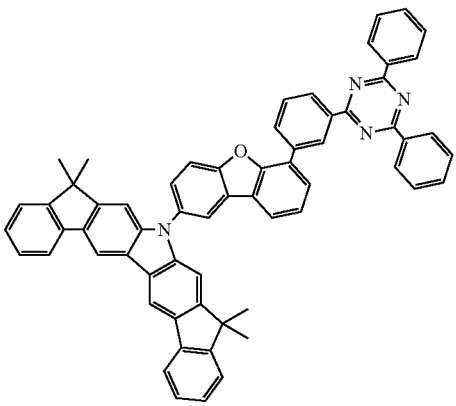 [SMILES: CC1(C)c2ccccc2-c2cc3c4cc5c(cc4n(-c4ccc6oc7c(-c8cccc(-c9nc(-c%10ccccc%10)nc(-c%10ccccc%10)n9)c8)cccc7c6c4)c3cc21)C(C)(C)c1ccccc1-5] | 70% |
| 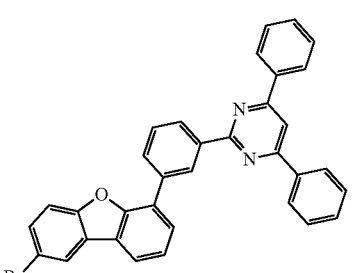 | 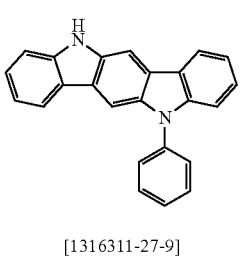
[1316311-27-9] | 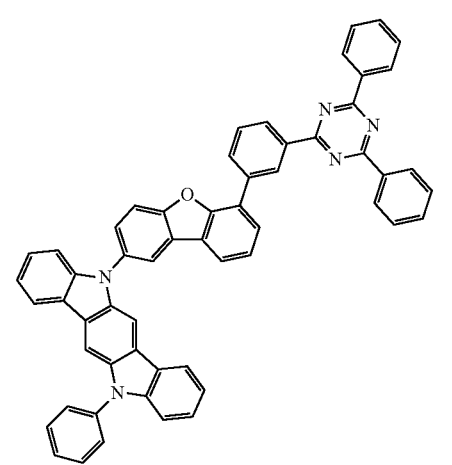 [SMILES: c1ccc(-c2nc(-c3ccccc3)nc(-c3cccc(-c4cccc5c4oc4ccc(-n6c7ccccc7c7cc8c(cc76)c6ccccc6n8-c6ccccc6)cc45)c3)n2)cc1] | 72% |

-continued
| Starting material 1 | Starting material 2 | Product | Yield |
|---|---|---|---|
| 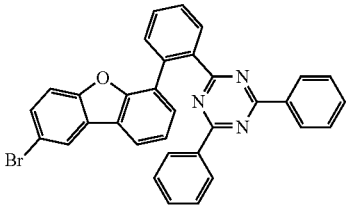 [SMILES: Brc1ccc2oc3c(-c4ccccc4-c4nc(-c5ccccc5)nc(-c5ccccc5)n4)cccc3c2c1] | 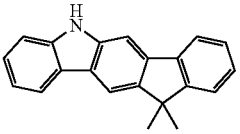 [SMILES: CC1(C)c2ccccc2-c2cc3[nH]c4ccccc4c3cc21]  [1260228-95-2] | 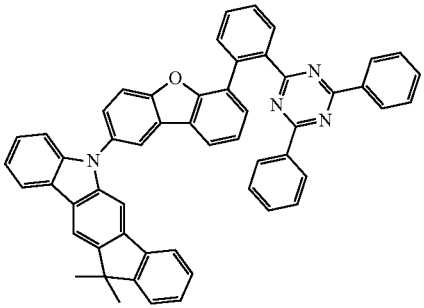 [SMILES: CC1(C)c2ccccc2-c2cc3c(cc21)c1ccccc1n3-c1ccc2oc3c(-c4ccccc4-c4nc(-c5ccccc5)nc(-c5ccccc5)n4)cccc3c2c1] | 65% |
| 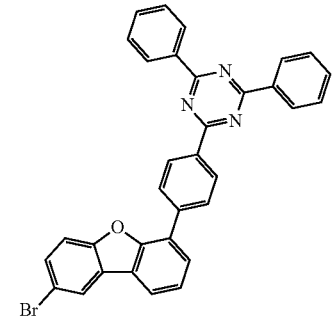 [SMILES: Brc1ccc2oc3c(-c4ccc(-c5nc(-c6ccccc6)nc(-c6ccccc6)n5)cc4)cccc3c2c1] | 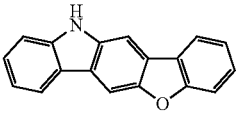 [SMILES: c1ccc2c(c1)[nH]c1cc3c(cc12)oc1ccccc13]  [1199350-22-5] | 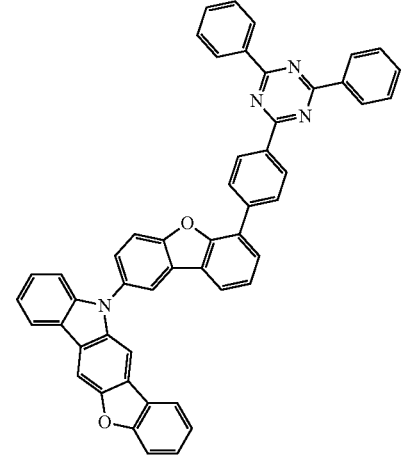 [SMILES: c1ccc(-c2nc(-c3ccccc3)nc(-c3ccc(-c4cccc5c4oc4ccc(-n6c7ccccc7c7cc8oc9ccccc9c8cc76)cc45)cc3)n2)cc1] | 68% |
| 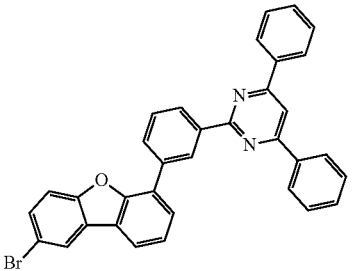 [SMILES: Brc1ccc2oc3c(-c4cccc(-c5nc(-c6ccccc6)cc(-c6ccccc6)n5)c4)cccc3c2c1] | 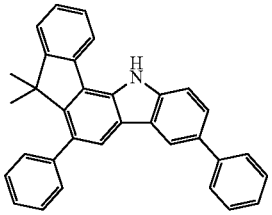 [SMILES: CC1(C)c2ccccc2-c2c1c(-c1ccccc1)cc1c2[nH]c2ccc(-c3ccccc3)cc21]  [1447708-58-8] | 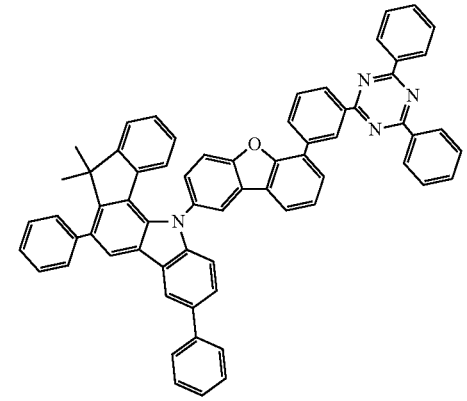 [SMILES: CC1(C)c2ccccc2-c2c1c(-c1ccccc1)cc1c3cc(-c4ccccc4)ccc3n(-c3ccc4oc5c(-c6cccc(-c7nc(-c8ccccc8)nc(-c8ccccc8)n7)c6)cccc5c4c3)c21] | 61% |
| 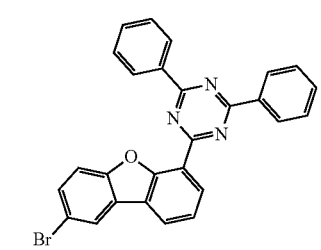 [SMILES: Brc1ccc2oc3c(-c4nc(-c5ccccc5)nc(-c5ccccc5)n4)cccc3c2c1] | 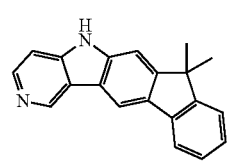 [SMILES: CC1(C)c2ccccc2-c2cc3c(cc21)[nH]c1ccncc13]  [1257248-14-8] | 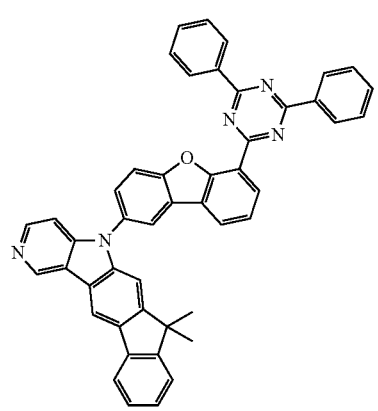 [SMILES: CC1(C)c2ccccc2-c2cc3c4cnccc4n(-c4ccc5oc6c(-c7nc(-c8ccccc8)nc(-c8ccccc8)n7)cccc6c5c4)c3cc21] | 72% |

Example 4
Synthesis of 2-dibenzofuran-4-yl-4-phenylquinazoline
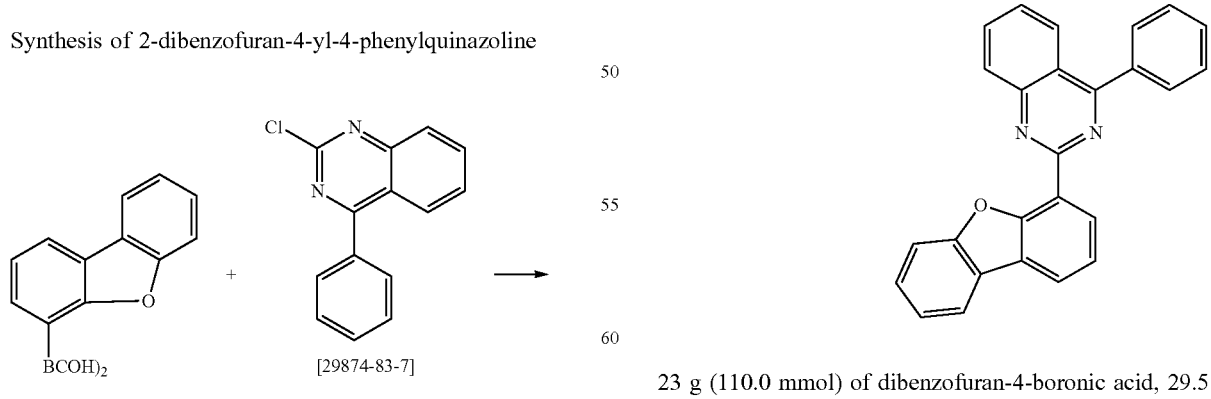
23 g (110.0 mmol) of dibenzofuran-4-boronic acid, 29.5 g (110.0 mmol) of 2-chloro-4-phenylquinazoline and 26 g (210.0 mmol) of sodium carbonate are suspended in 500 ml of ethylene glycol diamine ether and 500 ml of water. 913 mg (3.0 mmol) of tri-o-tolylphosphine and then 112 mg (0.5 mmol) of palladium(II) acetate are added to this suspension.

The reaction mixture is heated under reflux for 16 h. After cooling, the organic phase is separated off, filtered through silica gel, washed three times with 200 ml of water and subsequently evaporated to dryness. The residue is recrystallised from toluene and from dichloromethane/heptane. The yield is 31 g (85 mmol), corresponding to 79% of theory.

The following compounds can be obtained analogously:

| Starting material 1 | Starting material 2 | Product | Yield |
|---|---|---|---|
| 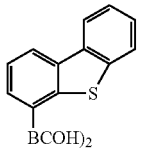 | 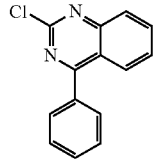 [SMILES: Clc1nc(-c2ccccc2)c2ccccc2n1] [29874-83-7] | 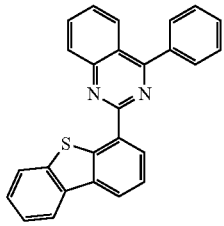 [SMILES: c1ccc(-c2nc(-c3cccc4c3sc3ccccc34)nc3ccccc23)cc1] | 73% |
| 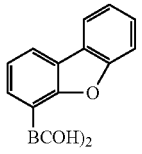 |  [6484-25-9] | 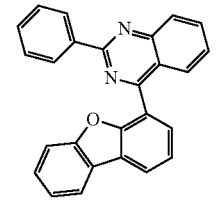 [SMILES: c1ccc(-c2nc(-c3cccc4c3oc3ccccc34)c3ccccc3n2)cc1] | 69% |
| 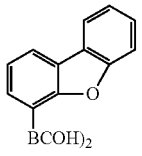 | 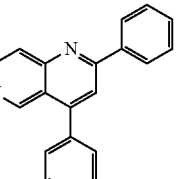 [1632307-99-3] | 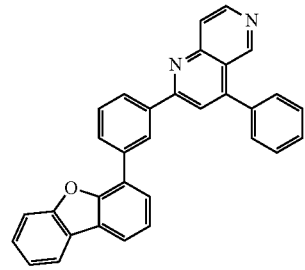 [SMILES: c1ccc(-c2cc(-c3cccc(-c4cccc5c4oc4ccccc45)c3)nc3ccncc23)cc1] | 67% |
| 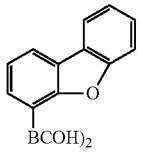 | 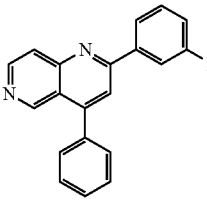 [1632307-97-1] | 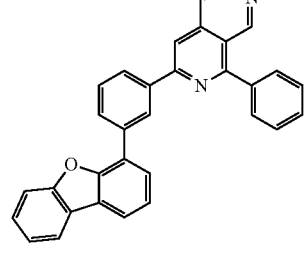 | 63% |
| 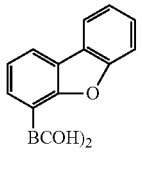 | 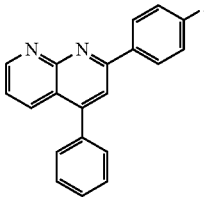 [1632294-77-9] | 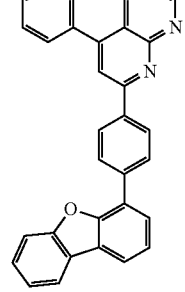 | 65% |

-continued

| Starting material 1 | Starting material 2 | Product | Yield |
|---|---|---|---|
| 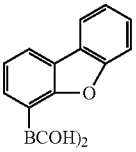 BCOH)2 | 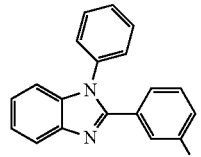 [760212-40-6] | 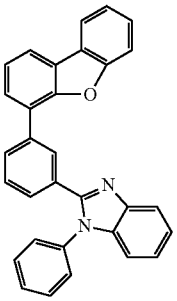 | 66% |
| 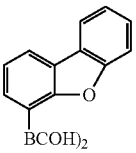 BCOH)2 | 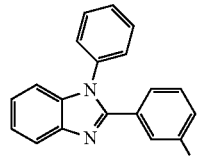 [760212-40-6] | 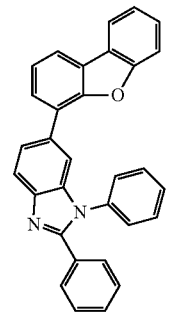 [SMILES: c1ccc(-c2nc3ccc(-c4cccc5c4oc4ccccc45)cc3n2-c2ccccc2)cc1] | 60% |

Example 5

Synthesis of 2-(8-bromodibenzofuran-4-yl)-4-phenylquinazoline

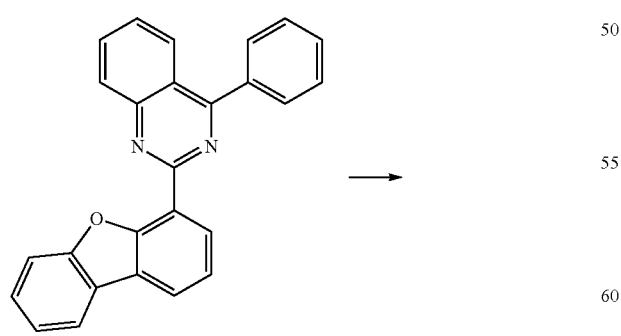 → 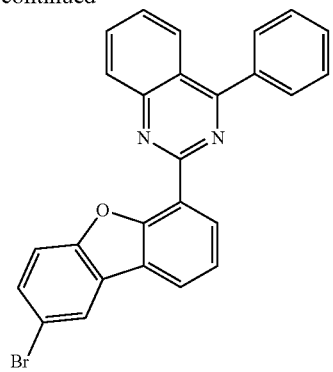

70.6 g (190.0 mmol) of 2-dibenzofuran-4-yl-4-phenylquinazoline are suspended in 2000 ml of acetic acid (100%) and 2000 ml of sulfuric acid (95-98%). 34 g (190 mmol) of NBS are added in portions to this suspension, and the mixture is stirred in the dark for 2 hours. Water/ice is then added, and the solid is separated off and rinsed with ethanol. The residue is recrystallised from toluene. The yield is 59 g (130 mmol), corresponding to 69% of theory.

In the case of thiophene derivatives, nitrobenzene is employed instead of sulfuric acid and elemental bromine is employed instead of NBS.

The following compounds can be obtained analogously:

| Starting material | Product | Yield |
| --- | --- | --- |
| | | 61% |
| | | 55% |
| | | 31% |
| | | 33% |
| | | 30% |

-continued

| Starting material | Product | Yield |
|---|---|---|
| | | 36% |
| | | 58% |

Example 6

Synthesis of 3-phenyl-9-[6-(4-phenylquinazolin-2-yl)dibenzofuran-2-yl]-9H-carbazole

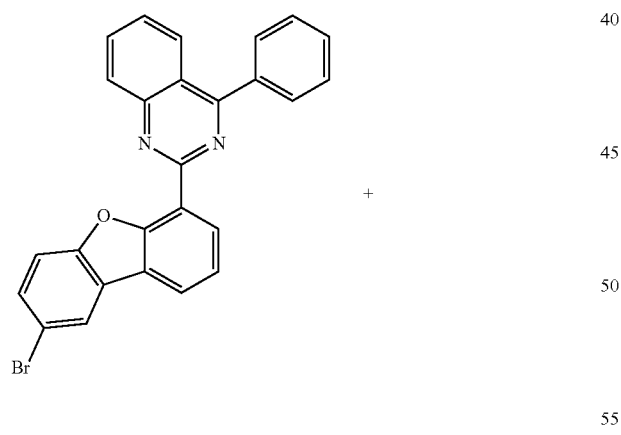

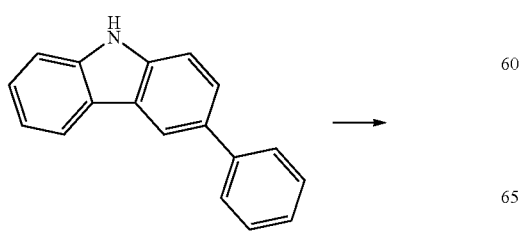

-continued

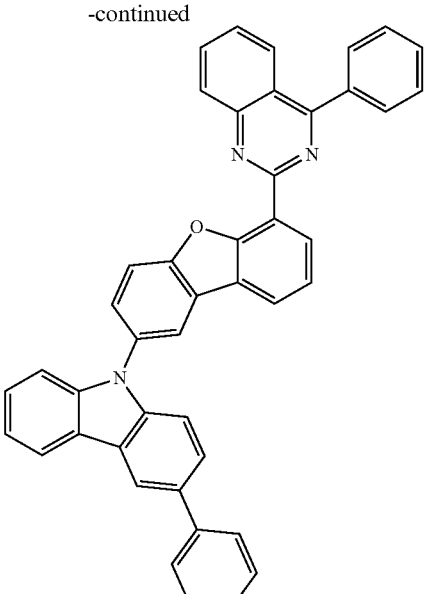

A degassed solution of 70 g (147 mmol) of 2-(8-bromodibenzofuran-4-yl)-4-phenylquinazoline and 35.7 g (147 mmol) of 3-phenyl-9H-carbazole in 600 ml of toluene is saturated with $N_2$ for 1 h. Then, firstly 2.09 ml (8.6 mmol) of $P(tBu)_3$, then 1.38 g (6.1 mmol) of palladium(II) acetate are added to the solution, and 17.7 g (185 mmol) of NaOtBu in the solid state are subsequently added. The reaction mixture is heated under reflux for 1 h. After cooling to room temperature, 500 ml of water are carefully added. The aqueous phase is washed 3 times with 50 ml of toluene, dried over MgSO$_4$, and the solvent is removed in vacuo. The crude product is then purified by chromatography over silica gel with heptane/ethyl acetate (20/1). The residue is recrystallised from toluene and finally sublimed in a high vacuum (p=5×10$^{-8}$ mbar).

The yield is 76 g (119 mmol), corresponding to 81% of theory.

The following compounds can be obtained analogously:

| Starting material 1 | Starting material 2 | Product | Yield |
|---|---|---|---|
| (structure with Br) | [1257220-47-5] | (product structure) | 73% |
| (structure with Br) | [1060735-14-9] | (product structure) | 71% |
| (structure with Br) | [1373281-72-1] | (product structure) | 69% |

-continued

| Starting material 1 | Starting material 2 | Product | Yield |
|---|---|---|---|
| | [250-25-4] | | 71% |
| | [250-25-4] | | 70% |
| | [250-25-4] | | 66% |
| | [1060735-14-9] | | 69% |

-continued

| Starting material 1 | Starting material 2 | Product | Yield |
|---|---|---|---|
| | [250-25-4] | | 78% |
| | [250-25-4] | | 74% |
| | [201-67-2] | | 75% |

| Starting material 1 | Starting material 2 | Product | Yield |
|---|---|---|---|
| (structure) | [250-25-4] | (structure) | 80% |
| (structure) | [1257220-47-5] | (structure) | 72% |

Example 16

Production and Characterisation of the OLEDs

The data of various OLEDs are presented in the following examples V1 to E12 (see Tables 1 and 2).

Pretreatment for Examples V1-E12

Glass plates which have been coated with structured ITO (indium tin oxide) in a thickness of 50 nm are coated with 20 nm of PEDOT:PSS (poly-(3,4-ethylenedioxythiophene) poly(styrenesulfonate), purchased as CLEVIOS™ P V P Al 4083 from Heraeus Precious Metals GmbH, Germany, applied by spin coating from aqueous solution) for improved processing. These coated glass plates form the substrates to which the OLEDs are applied.

The OLEDs have in principle the following layer structure: substrate/hole-transport layer (HTL)/optional interlayer (IL) I/electron-blocking layer (EBL)/emission layer (EML)/optional hole-blocking layer (HBL) I/electron-transport layer (ETL)/optional electron-injection layer (EIL) and finally a cathode. The cathode is formed by an aluminium layer with a thickness of 100 nm. The precise structure of the OLEDs is shown in Table 1. The materials required for the production of the OLEDs are shown in Table 3.

All materials are applied by thermal vapour deposition in a vacuum chamber. The emission layer here always consists of at least one matrix material (host material) and an emitting dopant (emitter), which are admixed with the matrix material or matrix materials in a certain proportion by volume by co-evaporation. An expression such as IC1:IC3:TEG1 (55%:35%:10%) here means that material IC1 is present in the layer in a proportion by volume of 55%, IC3 is present in the layer in a proportion of 35% and TEG1 is present in the layer in a proportion of 10%. Analogously, the electron-transport layer may also consist of a mixture of two materials.

The OLEDs are characterised by standard methods. For this purpose, the electroluminescence spectra, the current efficiency (measured in cd/A), the power efficiency (measured in lm/W) and the external quantum efficiency (EQE, measured in percent) as a function of the luminous density, calculated from current/voltage/luminous density characteristic lines (IUL characteristic lines) assuming Lambert emission characteristics, are determined. The electroluminescence spectra are determined at a luminous density of 1000 cd/m$^2$, and the CIE 1931 x and y colour coordinates are calculated therefrom. The term U1000 in Table 2 denotes the voltage required for a luminous density of 1000 cd/m$^2$. CE1000 and PE1000 denote the current and power efficiency respectively which are achieved at 1000 cd/m$^2$. Finally, EQE1000 denotes the external quantum efficiency at an operating luminous density of 1000 cd/m². The lifetime LT is defined as the time after which the luminous density drops to a certain proportion L1 from the initial luminous density on operation at constant current. An expression of L0; j0=4000 cd/m² and L1=70% means that the lifetime indicated corresponds to the time after which the initial luminous density drops from 4000 cd/m² to 2800 cd/m². Analogously, L0; j0=20 mA/cm², L1=80%, means that the luminous density drops to 80% of its initial value after time LT on operation at 20 mA/cm².

The data of the various OLEDs are summarised in Table 2. Examples V1-V5 are comparative examples in accordance with the prior art, Examples E1 to E12 show data of OLEDs according to the invention.

Some of the examples are explained in greater detail below in order to illustrate the advantages of the OLEDs according to the invention.

Use of Mixtures According to the Invention in the Emission Layer of Phosphorescent OLEDs The materials according to the invention give rise to significant improvements in the power efficiency compared with the prior art on use as matrix materials in phosphorescent OLEDs. The use of compounds EG1 and EG2 according to the invention in combination with the green-emitting dopant TEG1 enables an increase in the power efficiency by up to 20% compared with the prior art to be observed (comparison of Example E1 with V1 and comparison of E2 with V2, V3, V4 and V5). Furthermore, the compounds according to the invention result in a significant improvement in the lifetime of the components. Thus, the lifetime of component E2 comprising matrix EG2 according to the invention is improved from 125 h to 210 h compared with the prior art V4 comprising SdT4 (L0; j0=20 mA/cm², L1=80%).

TABLE 1

Structure of the OLEDs
HTL/IL (HATCN: 5 nm)/EBL/EML/HBL/ETL/EIL

| Ex. | HTL Thickness | EBL Thickness | EML Thickness | HBL Thickness | ETL Thickness | EIL Thickness |
|---|---|---|---|---|---|---|
| V1 | SpA1 70 nm | SpMA1 90 nm | SdT1:TEG1 (90%:10%) 30 nm | ST2 10 nm | ST2:LiQ (50%:50%) 30 nm | — |
| V2 | SpA1 70 nm | SpMA1 90 nm | SdT2:TEG1 (90%:10%) 30 nm | ST2 10 nm | ST2:LiQ (50%:50%) 30 nm | — |
| V3 | SpA1 70 nm | SpMA1 90 nm | SdT3:TEG1 (90%:10%) 30 nm | ST2 10 nm | ST2:LiQ (50%:50%) 30 nm | — |
| V4 | SpA1 70 nm | SpMA1 90 nm | SdT4:TEG1 (90%:10%) 30 nm | ST2 10 nm | ST2:LiQ (50%:50%) 30 nm | — |
| V5 | SpA1 70 nm | SpMA1 90 nm | SdT5:TEG1 (90%:10%) 30 nm | ST2 10 nm | ST2:LiQ (50%:50%) 30 nm | — |
| E1 | SpA1 70 nm | SpMA1 90 nm | EG1:TEG1 (90%:10%) 30 nm | ST2 10 nm | ST2:LiQ (50%:50%) 30 nm | — |
| E2 | SpA1 70 nm | SpMA1 90 nm | EG2:TEG1 (90%:10%) 30 nm | ST2 10 nm | ST2:LiQ (50%:50%) 30 nm | — |
| E3 | SpA1 70 nm | SpMA1 90 nm | EG3:TEG1 (90%:10%) 30 nm | ST2 10 nm | ST2:LiQ (50%:50%) 30 nm | — |
| E4 | SpA1 70 nm | SpMA1 90 nm | EG4:TEG1 (90%:10%) 30 nm | ST2 10 nm | ST2:LiQ (50%:50%) 30 nm | — |
| E5 | SpA1 70 nm | SpMA1 90 nm | EG5:TEG1 (90%:10%) 30 nm | ST2 10 nm | ST2:LiQ (50%:50%) 30 nm | — |
| E6 | SpA1 70 nm | SpMA1 90 nm | EG6:TEG1 (95%:5%) 30 nm | ST2 10 nm | ST2:LiQ (50%:50%) 30 nm | — |
| E7 | SpA1 70 nm | SpMA1 90 nm | IC1:TEG1 (90%:10%) 30 nm | EG7 10 nm | ST2:LiQ (50%:50%) 30 nm | — |
| E8 | SpA1 70 nm | SpMA1 90 nm | EG8:TEG1 (90%:10%) 30 nm | ST2 10 nm | ST2:LiQ (50%:50%) 30 nm | — |
| E9 | SpA1 70 nm | SpMA1 90 nm | EG9:IC3:TEG1 (60%:35%:5%) 30 nm | IC1 10 nm | ST2:LiQ (50%:50%) 30 nm | — |
| E10 | SpA1 90 nm | SpMA1 130 nm | E10:TER1 (92%:8%) 40 nm | — | ST2:LiQ (50%:50%) 40 nm | — |
| E11 | SpA1 90 nm | SpMA1 130 nm | E11:TER1 (92%:8%) 40 nm | — | ST2:LiQ (50%:50%) 40 nm | — |

TABLE 1-continued

Structure of the OLEDs
HTL/IL (HATCN: 5 nm)/EBL/EML/HBL/ETL/EIL

| Ex. | HTL Thickness | EBL Thickness | EML Thickness | HBL Thickness | ETL Thickness | EIL Thickness |
|---|---|---|---|---|---|---|
| E12 | SpA1 70 nm | SpMA1 90 nm | IC1:TEG1 (90%:10%) 30 nm | — | EG12:ST2 (50%:50%) 40 nm | LiQ 3 nm |

TABLE 2

Data of the OLEDs

| Ex. | U1000 (V) | CE1000 (cd/A) | PE1000 (lm/W) | EQE 1000 | CIE x/y at 1000 cd/m$^2$ |
|---|---|---|---|---|---|
| V1 | 3.5 | 48 | 43 | 12.8% | 0.32/0.64 |
| V2 | 3.6 | 51 | 44 | 13.7% | 0.33/0.63 |
| V3 | 4.1 | 50 | 38 | 13.3% | 0.33/0.63 |
| V4 | 3.4 | 52 | 49 | 14.1% | 0.33/0.62 |
| V5 | 4.4 | 48 | 34 | 12.9% | 0.33/0.62 |
| E1 | 3.3 | 53 | 51 | 14.2% | 0.33/0.63 |
| E2 | 3.2 | 54 | 53 | 13.9% | 0.32/0.65 |
| E3 | 3.4 | 53 | 49 | 14.5% | 0.32/0.63 |
| E4 | 3.6 | 58 | 51 | 15.4% | 0.32/0.64 |
| E5 | 3.4 | 46 | 43 | 13.1% | 0.33/0.62 |
| E6 | 3.5 | 51 | 46 | 13.8% | 0.32/0.63 |
| E7 | 3.3 | 61 | 58 | 16.7% | 0.33/0.63 |
| E8 | 3.6 | 51 | 45 | 14.0% | 0.33/0.63 |
| E9 | 3.4 | 56 | 49 | 15.7% | 0.33/0.62 |
| E10 | 4.1 | 13 | 10 | 12.3% | 0.67/0.33 |
| E11 | 4.3 | 12 | 9 | 12.4% | 0.66/0.34 |
| E12 | 3.4 | 62 | 57 | 16.9% | 0.33/0.63 |

TABLE 3

Structural formulae of the materials for the OLEDs

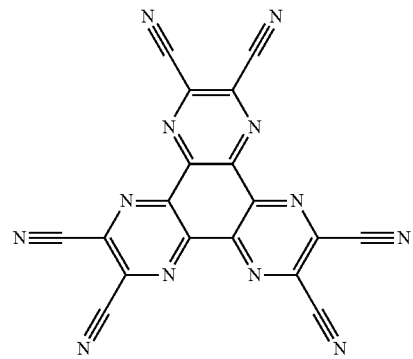 [SMILES: N#Cc1nc2c3nc(C#N)c(C#N)nc3c3nc(C#N)c(C#N)nc3c2nc1C#N]

HATCN

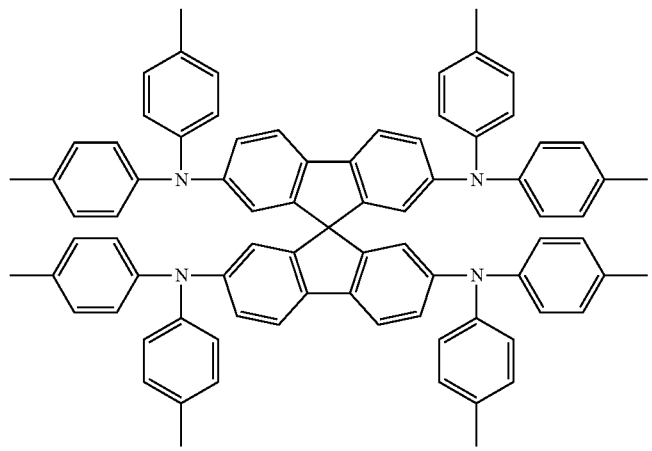

SpA1

TABLE 3-continued
Structural formulae of the materials for the OLEDs
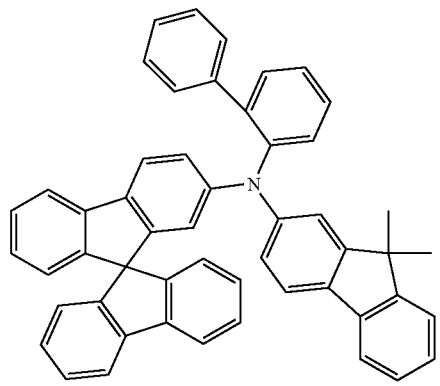 [SMILES: CC1(C)c2ccccc2-c2ccc(N(c3ccc4c(c3)C3(c5ccccc5-c5ccccc53)c3ccccc3-4)c3ccccc3-c3ccccc3)cc21]
SpMA1
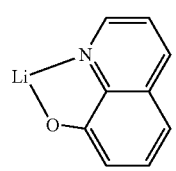
LiQ
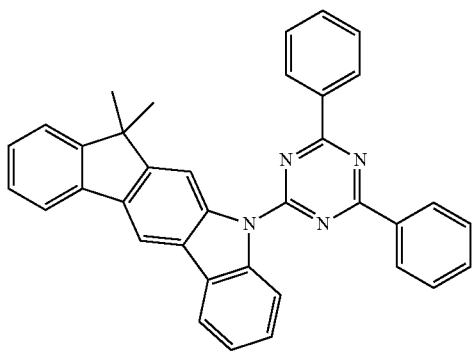 [SMILES: CC1(C)c2ccccc2-c2cc3c4ccccc4n(-c4nc(-c5ccccc5)nc(-c5ccccc5)n4)c3cc21]
IC1
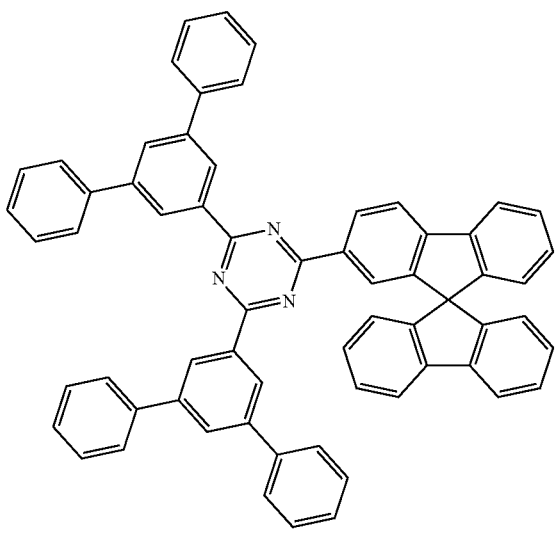 [SMILES: c1ccc(-c2cc(-c3ccccc3)cc(-c3nc(-c4cc(-c5ccccc5)cc(-c5ccccc5)c4)nc(-c4ccc5c(c4)C4(c6ccccc6-c6ccccc64)c4ccccc4-5)n3)c2)cc1]
ST2

TABLE 3-continued
Structural formulae of the materials for the OLEDs
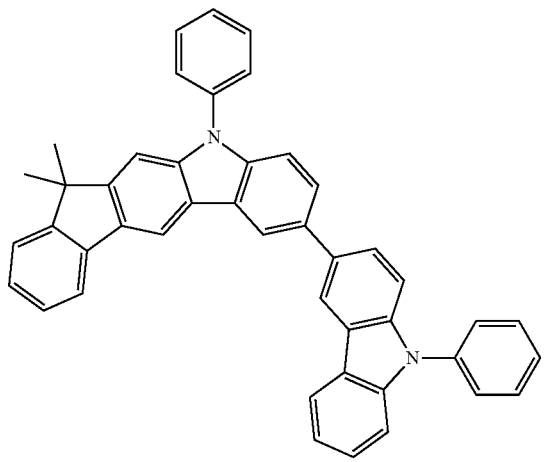 [SMILES: CC1(C)c2ccccc2-c2cc3c4cc(-c5ccc6c(c5)c5ccccc5n6-c5ccccc5)ccc4n(-c4ccccc4)c3cc21]
IC3
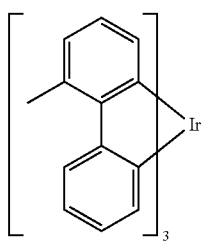
TEG1
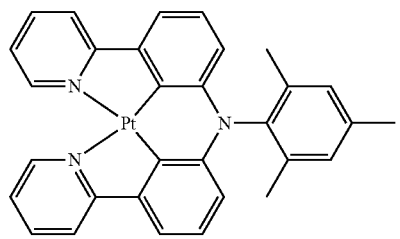
TER1
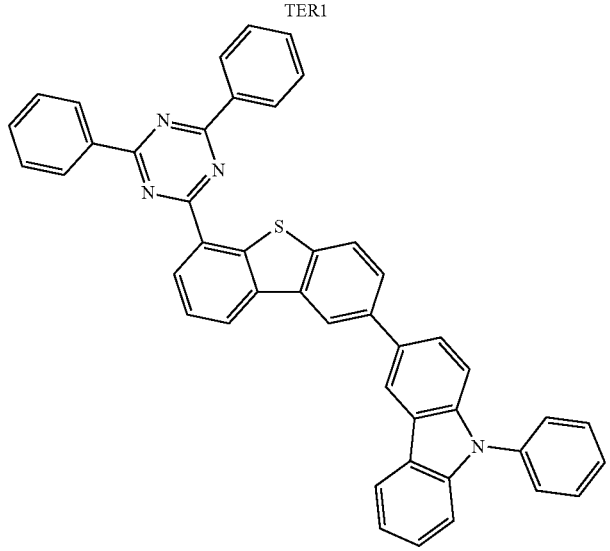
SdT1

TABLE 3-continued
Structural formulae of the materials for the OLEDs
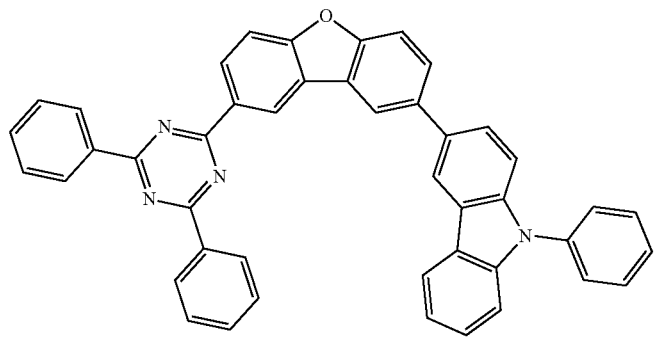 [SMILES: c1ccc(-c2nc(-c3ccccc3)nc(-c3ccc4oc5ccc(-c6ccc7c(c6)c6ccccc6n7-c6ccccc6)cc5c4c3)n2)cc1]
SdT2
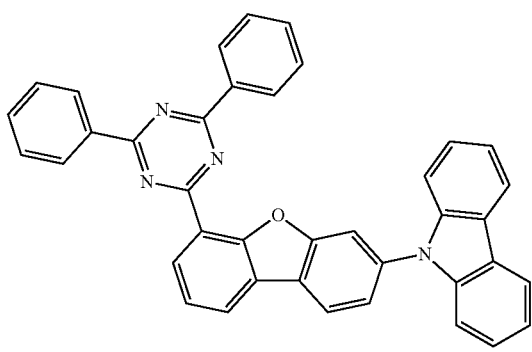 [SMILES: c1ccc(-c2nc(-c3ccccc3)nc(-c3cccc4c3oc3cc(-n5c6ccccc6c6ccccc65)ccc34)n2)cc1]
SdT3
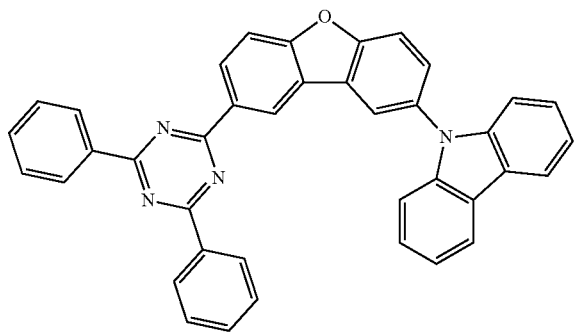 [SMILES: c1ccc(-c2nc(-c3ccccc3)nc(-c3ccc4oc5ccc(-n6c7ccccc7c7ccccc76)cc5c4c3)n2)cc1]
4SdT
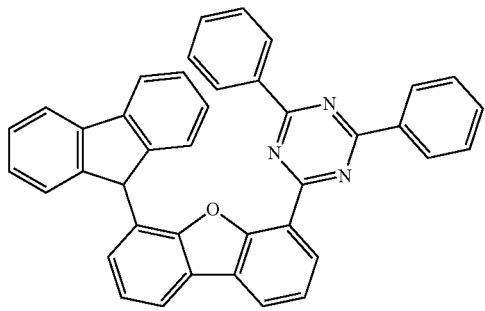 [SMILES: c1ccc(-c2nc(-c3ccccc3)nc(-c3cccc4c3oc3c(C5c6ccccc6-c6ccccc65)cccc34)n2)cc1]
SdT5

TABLE 3-continued
Structural formulae of the materials for the OLEDs
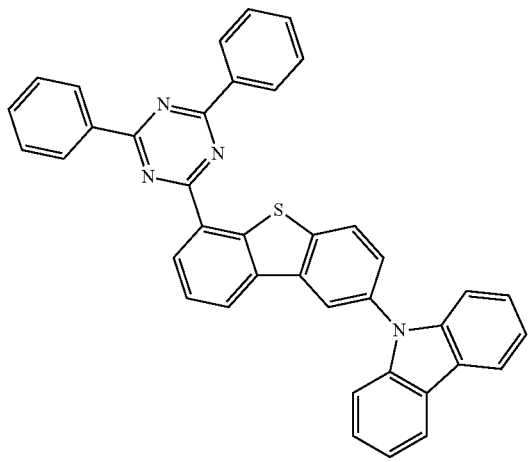 [SMILES: c1ccc(-c2nc(-c3ccccc3)nc(-c3cccc4c3sc3ccc(-n5c6ccccc6c6ccccc65)cc34)n2)cc1]
EG1
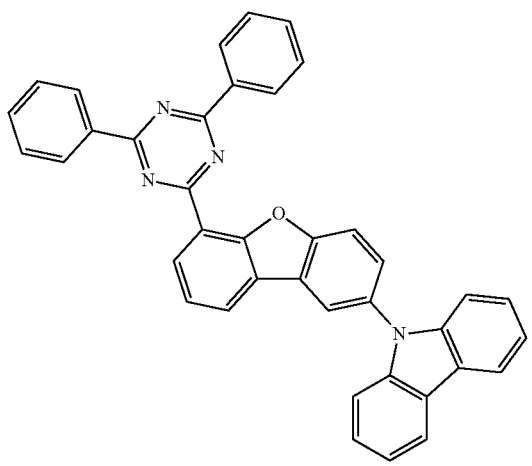
EG2
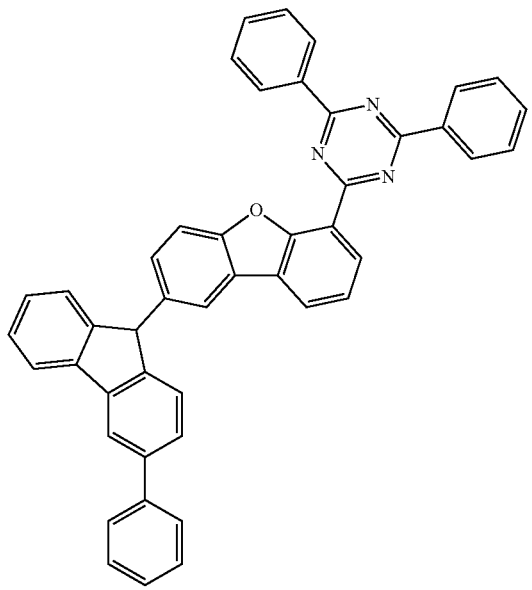 [SMILES: c1ccc(-c2ccc3c(c2)-c2ccccc2C3c2ccc3oc4c(-c5nc(-c6ccccc6)nc(-c6ccccc6)n5)cccc4c3c2)cc1]
EG3

TABLE 3-continued
Structural formulae of the materials for the OLEDs
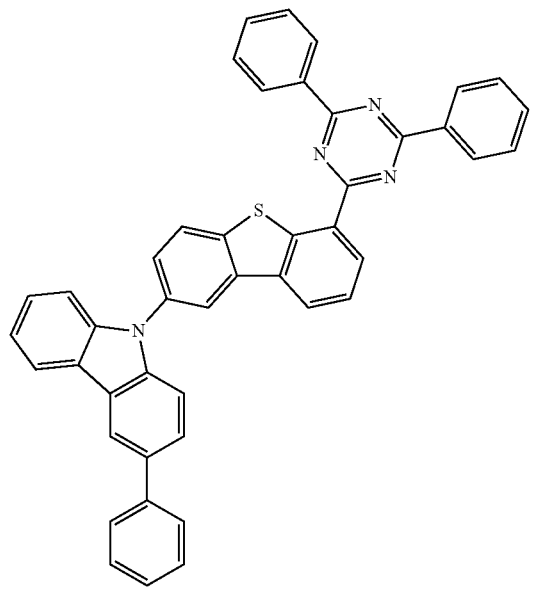 [SMILES: c1ccc(-c2ccc3c(c2)c2ccccc2n3-c2ccc3sc4c(-c5nc(-c6ccccc6)nc(-c6ccccc6)n5)cccc4c3c2)cc1]
EG4
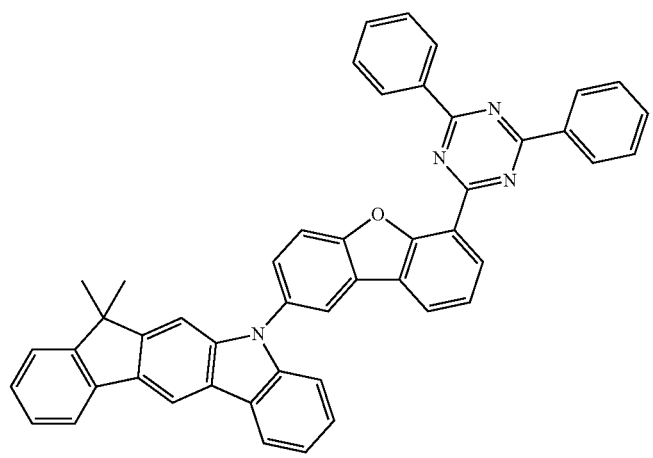 [SMILES: CC1(C)c2ccccc2-c2cc3c4ccccc4n(-c4ccc5oc6c(-c7nc(-c8ccccc8)nc(-c8ccccc8)n7)cccc6c5c4)c3cc21]
EG5

TABLE 3-continued
Structural formulae of the materials for the OLEDs
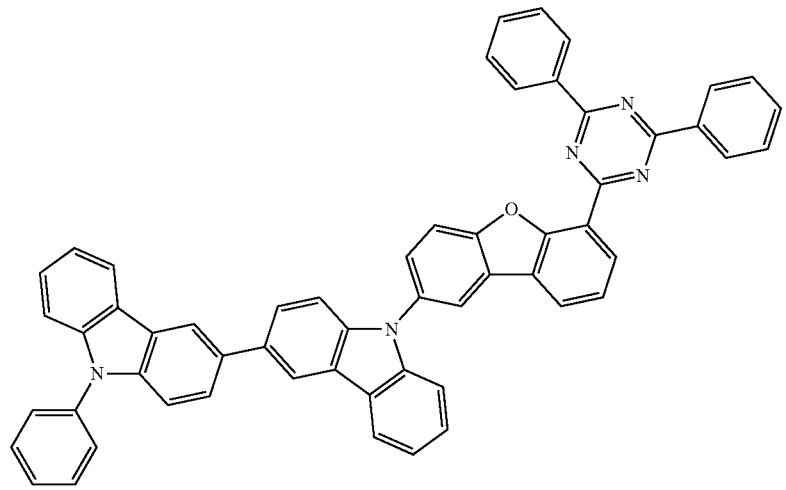 [SMILES: c1ccc(-c2nc(-c3ccccc3)nc(-c3cccc4c3oc3ccc(-n5c6ccccc6c6cc(-c7ccc8c(c7)c7ccccc7n8-c7ccccc7)ccc65)cc34)n2)cc1]
EG6
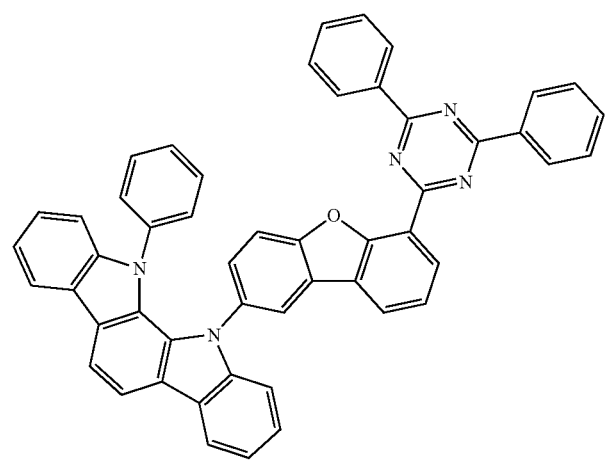 [SMILES: c1ccc(-c2nc(-c3ccccc3)nc(-c3cccc4c3oc3ccc(-n5c6ccccc6c6ccc7c8ccccc8n(-c8ccccc8)c7c65)cc34)n2)cc1]
EG7
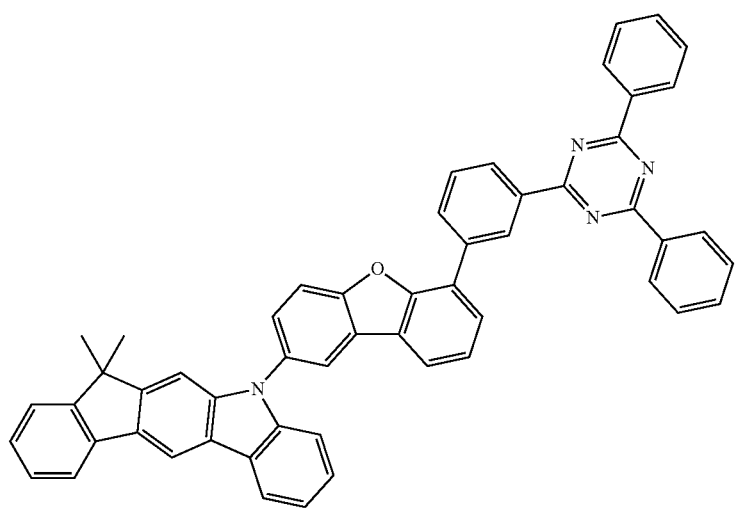 [SMILES: CC1(C)c2ccccc2-c2cc3c4ccccc4n(-c4ccc5oc6c(-c7cccc(-c8nc(-c9ccccc9)nc(-c9ccccc9)n8)c7)cccc6c5c4)c3cc21]
EG8

TABLE 3-continued
Structural formulae of the materials for the OLEDs
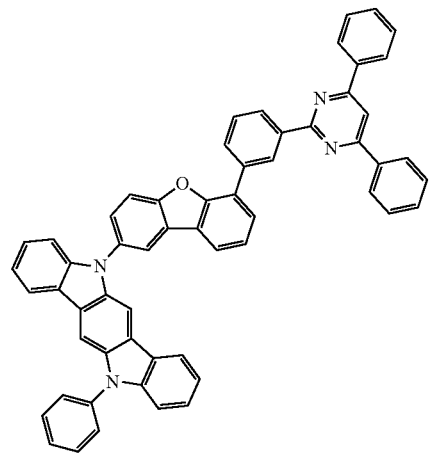 [SMILES: c1ccc(-c2cc(-c3ccccc3)nc(-c3cccc(-c4cccc5c4oc4ccc(-n6c7ccccc7c7cc8c(cc76)c6ccccc6n8-c6ccccc6)cc45)c3)n2)cc1]
EG9
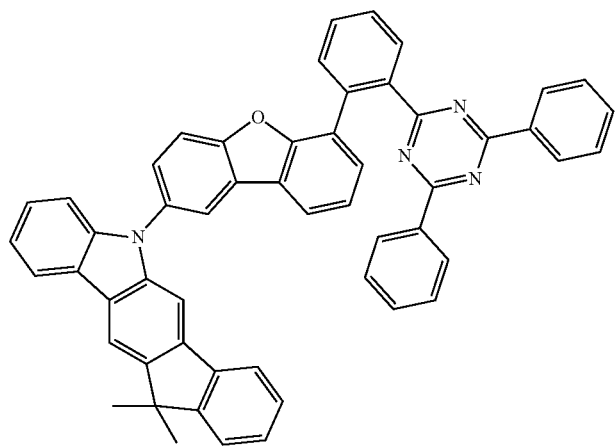 [SMILES: CC1(C)c2ccccc2-c2cc3c(cc21)c1ccccc1n3-c1ccc2oc3c(-c4ccccc4-c4nc(-c5ccccc5)nc(-c5ccccc5)n4)cccc3c2c1]
EG10
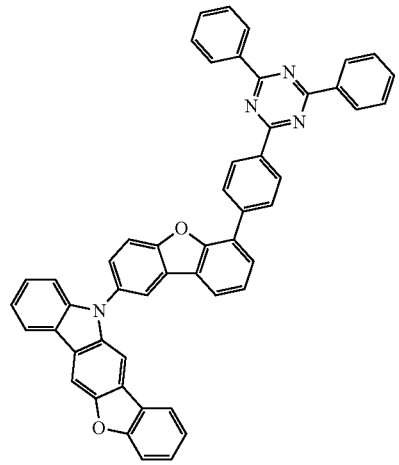 [SMILES: c1ccc(-c2nc(-c3ccccc3)nc(-c3ccc(-c4cccc5c4oc4ccc(-n6c7ccccc7c7cc8oc9ccccc9c8cc76)cc45)cc3)n2)cc1]
EG11

TABLE 3-continued

Structural formulae of the materials for the OLEDs

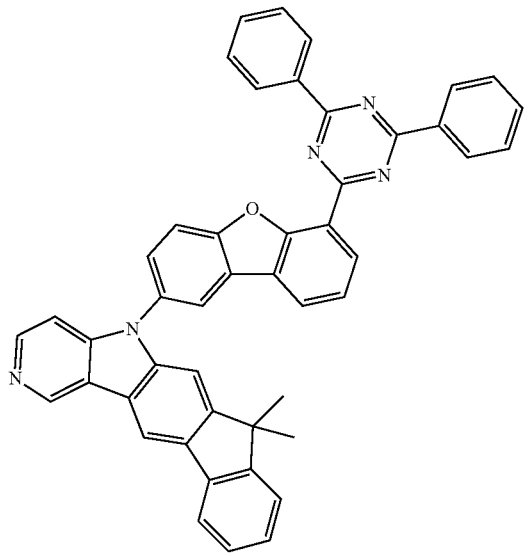 [SMILES: CC1(C)c2ccccc2-c2cc3c4cnccc4n(-c4ccc5oc6c(-c7nc(-c8ccccc8)nc(-c8ccccc8)n7)cccc6c5c4)c3cc21]

EG12

The invention claimed is:

1. An electronic device comprising at least one compound of the general formula (1)

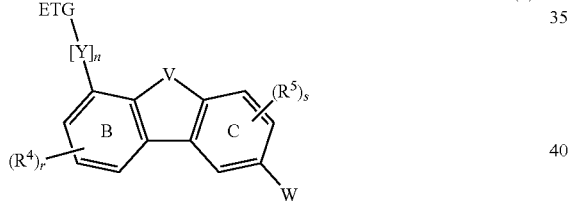

formula (1)

where the following applies to the symbols and indices used:

ETG is selected from the group of the triazines, pyrimidines, pyrazines, quinazolines, quinolines, isoquinolines and naphthyridines and the ETG is optionally substituted by one or more radicals $R^1$, which is optionally identical or different on each occurrence;

W is arylamines, bridged amines, where said bridged amines are carbazoles, bridged carbazoles, biscarbazoles, benzocarbazoles, indenocarbazoles and indolocarbazoles; and W is optionally substituted by one or more radicals $R^1$, which is optionally identical or different on each occurrence;

V is O;

Y is an aromatic or heteroaromatic ring system having 5 to 60 carbon atoms;

n is either 0 or 1;

r is an integer from 0, 1, 2 or 3;

s is an integer from 0, 1, 2 or 3;

$R^1$ is, identically or differently on each occurrence, H, D, F, Cl, Br, I, $N(R^2)_2$, CN, $NO_2$, $Si(R^2)_3$, $B(OR^2)_2$, $C(=O)R^2$, $P(=O)(R^2)_2$, $S(=O)R^2$, $S(=O)_2R^2$, $OSO_2R^2$, a straight-chain alkyl, alkoxy or thioalkoxy group having 1 to 40 C atoms or a straight-chain alkenyl or alkynyl group having 2 to 40 C atoms or a branched or cyclic alkyl, alkenyl, alkynyl, alkoxy, alkylalkoxy or thioalkoxy group having 3 to 40 C atoms, each of which is optionally substituted by one or more radicals $R^2$, where one or more non-adjacent $CH_2$ groups is optionally replaced by $R^2C=CR^2$, C≡C, $Si(R^2)_2$, $Ge(R^2)_2$, $Sn(R^2)_2$, C=O, C=S, C=Se, $C=NR^2$, $P(=O)(R^2)$, SO, $SO_2$, $NR^2$, O, S or $CONR^2$ and where one or more H atoms is optionally replaced by D, F, Cl, Br, I, CN or $NO_2$, or an aromatic or heteroaromatic ring system having 5 to 60 aromatic ring atoms, which may in each case be substituted by one or more radicals $R^2$, or an aryloxy, arylalkoxy or heteroaryloxy group having 5 to 60 aromatic ring atoms, which is optionally substituted by one or more radicals $R^2$, or a diarylamino group, diheteroarylamino group or arylheteroarylamino group having 10 to 40 aromatic ring atoms, which is optionally substituted by one or more radicals $R^2$, two or more adjacent radicals $R^1$ here may form a mono- or polycyclic, aliphatic or aromatic ring system with one another;

$R^2$ is, identically or differently on each occurrence, H, D, F, Cl, Br, I, $N(R^3)_2$, CN, $NO_2$, $Si(R^3)_3$, $B(OR^3)_2$, $C(=O)R^3$, $P(=O)(R^3)_2$, $S(=O)R^3$, $S(=O)_2R^3$, $OSO_2R^3$, a straight-chain alkyl, alkoxy or thioalkoxy group having 1 to 40 C atoms or a straight-chain alkenyl or alkynyl group having 2 to 40 C atoms or a branched or cyclic alkyl, alkenyl, alkynyl, alkoxy, alkylalkoxy or thioalkoxy group having 3 to 40 C atoms, each of which is optionally substituted by one or more radicals $R^3$, where one or more non-adjacent $CH_2$ groups is optionally replaced by $R^3C=CR^3$, C≡C, $Si(R^3)_2$, $Ge(R^3)_2$, $Sn(R^3)_2$, C=O, C=S, C=Se, $C=NR^3$, $P(=O)(R^3)$, SO, $SO_2$, $NR^3$, O, S or $CONR^3$ and where one or more H atoms is optionally replaced by D, F, Cl, Br, I, CN or $NO_2$, or an aromatic or heteroaromatic ring system having 5 to 60 aromatic ring atoms, which may in each case be substituted by one or more radicals $R^3$, or an aryloxy, arylalkoxy or heteroaryloxy group having 5 to 60 aromatic ring atoms, which is optionally substituted by one or more radicals R³, or a diarylamino group, diheteroarylamino group or arylheteroarylamino group having 10 to 40 aromatic ring atoms, which is optionally substituted by one or more radicals R³, or a combination of two or more of these groups; two or more adjacent radicals R² here may form a mono- or polycyclic, aliphatic or aromatic ring system with one another;

R³ is, identically or differently on each occurrence, H, D, F or an aliphatic, aromatic and/or heteroaromatic hydrocarbon radical having 1 to 20 C atoms, in which, in addition, one or more H atoms is optionally replaced by F; two or more substituents R³ here may also form a mono- or polycyclic, aliphatic or aromatic ring system with one another;

R⁴, R⁵ are, identically or differently on each occurrence, H, D, F, Cl, Br, I, $N(R^2)_2$, CN, $NO_2$, $Si(R^2)_3$, $B(OR^2)_2$, $C(=O)R^2$, $P(=O)(R^2)_2$, $S(=O)R^2$, $S(=O)_2R^2$, $OSO_2R^2$, a straight-chain alkyl, alkoxy or thioalkoxy group having 1 to 40 C atoms or a straight-chain alkenyl or alkynyl group having 2 to 40 C atoms or a branched or cyclic alkyl, alkenyl, alkynyl, alkoxy, alkylalkoxy or thioalkoxy group having 3 to 40 C atoms.

2. The electronic device according to claim 1, wherein the compound is in an emission layer (EML), electron-transport layer (ETL) or in a hole-blocking layer (HBL).

3. The electronic device according to claim 2, wherein the device is an organic integrated circuit (OIC), an organic field-effect transistor (OFET), an organic thin-film transistor (OTFT), an organic electroluminescent device, an organic solar cell (OSC), an organic optical detector, or an organic photoreceptor.

4. The electronic device according to claim 2, wherein the device is an organic electroluminescent device which is also selected from the group consisting of an organic light-emitting transistor (OLET), an organic field-quench device (OFQD), an organic light-emitting electrochemical cell, an organic laser diode (O-laser) and an organic light-emitting diode (OLED).

5. A process for the production of the electronic device according to claim 2, which comprises applying at least one organic layer comprising the compound of formula (I) by gas-phase deposition or from solution.

6. A process for phototherapy of the skin which comprises utilizing the electronic device according to claim 2 for treating the skin.

7. The electronic device according to claim 1, wherein
Y is a phenylene bridge;
r is 0; and
s is 0.

8. The electronic device according to claim 1, wherein the compound has the general formula (2)

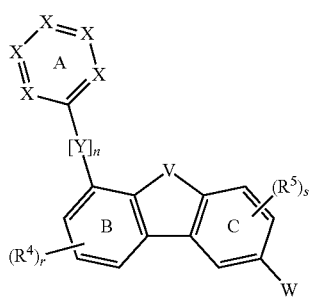

formula (2)

wherein:
X is N or CR¹, where at least one of the five groups X in ring A represents an N atom.

9. The electronic device according to claim 1, wherein W is defined by the formula (W-1)

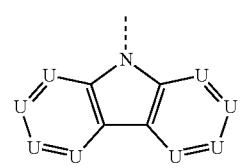

formula (W-1)

wherein:
U is N or CR¹, where the dotted line denotes the bond from the group W to the ring C.

10. An electronic device comprising at least one compound of the general formula (4):

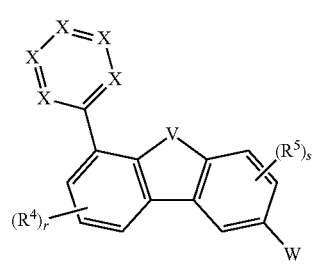

formula (4)

X is N or CR¹, with the proviso at least one of the X represents an N atom,
W is arylamines, bridged amines, where said bridged amines are carbazoles, bridged carbazoles, biscarbazoles, benzocarbazoles, indenocarbazoles and indolocarbazoles; and W is optionally substituted by one or more radicals R¹, which is optionally identical or different on each occurrence;
V is O;
r is an integer from 0, 1, 2 or 3;
s is an integer from 0, 1, 2 or 3;
R¹ is, identically or differently on each occurrence, H, D, F, Cl, Br, I, $N(R^2)_2$, CN, $NO_2$, $Si(R^2)_3$, $B(OR^2)_2$, $C(=O)R^2$, $P(=O)(R^2)_2$, $S(=O)R^2$, $S(=O)_2R^2$, $OSO_2R^2$, a straight-chain alkyl, alkoxy or thioalkoxy group having 1 to 40 C atoms or a straight-chain alkenyl or alkynyl group having 2 to 40 C atoms or a branched or cyclic alkyl, alkenyl, alkynyl, alkoxy, alkylalkoxy or thioalkoxy group having 3 to 40 C atoms, each of which is optionally substituted by one or more radicals R², where one or more non-adjacent $CH_2$ groups is optionally replaced by $R^2C=CR^2$, C≡C, $Si(R^2)_2$, $Ge(R^2)_2$, $Sn(R^2)_2$, C=O, C=S, C=Se, $C=NR^2$, $P(=O)(R^2)$, SO, $SO_2$, $NR^2$, O, S or $CONR^2$ and where one or more H atoms is optionally replaced by D, F, Cl, Br, I, CN or $NO_2$, or an aromatic or heteroaromatic ring system having 5 to 60 aromatic ring atoms, which may in each case be substituted by one or more radicals R², or an aryloxy, arylalkoxy or heteroaryloxy group having 5 to 60 aromatic ring atoms, which is optionally substituted by one or more radicals R², or a diarylamino group, diheteroarylamino group or arylheteroarylamino group having 10 to 40 aromatic ring atoms, which is optionally substituted by one or more radicals $R^2$, two or more adjacent radicals $R^1$ here may form a mono- or polycyclic, aliphatic or aromatic ring system with one another;

$R^2$ is, identically or differently on each occurrence, H, D, F, Cl, Br, I, $N(R^3)_2$, CN, $NO_2$, $Si(R^3)_3$, $B(OR^3)_2$, $C(=O)R^3$, $P(=O)(R^3)_2$, $S(=O)R^3$, $S(=O)_2R^3$, $OSO_2R^3$, a straight-chain alkyl, alkoxy or thioalkoxy group having 1 to 40 C atoms or a straight-chain alkenyl or alkynyl group having 2 to 40 C atoms or a branched or cyclic alkyl, alkenyl, alkynyl, alkoxy, alkylalkoxy or thioalkoxy group having 3 to 40 C atoms, each of which is optionally substituted by one or more radicals $R^3$, where one or more non-adjacent $CH_2$ groups is optionally replaced by $R^3C=CR^3$, $C\equiv C$, $Si(R^3)_2$, $Ge(R^3)_2$, $Sn(R^3)_2$, C=O, C=S, C=Se, $C=NR^3$, $P(=O)(R^3)$, SO, $SO_2$, $NR^3$, O, S or $CONR^3$ and where one or more H atoms is optionally replaced by D, F, Cl, Br, I, CN or $NO_2$, or an aromatic or heteroaromatic ring system having 5 to 60 aromatic ring atoms, which may in each case be substituted by one or more radicals $R^3$, or an aryloxy, arylalkoxy or heteroaryloxy group having 5 to 60 aromatic ring atoms, which is optionally substituted by one or more radicals $R^3$, or a diarylamino group, diheteroarylamino group or arylheteroarylamino group having 10 to 40 aromatic ring atoms, which is optionally substituted by one or more radicals $R^3$, or a combination of two or more of these groups; two or more adjacent radicals $R^2$ here may form a mono- or polycyclic, aliphatic or aromatic ring system with one another;

$R^3$ is, identically or differently on each occurrence, H, D, F or an aliphatic, aromatic and/or heteroaromatic hydrocarbon radical having 1 to 20 C atoms, in which, in addition, one or more H atoms is optionally replaced by F; two or more substituents $R^3$ here may also form a mono- or polycyclic, aliphatic or aromatic ring system with one another;

$R^4$, $R^5$ are, identically or differently on each occurrence, H, D, F, Cl, Br, I, $N(R^2)_2$, CN, $NO_2$, $Si(R^2)_3$, $B(OR^2)_2$, $C(=O)R^2$, $P(=O)(R^2)_2$, $S(=O)R^2$, $S(=O)_2R^2$, $OSO_2R^2$, a straight-chain alkyl, alkoxy or thioalkoxy group having 1 to 40 C atoms or a straight-chain alkenyl or alkynyl group having 2 to 40 C atoms or a branched or cyclic alkyl, alkenyl, alkynyl, alkoxy, alkylalkoxy or thioalkoxy group having 3 to 40 C atoms.

11. The electronic device according to claim 1, wherein the compound has the general formula (6):

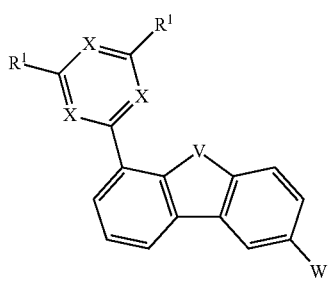

formula (6)

X is N or $CR^1$, with the proviso at least one of the X represents an N atom.

12. The electronic device according to claim 1, wherein the compound has the general formula (7):

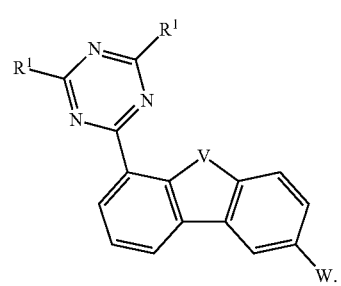

formula (7)

13. The electronic device according to claim 1, wherein the group W is a carbazole, indenocarbazole or indolocarbazole.

14. The electronic device according to claim 1, wherein the group W is a group of the formula (W-2)

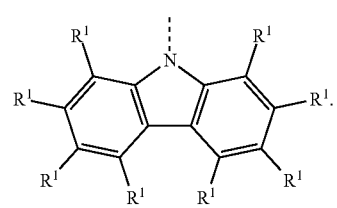

formula (W-2)

15. An electronic device comprising at least one compound of the general formula (1)

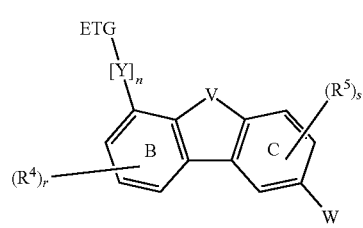

formula (1)

where the following applies to the symbols and indices used:

ETG is selected from the group of the triazines, pyrimidines, pyrazines, pyridines, quinazolines, quinolines, isoquinolines and naphthyridines and the ETG is optionally substituted by one or more radicals $R^1$, which is optionally identical or different on each occurrence;

V is O;

Y is an aromatic or heteroaromatic ring system having 5 to 60 carbon atoms;

n is either 0 or 1;

r is an integer from 0, 1, 2 or 3;

s is an integer from 0, 1, 2 or 3;

W is a group of the formula (W-5)

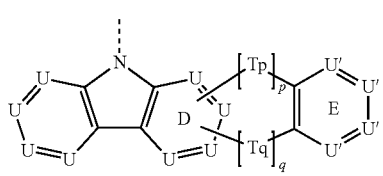

formula (W-5)

where the above definitions apply to the indices and symbols used and where furthermore:

Tp, Tq are, identically or differently, a divalent bridge selected from the group consisting of $N(R^2)$, $B(R^2)$, O, $C(R^2)_2$, $Si(R^2)_2$, C=O, C=NR$^2$, C=C(R$^2$)$_2$, S, S=O, SO$_2$, P(R$^2$) and P(=O)R$^2$;

U is, identically or differently on each occurrence, CR$^1$;

U' is, identically or differently on each occurrence, CR$^2$ or N;

p is 0 or 1; where p equals 0 means that the ring E and the ring D are linked by a single bond;

q is 0 or 1; where q equals 0 means that the ring E and the ring D are linked by a single bond;

and where p+q=1 or 2;

and where Tp and Tq are each bonded to adjacent groups U of the ring D in any possible orientation; and where furthermore each group U which is bonded to Tp or Tq represents a carbon atom;

$R^1$ is, identically or differently on each occurrence, H, D, F, Cl, Br, I, $N(R^2)_2$, CN, NO$_2$, $Si(R^2)_3$, $B(OR^2)_2$, C(=O)R$^2$, P(=O)(R$^2$)$_2$, S(=O)R$^2$, S(=O)$_2$R$^2$, OSO$_2$R$^2$, a straight-chain alkyl, alkoxy or thioalkoxy group having 1 to 40 C atoms or a straight-chain alkenyl or alkynyl group having 2 to 40 C atoms or a branched or cyclic alkyl, alkenyl, alkynyl, alkoxy, alkylalkoxy or thioalkoxy group having 3 to 40 C atoms, each of which is optionally substituted by one or more radicals R$^2$, where one or more non-adjacent CH$_2$ groups is optionally replaced by $R^2C=CR^2$, C≡C, $Si(R^2)_2$, $Ge(R^2)_2$, $Sn(R^2)_2$, C=O, C=S, C=Se, C=NR$^2$, P(=O)(R$^2$), SO, SO$_2$, NR$^2$, O, S or CONR$^2$ and where one or more H atoms is optionally replaced by D, F, Cl, Br, I, CN or NO$_2$, or an aromatic or heteroaromatic ring system having 5 to 60 aromatic ring atoms, which may in each case be substituted by one or more radicals R$^2$, or an aryloxy, arylalkoxy or heteroaryloxy group having 5 to 60 aromatic ring atoms, which is optionally substituted by one or more radicals R$^2$, or a diarylamino group, diheteroarylamino group or arylheteroarylamino group having 10 to 40 aromatic ring atoms, which is optionally substituted by one or more radicals R$^2$, two or more adjacent radicals R$^1$ here may form a mono- or polycyclic, aliphatic or aromatic ring system with one another;

$R^2$ is, identically or differently on each occurrence, H, D, F, Cl, Br, I, $N(R^3)_2$, CN, NO$_2$, $Si(R^3)_3$, $B(OR^3)_2$, C(=O)R$^3$, P(=O)(R$^3$)$_2$, S(=O)R$^3$, S(=O)$_2$R$^3$, OSO$_2$R$^3$, a straight-chain alkyl, alkoxy or thioalkoxy group having 1 to 40 C atoms or a straight-chain alkenyl or alkynyl group having 2 to 40 C atoms or a branched or cyclic alkyl, alkenyl, alkynyl, alkoxy, alkylalkoxy or thioalkoxy group having 3 to 40 C atoms, each of which is optionally substituted by one or more radicals R$^3$, where one or more non-adjacent CH$_2$ groups is optionally replaced by $R^3C=CR^3$, C≡C, $Si(R^3)_2$, $Ge(R^3)_2$, $Sn(R^3)_2$, C=O, C=S, C=Se, C=NR$^3$, P(=O)(R$^3$), SO, SO$_2$, NR$^3$, O, S or CONR$^3$ and where one or more H atoms is optionally replaced by D, F, Cl, Br, I, CN or NO$_2$, or an aromatic or heteroaromatic ring system having 5 to 60 aromatic ring atoms, which may in each case be substituted by one or more radicals R$^3$, or an aryloxy, arylalkoxy or heteroaryloxy group having 5 to 60 aromatic ring atoms, which is optionally substituted by one or more radicals R$^3$, or a diarylamino group, diheteroarylamino group or arylheteroarylamino group having 10 to 40 aromatic ring atoms, which is optionally substituted by one or more radicals R$^3$, or a combination of two or more of these groups; two or more adjacent radicals R$^2$ here may form a mono- or polycyclic, aliphatic or aromatic ring system with one another;

$R^3$ is, identically or differently on each occurrence, H, D, F or an aliphatic, aromatic and/or heteroaromatic hydrocarbon radical having 1 to 20 C atoms, in which, in addition, one or more H atoms is optionally replaced by F; two or more substituents R$^3$ here may also form a mono- or polycyclic, aliphatic or aromatic ring system with one another;

$R^4$, $R^5$ are, identically or differently on each occurrence, H, D, F, Cl, Br, I, $N(R^2)_2$, CN, NO$_2$, $Si(R^2)_3$, $B(OR^2)_2$, C(=O)R$^2$, P(=O)R$^2$, S(=O)R$^2$, S(=O)$_2$R$^2$, a straight-chain alkyl, alkoxy or thioalkoxy group having 1 to 40 C atoms or a straight-chain alkenyl or alkynyl group having 2 to 40 C atoms or a branched or cyclic alkyl, alkenyl, alkynyl, alkoxy, alkylalkoxy or thioalkoxy group having 3 to 40 C atoms.

16. The electronic device according to claim 1, wherein Y is an aromatic or heteroaromatic ring system having 5 to 60 ring atoms, $R^1$ is, identically or differently on each occurrence, H, D, F, Cl, Br, I, $N(R^2)_2$, CN, NO$_2$, $Si(R^2)_3$, $B(OR^2)_2$, C(=O)R$^2$, P(=O)(R$^2$)$_2$, S(=O)R$^2$, S(=O)$_2$R$^2$, OSO$_2$R$^2$, a straight-chain alkyl, alkoxy or thioalkoxy group having 1 to 40 C atoms or a straight-chain alkenyl or alkynyl group having 2 to 40 C atoms or a branched or cyclic alkyl, alkenyl, alkynyl, alkoxy, alkylalkoxy or thioalkoxy group having 3 to 40 C atoms, each of which is optionally substituted by one or more radicals R$^2$, where one or more non-adjacent CH$_2$ groups is optionally replaced by $R^2C=CR^2$, C≡C, $Si(R^2)_2$, $Ge(R^2)_2$, $Sn(R^2)_2$, C=O, C=S, C=Se, C=NR$^2$, P(=O)(R$^2$), SO, SO$_2$, NR$^2$, O, S or CONR$^2$ and where one or more H atoms is optionally replaced by D, F, Cl, Br, I, CN or NO$_2$, or an aromatic or heteroaromatic ring system having 5 to 60 aromatic ring atoms, which may in each case be substituted by one or more radicals R$^2$, or an aryloxy, arylalkoxy or heteroaryloxy group having 5 to 60 aromatic ring atoms, which is optionally substituted by one or more radicals R$^2$, or a diarylamino group, diheteroarylamino group or arylheteroarylamino group having 10 to 40 aromatic ring atoms, which is optionally substituted by one or more radicals R$^2$;

$R^2$ is, identically or differently on each occurrence, H, D, F, Cl, Br, I, $N(R^3)_2$, CN, NO$_2$, $Si(R^3)_3$, $B(OR^3)_2$, C(=O)R$^3$, P(=O)(R$^3$)$_2$, S(=O)R$^3$, S(=O)$_2$R$^3$, OSO$_2$R$^3$, a straight-chain alkyl, alkoxy or thioalkoxy group having 1 to 40 C atoms or a straight-chain alkenyl or alkynyl group having 2 to 40 C atoms or a branched or cyclic alkyl, alkenyl, alkynyl, alkoxy, alkylalkoxy or thioalkoxy group having 3 to 40 C atoms, each of which is optionally substituted by one or more radicals $R^3$, where one or more non-adjacent $CH_2$ groups is optionally replaced by $R^3C=CR^3$, $C≡C$, $Si(R^3)_2$, $Ge(R^3)_2$, $Sn(R^3)_2$, $C=O$, $C=S$, $C=Se$, $C=NR^3$, $P(=O)(R^3)$, SO, $SO_2$, $NR^3$, O, S or $CONR^3$ and where one or more H atoms is optionally replaced by D, F, Cl, Br, I, CN or $NO_2$, or an aromatic or heteroaromatic ring system having 5 to 60 aromatic ring atoms, which may in each case be substituted by one or more radicals $R^3$, or an aryloxy, arylalkoxy or heteroaryloxy group having 5 to 60 aromatic ring atoms, which is optionally substituted by one or more radicals $R^3$, or a diarylamino group, diheteroarylamino group or arylheteroarylamino group having 10 to 40 aromatic ring atoms, which is optionally substituted by one or more radicals $R^3$, or a combination of two or more of these groups and $R^3$ is, identically or differently on each occurrence, H, D, F or an aliphatic, aromatic and/or heteroaromatic hydrocarbon radical having 1 to 20 C atoms, in which, in addition, one or more H atoms is optionally replaced by F.

17. An electronic device comprising at least one compound of the general formula (1)

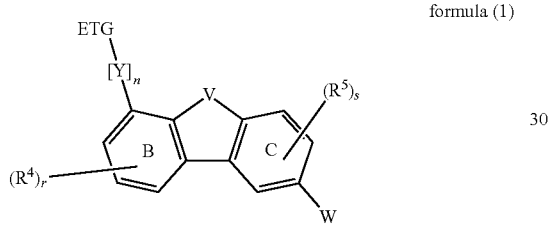

formula (1)

where the following applies to the symbols and indices used:
ETG is selected from the group of the triazines, pyrimidines, pyrazines, pyridines, quinazolines, quinolines, isoquinolines and naphthyridines and the ETG is optionally substituted by one or more radicals $R^1$, which is optionally identical or different on each occurrence;
W is triarylamine;
V is O;
Y is an aromatic or heteroaromatic ring system having 5 to 60 carbon atoms;
n is either 0 or 1;
r is an integer from 0, 1, 2 or 3;
s is an integer from 0, 1, 2 or 3;
$R^1$ is, identically or differently on each occurrence, H, D, F, Cl, Br, I, $N(R^2)_2$, CN, $NO_2$, $Si(R^2)_3$, $B(OR^2)_2$, $C(=O)R^2$, $P(=O)(R^2)_2$, $S(=O)R^2$, $S(=O)_2R^2$, $OSO_2R^2$, a straight-chain alkyl, alkoxy or thioalkoxy group having 1 to 40 C atoms or a straight-chain alkenyl or alkynyl group having 2 to 40 C atoms or a branched or cyclic alkyl, alkenyl, alkynyl, alkoxy, alkylalkoxy or thioalkoxy group having 3 to 40 C atoms, each of which is optionally substituted by one or more radicals $R^2$, where one or more non-adjacent $CH_2$ groups is optionally replaced by $R^2C=CR^2$, $C≡C$, $Si(R^2)_2$, $Ge(R^2)_2$, $Sn(R^2)_2$, $C=O$, $C=S$, $C=Se$, $C=NR^2$, $P(=O)(R^2)$, SO, $SO_2$, $NR^2$, O, S or $CONR^2$ and where one or more H atoms is optionally replaced by D, F, Cl, Br, I, CN or $NO_2$, or an aromatic or heteroaromatic ring system having 5 to 60 aromatic ring atoms, which may in each case be substituted by one or more radicals $R^2$, or an aryloxy, arylalkoxy or heteroaryloxy group having 5 to 60 aromatic ring atoms, which is optionally substituted by one or more radicals $R^2$, or a diarylamino group, diheteroarylamino group or arylheteroarylamino group having 10 to 40 aromatic ring atoms, which is optionally substituted by one or more radicals $R^2$, two or more adjacent radicals $R^1$ here may form a mono- or polycyclic, aliphatic or aromatic ring system with one another;

$R^2$ is, identically or differently on each occurrence, H, D, F, Cl, Br, I, $N(R^3)_2$, CN, $NO_2$, $Si(R^3)_3$, $B(OR^3)_2$, $C(=O)R^3$, $P(=O)(R^3)_2$, $S(=O)R^3$, $S(=O)_2R^3$, $OSO_2R^3$, a straight-chain alkyl, alkoxy or thioalkoxy group having 1 to 40 C atoms or a straight-chain alkenyl or alkynyl group having 2 to 40 C atoms or a branched or cyclic alkyl, alkenyl, alkynyl, alkoxy, alkylalkoxy or thioalkoxy group having 3 to 40 C atoms, each of which is optionally substituted by one or more radicals $R^3$, where one or more non-adjacent $CH_2$ groups is optionally replaced by $R^3C=CR^3$, $C≡C$, $Si(R^3)_2$, $Ge(R^3)_2$, $Sn(R^3)_2$, $C=O$, $C=S$, $C=Se$, $C=NR^3$, $P(=O)(R^3)$, SO, $SO_2$, $NR^3$, O, S or $CONR^3$ and where one or more H atoms is optionally replaced by D, F, Cl, Br, I, CN or $NO_2$, or an aromatic or heteroaromatic ring system having 5 to 60 aromatic ring atoms, which may in each case be substituted by one or more radicals $R^3$, or an aryloxy, arylalkoxy or heteroaryloxy group having 5 to 60 aromatic ring atoms, which is optionally substituted by one or more radicals $R^3$, or a diarylamino group, diheteroarylamino group or arylheteroarylamino group having 10 to 40 aromatic ring atoms, which is optionally substituted by one or more radicals $R^3$, or a combination of two or more of these groups; two or more adjacent radicals $R^2$ here may form a mono- or polycyclic, aliphatic or aromatic ring system with one another;

$R^3$ is, identically or differently on each occurrence, H, D, F or an aliphatic, aromatic and/or heteroaromatic hydrocarbon radical having 1 to 20 C atoms, in which, in addition, one or more H atoms is optionally replaced by F; two or more substituents $R^3$ here may also form a mono- or polycyclic, aliphatic or aromatic ring system with one another;

$R^4$, $R^5$ are, identically or differently on each occurrence, H, D, F, Cl, Br, I, $N(R^2)_2$, CN, $NO_2$, $Si(R^2)_3$, $B(OR^2)_2$, $C(=O)R^2$, $P(=O)(R^2)_2$, $S(=O)R^2$, $S(=O)_2R^2$, $OSO_2R^2$, a straight-chain alkyl, alkoxy or thioalkoxy group having 1 to 40 C atoms or a straight-chain alkenyl or alkynyl group having 2 to 40 C atoms or a branched or cyclic alkyl, alkenyl, alkynyl, alkoxy, alkylalkoxy or thioalkoxy group having 3 to 40 C atoms.

18. The electronic device according to claim 1, wherein Y is an aromatic ring system having 5 to 60 carbon atoms.

* * * * *